(12) United States Patent
Jäger

(10) Patent No.: US 11,399,754 B2
(45) Date of Patent: Aug. 2, 2022

(54) MEDICAL DEVICE FOR TRANSCUTANEOUSLY INSERTING AN INSERTABLE ELEMENT INTO A BODY TISSUE

(71) Applicant: Roche Diabetes Care, Inc., Indianapolis, IN (US)

(72) Inventor: Joachim Jäger, Bruchsal (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 882 days.

(21) Appl. No.: 16/227,282

(22) Filed: Dec. 20, 2018

(65) Prior Publication Data

US 2019/0133505 A1 May 9, 2019

Related U.S. Application Data

(63) Continuation of application No. PCT/EP2017/065290, filed on Jun. 21, 2017.

(30) Foreign Application Priority Data

Jun. 22, 2016 (EP) ..................................... 16175696
Oct. 20, 2016 (EP) ..................................... 16194823

(51) Int. Cl.
*A61B 5/1486* (2006.01)
*A61B 5/00* (2006.01)
(Continued)

(52) U.S. Cl.
CPC .......... *A61B 5/14865* (2013.01); *A61B 5/145* (2013.01); *A61B 5/1473* (2013.01);
(Continued)

(58) Field of Classification Search
CPC .............. A61B 5/14532; A61B 5/1451; A61B 5/14546; A61B 5/1468–14735;
(Continued)

(56) References Cited

U.S. PATENT DOCUMENTS 5,413,690 A 5/1995 Kost et al.
5,762,770 A 6/1998 Pritchard et al.
(Continued)

FOREIGN PATENT DOCUMENTS

CN 101128228 A 2/2008
CN 101304697 A 11/2008
(Continued)

OTHER PUBLICATIONS

International Search Report and Written Opinion, PCT/EP2017/065290, dated Oct. 16, 2017, 8 pages.
(Continued)

*Primary Examiner* — Eric F Winakur
*Assistant Examiner* — Alice Ling Zou
(74) *Attorney, Agent, or Firm* — Bose McKinney & Evans LLP

(57) ABSTRACT

A medical device for transcutaneously inserting an insertable element into a body tissue. The medical device includes an insertable element that has an in vivo distal end for subcutaneous insertion, an ex vivo proximal end, and a pre-bended insertion cannula for subcutaneously inserting the insertable element. The medical device further comprises at least one patch, which is configured to be mounted on the skin of a user. The patch has a patch base and an integrated insertion mechanism for driving the insertion cannula from a storage position within the patch into an inserted position within the body tissue on a curved insertion path.

19 Claims, 24 Drawing Sheets

(51) Int. Cl.

| | |
|---|---|
| *A61B 5/145* | (2006.01) |
| *A61M 5/158* | (2006.01) |
| *A61M 5/142* | (2006.01) |
| *A61B 5/1473* | (2006.01) |
| *A61B 17/34* | (2006.01) |
| *A61M 5/172* | (2006.01) |
| *A61B 17/00* | (2006.01) |
| *A61M 5/14* | (2006.01) |
| *A61M 5/145* | (2006.01) |
| *A61M 5/162* | (2006.01) |

(52) U.S. Cl.
CPC ........ *A61B 5/14532* (2013.01); *A61B 5/6833* (2013.01); *A61B 17/3415* (2013.01); *A61B 17/3423* (2013.01); *A61B 17/3468* (2013.01); *A61M 5/14248* (2013.01); *A61M 5/158* (2013.01); *A61M 5/1723* (2013.01); *A61B 5/14546* (2013.01); *A61B 5/6843* (2013.01); *A61B 5/6848* (2013.01); *A61B 2017/00867* (2013.01); *A61M 5/145* (2013.01); *A61M 5/1407* (2013.01); *A61M 5/162* (2013.01); *A61M 2005/14252* (2013.01); *A61M 2005/1585* (2013.01); *A61M 2005/1586* (2013.01)

(58) Field of Classification Search
CPC ..... A61B 5/1486–14865; A61B 5/4836–4839; A61B 5/6801; A61B 5/6832–6833; A61B 5/6848; A61B 5/6851–6852; A61B 5/6855; A61B 5/6849; A61B 2560/063; A61M 5/003; A61M 5/14; A61M 5/14244–2005/14252; A61M 5/158–2005/1587; A61M 2005/14284; A61M 2230/201; A61M 2005/1585; A61M 5/14248; A61M 5/1413
See application file for complete search history.

(56) References Cited

U.S. PATENT DOCUMENTS

| | | | |
|---|---|---|---|
| 5,798,031 A | 8/1998 | Charlton et al. | |
| 6,129,823 A | 10/2000 | Hughes et al. | |
| 6,360,888 B1 | 3/2002 | McIvor et al. | |
| 8,954,162 B2 | 2/2015 | Bonde et al. | |
| 2005/0013731 A1 | 1/2005 | Burke et al. | |
| 2007/0088254 A1 | 4/2007 | DeStefano | |
| 2008/0242962 A1 | 10/2008 | Roesicke et al. | |
| 2008/0312600 A1* | 12/2008 | Krulevitch | A61M 5/158 604/181 |
| 2009/0062767 A1* | 3/2009 | Van Antwerp | A61B 5/6846 604/504 |
| 2009/0254041 A1* | 10/2009 | Krag | A61M 5/14248 604/180 |
| 2010/0113897 A1* | 5/2010 | Brenneman | A61B 5/6833 600/310 |
| 2012/0226122 A1 | 9/2012 | Meuniot et al. | |
| 2012/0253145 A1 | 10/2012 | Stafford et al. | |
| 2012/0265042 A1* | 10/2012 | Neinast | A61B 5/6849 600/347 |
| 2015/0290391 A1* | 10/2015 | Schmid | A61B 5/14532 604/504 |

FOREIGN PATENT DOCUMENTS

| | | |
|---|---|---|
| CN | 101797151 A | 8/2010 |
| CN | 102065764 A | 5/2011 |
| CN | 102089021 A | 6/2011 |
| CN | 105228675 A | 1/2016 |
| DE | 954712 C | 12/1956 |
| DE | 20020566 U1 | 2/2002 |
| WO | WO 2007/071562 A1 | 6/2007 |
| WO | WO 2011/041463 A2 | 4/2011 |
| WO | WO 2014/194183 A2 | 12/2014 |

OTHER PUBLICATIONS

International Preliminary Report on Patentability, PCT/EP2017/065290, dated Aug. 9, 2018, 7 pages.

* cited by examiner

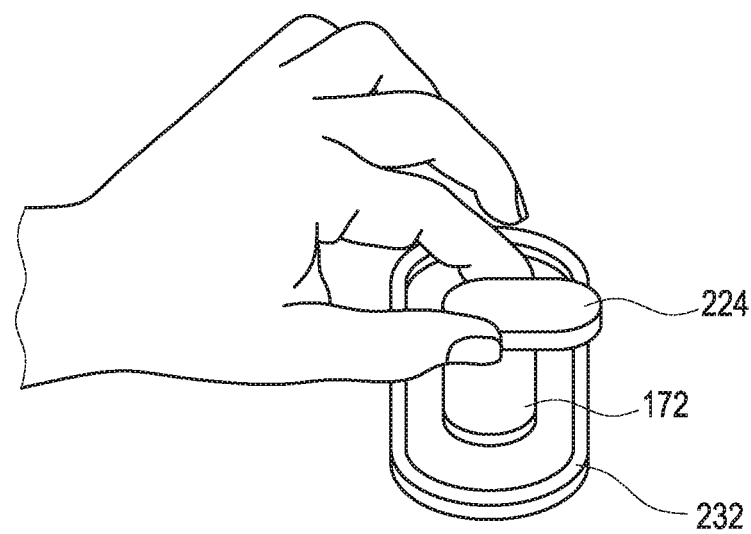
Fig. 4 B
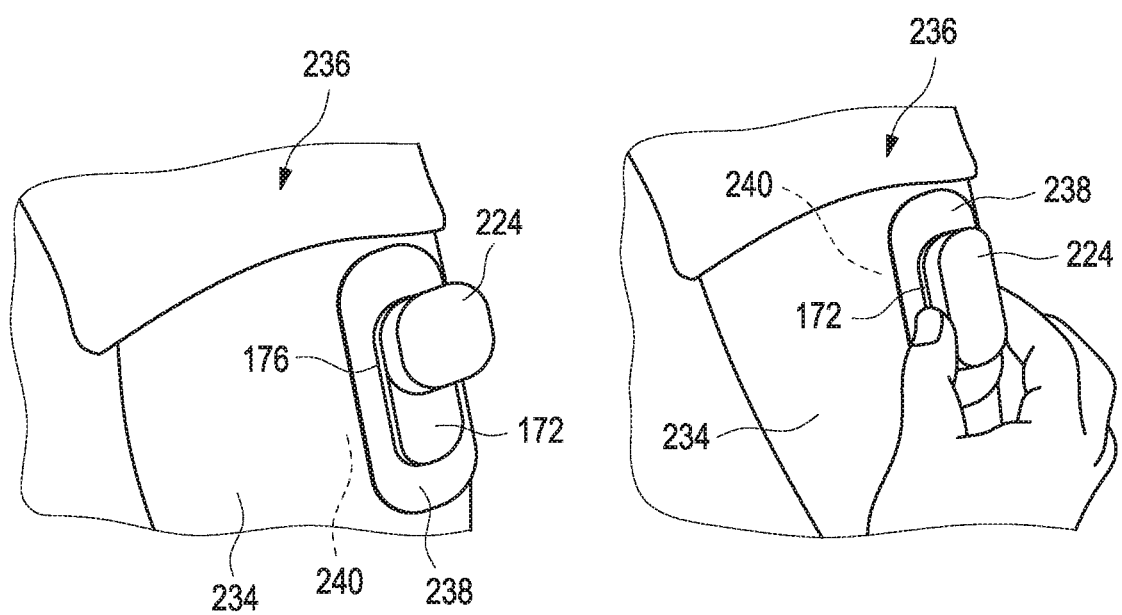
Fig. 4 C
Fig. 4 D

MEDICAL DEVICE FOR TRANSCUTANEOUSLY INSERTING AN INSERTABLE ELEMENT INTO A BODY TISSUE

RELATED APPLICATIONS

This application is a continuation of PCT/EP2017/065290, filed Jun. 21, 2017, which claims priority to EP 16 194 823.7, filed Oct. 20, 2016, and EP 16 175 696.0, filed Jun. 22, 2016, the entire disclosures of the three of which are hereby incorporated herein by reference.

BACKGROUND

This disclosure relates to a medical device for transcutaneously inserting an insertable element into a body tissue, an analyte measurement device for detecting at least one analyte in a body fluid, a medication device for delivering at least one medication to a user and a method for transcutaneously inserting an insertable element into a body tissue. The devices and method according to the present disclosure may mainly be used for long-term monitoring of an analyte concentration in a body fluid, such as for long-term monitoring of a blood glucose level or of the concentration of one or more other types of analytes in a body fluid. The invention may both be applied in the field of home care as well as in the field of professional care, such as in hospitals. Other applications are feasible.

Monitoring certain body functions, more particularly monitoring one or more concentrations of certain analytes, plays an important role in the prevention and treatment of various diseases. Without restricting further possible applications, the invention will be described in the following text with reference to blood-glucose monitoring. However, additionally or alternatively, the invention can also be applied to other types of analytes.

Blood glucose monitoring, besides by using optical measurements, specifically may be performed by using electrochemical biosensors. Examples of electrochemical biosensors for measuring glucose, specifically in blood or other body fluids, are known from U.S. Pat. Nos. 5,413,690 A, 5,762,770 A, 5,798,031 A, 6,129,823 A or US 2005/0013731 A1.

In addition to so-called spot measurements, in which a sample of a bodily fluid is taken from a user in a targeted fashion and examined with respect to the analyte concentration, continuous measurements are increasingly becoming established. Thus, in the recent past, continuous measuring of glucose in the interstitial tissue (also referred to as continuous monitoring, CM) for example has been established as another important method for managing, monitoring and controlling a diabetes state.

In the process, the active sensor region is applied directly to the measurement site, which is generally arranged in the interstitial tissue, and, for example, converts glucose into electrical charge by using an enzyme (e.g. glucose oxidase, GOD), which charge is related to the glucose concentration and can be used as a measurement variable. Examples of such transcutaneous measurement systems are described in U.S. Pat. No. 6,360,888 B1 or in US 2008/0242962 A1.

Hence, current continuous monitoring systems typically are transcutaneous systems or subcutaneous systems, and both expressions, in the following, will be used equivalently. This means that the actual sensor, or at least a measuring portion of the sensor, is arranged under the skin of the user. However, an evaluation and control part of the system (also referred to as a patch) is generally situated outside of the body of the user, outside of the human or animal body. In the process, the sensor is generally applied using an insertion instrument, which is likewise described in U.S. Pat. No. 6,360,888 B1 in an exemplary fashion. Other types of insertion instruments are also known.

The sensor typically comprises a substrate, such as a flat substrate, onto which an electrically conductive pattern of electrodes, conductive traces and contact pads may be applied. In use, the conductive traces typically are isolated by using one or more electrically insulating materials. The electrically insulating material typically also acts as a protection against humidity and other detrimental substances and, as an example, may comprise one or more cover layers such as resists.

As outlined above, in transcutaneous systems, a control part is typically required, which may be located outside the body tissue and which has to be in communication with the sensor. Typically, this communication is established by providing at least one electrical contact between the sensor and the control part, which may be a permanent electrical contact or a releasable electrical contact. Examples of electrical contacts for contacting a triangular assembly of contact pads are shown e.g. in DE 954712 B. Other techniques for providing electrical contacts, such as by appropriate spring contacts, are generally known and may be applied.

In order to avoid detrimental effects of the aggressive environment onto the conductive properties of the electrical contact, the region of the electrical contact is typically encapsulated and protected against humidity. Generally, encapsulations of electrical locks and contacts by using appropriate seals is known from, e.g., DE 200 20 566 U1. Specifically in transcutaneous or subcutaneous sensors, in which the region of electrical contact between the sensor and the control part is close to the human skin, an efficient protection against humidity, dirt, sweat and detergents, such as detergents used for body care, is crucial.

U.S. Pat. No. 8,954,162 B2 discloses a method for implanting a medical device proximate to a target tissue site within an occipital region of a patient, such as proximate to an occipital nerve or a trigeminal nerve. The method comprises introducing an implant tool into a patient to define an insertion path to the target tissue site. The implant tool includes a shape memory cannula and a malleable needle at least partially disposed within an inner lumen of the cannula. The shape of the needle may be changed to accommodate different anatomical structures/features of the patient. Upon withdrawal of the needle from the cannula, the cannula may change shape, thereby changing the shape of the insertion path.

WO 2011/041463 A2 discloses a transcutaneous sensor device configured for continuously measuring analyte concentrations in a host. In some embodiments, the transcutaneous sensor device comprises an in vivo portion configured for insertion under the skin of the host and an ex vivo portion configured to remain above the surface of the skin of the host after sensor insertion of the in vivo portion. The in vivo portion may comprise a tissue piercing element configured for piercing the skin of the host and a sensor body comprising a material or support member that provides sufficient column strength to allow the sensor body to be pushed into a host tissue without substantial buckling. The ex vivo portion may be configured to comprise (or operably connect to) a sensor electronics unit and may comprise a mounting unit. Also described here are various configurations of the sensor body and the tissue piercing element that may be used to protect the membrane of the sensor body.

US 2012/0253145 A1 discloses systems and methods for transcutaneously implanting medical devices, such as in vivo analyte sensors. The systems and methods involve the use of introducers or inserters made of shape memory alloy (SMA) materials which are able to transition from one operative state or configuration to another operative state or configuration, wherein the transition from state to state enables the transcutaneous implantation and/or transcutaneous explantation of the medical device.

Despite the advantages and the progress achieved by the above-mentioned developments, specifically in the field of continuous monitoring technology, some significant technical challenges remain. An assembly of a plurality of components is generally required, which typically implies a complex and costly manufacturing process. Further, known techniques generally require voluminous components, which is an issue, specifically considering the fact that miniaturizing the sensor systems is a factor contributing to the convenience of use.

SUMMARY

The present disclosure provides a medical device for transcutaneously inserting an insertable element into a body tissue, an analyte measurement device for detecting at least one analyte in a body fluid, a medication device for delivering at least one medication to a user and a method for transcutaneously inserting an insertable element into a body tissue, which at least partially avoid the shortcomings of known devices and methods of this kind and which at least partially address the above-mentioned challenges. Specifically, devices and methods shall be disclosed which allow for easy manufacturing and simple handling processes by a user.

Disclosed herein is a medical device for transcutaneously inserting an insertable element into a body tissue, an analyte measurement device for detecting at least one analyte in a body fluid, a medication device for delivering at least one medication to a user and a method for transcutaneously inserting an insertable element into a body tissue. The medical device may also include other features disclosed herein, either singly or in various combinations of such features.

As used in the following, the terms "have", "comprise" or "include" or any arbitrary grammatical variations thereof are used in a non-exclusive way. Thus, these terms may refer to a situation in which, besides the feature introduced by these terms, no further features are present in the entity described in this context and to a situation in which one or more further features are present. As an example, the expressions "A has B", "A comprises B" and "A includes B" may refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms, when used herein, "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, notwithstanding the fact that the respective feature or element may be present once or more than once. In the same connection, regardless of whether the phrases "one or more" or "at least one" precede an element or feature presented in this disclosure or claims, it shall be understood that such element or features shall not receive a singular interpretation unless it is made explicit herein. By way of non-limiting example, in the absence of any explicit language to the contrary, the terms "analyte," "insertable element," "in vivo distal end," and "ex vivo proximal end" to name just a few, should be interpreted to mean "at least one" or "one or more" regardless of whether or not they are introduced with the expressions "at least one" or "one or more." All other terms used herein should be similarly interpreted unless it is made explicit that a singular interpretation is intended.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The disclosure may, as the skilled person will recognize, be performed by using alternative features. Similarly, features introduced by "in an embodiment" or similar expressions are intended to be optional features, without any restriction regarding alternative embodiments of the invention, without any restrictions regarding the scope of the invention and without any restriction regarding the possibility of combining the features introduced in such way with other optional or non-optional features.

In a first embodiment, a medical device for transcutaneously inserting an insertable element into a body tissue is disclosed. The medical device comprises at least one insertable element. The insertable element comprises at least one in vivo distal end for subcutaneous insertion and at least one ex vivo proximal end. Further, the medical device comprises at least one insertion cannula for subcutaneously inserting the insertable element. The insertion cannula has a lumen which is fully or partially enclosed by a wall of the insertion cannula. The insertable element is received in the lumen. The insertion cannula is a pre-bended insertion cannula. The medical device further comprises at least one patch, configured to be mounted onto the skin of a user. The patch comprises a patch base. The patch comprises an integrated insertion mechanism for driving the insertion cannula from a storage position within the patch into an inserted position within the body tissue on a curved insertion path.

As generally used within the present disclosure, the term "medical device" may refer to an arbitrary device configured for conducting at least one medical analysis and/or at least one medical procedure. The medical device therefore generally may be an arbitrary device configured for performing at least one diagnostic purpose and/or at least one therapeutic purpose. In the following, without restricting further embodiments, the medical device mainly will be described in terms of a medical device configured for performing at least one diagnostic purpose and, specifically, a medical device comprising at least one analyte sensor for performing at least one analysis. The medical device specifically may comprise an assembly of two or more components capable of interacting with each other, such as in order to perform one or more diagnostic and/or therapeutic purposes, such as in order to perform the medical analysis and/or the medical procedure. Specifically, the two or more components may be capable of performing at least one detection of the at least one analyte in the body fluid and/or contribute to the at least one detection of the at least one analyte in the body fluid.

The medical device generally may also be or may comprise at least one of a sensor assembly, a sensor system, a sensor kit or a sensor device.

The medical device generally may be used for detecting at least one analyte in a body fluid of a user. Specifically, the medical device may be used for long-term monitoring or continuous monitoring of an analyte concentration in the body fluid of the user, such as in a body fluid contained in a body tissue of the user.

As generally used within the present disclosure, the terms "patient" and "user" may refer to a human being or an animal, independent of the fact that the human being or animal, respectively, may be in a healthy condition or may suffer from one or more diseases. As an example, the patient or the user may be a human being or an animal suffering from diabetes. However, additionally or alternatively, the disclosure may be applied to other types of users or patients or diseases.

The term "body tissue" may generally refer to a cellular organizational level intermediate between cells and a complete origin. The body tissue may specifically be an ensemble of similar cells from the same origin that together carry out a specific function. Thereby, organs may then be formed by functional grouping together of multiple tissues. For example, interstitial tissue, i.e. connective tissue between cellular elements of a structure, may be called "body tissue." As further used herein, the term "body fluid" generally may refer to a fluid which is typically present in a body or the body tissue of the user or the patient and/or which may be produced by the body of the user or the patient. Thus, as an example, the body fluid may be selected from the group consisting of blood and interstitial fluid. However, additionally or alternatively, one or more other types of body fluids may be used, such as saliva, tear fluid, urine or other body fluids.

The term "transcutaneous" generally refers to a property of an arbitrary element of being adapted to be fully or at least partly extending through the body tissue of the patient or the user. For this purpose, the element may comprise an insertable portion. In order to further render the element to be usable as a transcutaneous element, the element may fully or partially provide a biocompatible surface, i.e. a surface which, at least during durations of use, does not have any detrimental effects on the user, the patient or the body tissue. Further, the transcutaneous element generally may be dimensioned such that a transcutaneous insertion of the element into the body tissue is feasible, such as by providing a width in a direction perpendicular to an insertion direction of no more than 5 mm, preferably of no more than 2 mm, more preferably of no more than 1.5 mm. Thus, the term "subcutaneous" may generally refer to a property of an arbitrary element of being situated or lying under the skin and within the body tissue of the user or the patient. Specifically, the object may be configured to be introduced under the skin, exemplarily as an injection.

As further used herein, the term "insertion cannula" may refer to an arbitrary element which may be insertable at least partially into an arbitrary body tissue, particularly in order to deliver or to transfer a further element. Therefore, the insertion cannula may specifically be or may comprise a hollow tube or a hollow needle.

As described above, the insertion cannula has a lumen which is fully or partially enclosed by a wall of the insertion cannula. The term "lumen" generally refers to an interior volume of an element. The interior volume may specifically be an open interior volume. Thus, the interior volume may not be fully enclosed or surrounded by a wall of the element. Instead, a flow of a fluid medium or an insertion of another object from one end of the element to a further end through the lumen may be feasible. As further used herein, the term "wall" may generally refer to an arbitrary structure, specifically a structural material, which is configured to at least partially surround another object or volume thereby defining physical limits of an object. Further, the wall may be configured to protect the volume or the other object at least partially enclosed by the wall.

Specifically, the insertion cannula may be selected from the group consisting of: a closed cannula with the wall circumferentially enclosing the lumen; a slotted cannula, with the cannula having a slot extending in an axial direction. The term "circumferentially enclosing" may generally refer to a property of an arbitrary object or volume of being fully enclosed by another object in at least two dimensions. Specifically, the lumen of the insertion cannula may be fully enclosed by the insertion cannula in directions perpendicular to a direction of extension of the insertion cannula. The term "slot" may generally refer to an opening, a slit or to a notch configured for receiving or admitting something. Specifically, the slotted cannula may comprise a slot located at one end of the insertion cannula. Thereby, the slot may form an angle of 10° to 80°, more preferably of 20° to 60°, to a longitudinal axis of the insertion cannula. The slot may be configured to facilitate an insertion of the insertion cannula into the body tissue. Optionally, the insertion cannula may comprise a further slot. The further slot may have an elongate shape and may extend along the longitudinal axis of the insertion cannula.

The insertion cannula at least partially may have an essentially rectangular shape. The term "shape" may thereby refer to a cross-section perpendicular to a direction of extension of the insertion cannula or perpendicular to the longitudinal axis of the insertion cannula. The term "essentially rectangular" may refer to a property of the shape of having slight deviations of a rectangular shape such as by small deviations of an angle of 90° between the walls of the insertion cannula. The advantage of the essentially rectangular shape of the insertion cannula is that a geometric relation between the insertion cannula and the insertable element, which may specifically be an essentially rectangular insertable element, as will further be described below, may be optimized. Further, the insertion cannula having the essentially rectangular shape may show the advantage that the insertion cannula may be flexible in a vertical axis and may be stiff in a transverse axis of the insertion cannula. Further, a force which is required to insert the insertable element may be reduced with the essentially rectangular shape in comparison to a usage of insertion cannulas with other shapes. Further, an injury of the patient may be reduced. Further, the insertion cannula may at least partially have an asymmetric shape. Thus, the cross-section perpendicular to the direction of extension of the insertion cannula may be non-symmetric with regard to an axis perpendicular to the direction of extension. However, other shapes of the insertion cannula may generally be feasible.

The insertion cannula may at least partially be made of at least one biocompatible material, i.e. a surface which, at least during durations of use, does not have any detrimental effects on the user, the patient or the body tissue. As an example, the insertion cannula, specifically the in vivo distal end, may fully or partially be covered with at least one biocompatible membrane, such as at least one polymer membrane or gel membrane which is permeable for the analyte and/or the body fluid.

As outlined above, the insertion cannula is a pre-bended insertion cannula. As used herein, the term "pre-bended" may generally refer to a geometric property of an element which, at least in absence of external forces, is an at least partially non-straight shape. Thus, the insertion cannula, at least in absence of external forces, may be at least partially non-straight. Thus, the insertion cannula may fully or partially be embodied as having a non-straight shape, specifically as fully or partially having a curved shape. Specifically, the insertion cannula may fully or partially be embodied as having the shape of a segment of a circle. Thus, the insertion cannula may be pre-bended in such a way that it fully or partially has the shape of a segment of a circle. More specifically, as an example, the pre-bended insertion cannula may be a steel cannula, specifically a stainless steel cannula, being pre-bended in such a way that it fully or partially is curved, specifically having the shape of a segment of a circle. The insertion cannula may be a stiff or rigid insertion cannula. Alternatively, however, the insertion cannula may also be flexible, specifically with respect to a change of a bending radius of the pre-bended insertion cannula. The insertion cannula, as an example, may also be made of materials that do not include a shape memory alloy.

As outlined above, the integrated insertion mechanism is configured for driving the insertion cannula from a storage position within the patch into an inserted position in which the insertion cannula is fully or partially extended into the body tissue. As used herein, the term "storage position" generally may refer to a position of the insertion cannula within the patch, in which the insertion cannula does not protrude into the body tissue. Specifically, the insertion cannula may fully or partially be surrounded by the patch. As further used herein, the term "inserted position" may generally refer to a position of the insertion cannula in which the insertion cannula fully or partially protrudes from the patch, such as by fully or partially protruding into the body tissue while preferably a proximal end of the insertion cannula is fully or partially held by the patch or connected to the patch.

In the storage position and in the inserted position, the insertion cannula may have the same shape or may have a different shape. Thus, as an example, the insertion cannula, when inside the patch, may have a flattened shape with a higher bending radius as compared to a situation in which the insertion cannula is fully or partially outside the patch. Alternatively, however, the insertion cannula may also have the same bending radius or the same shape in the storage position, i.e. in the first configuration, and in the inserted position, i.e. in the second configuration. In the latter case, as an example, the cannula may be a flexible cannula, which is pre-bended in such a way that, in the absence of external forces, it takes the second configuration.

The situation of the insertion cannula in which the insertion cannula is in the storage position may also be referred to as a first configuration of the insertion cannula or the medical device, and the situation in which the insertion cannula is in the inserted position may also be referred to as a second configuration. The terms "first configuration" and "second configuration" may be considered as nomenclature only, without numbering or ranking the named elements, without specifying an order and without excluding a possibility that several kinds of first configurations and second configuration may be present. Further, additional configurations such as one or more third configurations may be present.

The insertion cannula may comprise at least one relief cutout in the wall of the insertion cannula. The term "relief cutout" specifically may refer to a passage opening within the wall of the insertion cannula. The relief cutout may be configured to support a transformation of the insertion cannula from the first configuration to the second configuration. The relief cutout may extend essentially perpendicular to an axis of the insertion cannula.

The term "insertable element" may generally refer to an arbitrary element which may be configured to be at least partially insertable into another object such that the insertable element may be at least partially located under the object or surrounded by an interior of the object. Specifically, the insertable element may be configured to be at least partially inserted into the body tissue, specifically under the skin of the patient. Therefore, the insertable element may specifically have an elongate shape with a small cross-section.

Further, the insertable element may be configured to be removed from the body tissue subsequent to an expiration of a useful lifetime of the medical device. The term "useful lifetime" may refer to a period of time during which an arbitrary device may be applied in an intended manner. Specifically, the medical device may be configured to stay mounted onto the skin of the patient or the user for several days such as for one week or for two weeks. During this period of time, the medical device may be configured to conduct analytical measurements and/or to transfer an infusion into the body tissue, as will further be described below. Further, during this period of time, the insertable element may stay within the body tissue and the insertion cannula may also stay within the body tissue subsequent to the insertable element. Alternatively, the insertion cannula may be configured to be fully withdrawn from the body tissue into the medical device after insertion of the insertable element while only the insertable element is configured to stay at least partially within the body tissue after the insertion cannula is withdrawn into the medical device and during the useful lifetime of the medical device. Meanwhile, the insertion cannula may stay outside of the body tissue but may be incorporated within the medical device. Specifically, the insertion cannula may be protectively enclosed by the medical device such that the insertion cannula may not be a source of risk to the user or the patient. Thus, the user or the patient may have the insertion cannula protectively enclosed by the medical device, specifically by a housing of the medical device attached to the body tissue via the medical device. Thus, the insertion cannula and the insertable element may be configured to be removed from the body of the patient at the same time after the useful time of the medical device is expired.

As described above, the insertable element may comprise the in vivo distal end and, optionally, the ex vivo proximal end. As further used herein, the term "in vivo distal end" may refer to a part, specifically to an end of an object which is configured to be at least partially insertable into a living organism, specifically into a body tissue. Therefore, the in vivo distal end may refer to an end opposing an end which corresponds to a point of attachment of the object. The term "ex vivo proximal end" may refer to a part, specifically to an end of an object which is configured to stay outside of a living organism. Therefore, the ex vivo proximal end may refer to an end which corresponds to a point of attachment of the object. Thus, the in vivo distal end and the ex vivo proximal end may be opposing ends of one single object, whereby the object is configured to be partially inserted into a living organism via the in vivo distal end while one part of the object may stay outside of the living organism. Generally, the insertable element may have an elongate shape with a small cross-section. The insertable element may be at least partially made of a biocompatible material. Further, the insertable element may, at least to a large extent, be made of an elastic material.

The insertable element may be selected from the group consisting of: a sensor, specifically a biosensor, preferably an analyte sensor for detecting at least one analyte in a body fluid; a sensor configured for remaining under the skin after removing the insertion cannula; an infusion cannula; a dosing tube.

As further used herein, the terms "sensor" and "analyte sensor" may generally refer to an arbitrary element which is adapted to perform a process of detection and/or which is adapted to be used in the process of detection. Thus, the sensor specifically may be adapted to determine the concentration of the analyte and/or a presence of the analyte. The term "detection" generally refers to a process of determining a presence and/or a quantity and/or a concentration of the at least one analyte. Thus, the detection may be or may comprise a qualitative detection, simply determining the presence or the absence of the at least one analyte, and/or may be or may comprise a quantitative detection, which determines the quantity and/or the concentration of the at least one analyte. As a result of the detection, at least one signal may be produced which characterizes an outcome of the detection, such as at least one measurement signal. The at least one signal specifically may be or may comprise at least one electronic signal such as at least one voltage and/or at least one current. The at least one signal may be or may comprise at least one analog signal and/or may be or may comprise at least one digital signal.

The analyte sensor specifically may be an electrochemical sensor. As used herein, an "electrochemical sensor" generally is a sensor which is configured to conduct an electrochemical measurement in order to detect the at least one analyte contained in the body fluid. The term "electrochemical measurement" refers to a detection of an electrochemically detectable property of the analyte, such as an electrochemical detection reaction. Thus, for example, the electrochemical detection reaction may be detected by comparing one or more electrode potentials. The electrochemical sensor specifically may be adapted to and/or may be usable to generate at least one electrical sensor signal which directly or indirectly indicates the presence and/or the extent of the electrochemical detection reaction, such as at least one current and/or at least one voltage. The detection may be analyte-specific. The measurement may be a qualitative and/or a quantitative measurement. Still, other embodiments are feasible. The analyte sensor may comprise at least two electrodes. The two electrodes may comprise at least one working electrode. As used herein, the term "working electrode" refers to an electrode being adapted for or being usable for performing at least one electrochemical detection reaction for detecting the at least one analyte in the body fluid. The working electrode may have at least one test chemical being sensitive to the analyte to be detected. The term "test chemical" specifically may refer to an arbitrary material or a composition of materials adapted to change at least one detectable property in the presence of at least one analyte. This property may be an electrochemically detectable property. Specifically, the at least one test chemical may be a highly selective test chemical, which only changes the property if the analyte is present in the body fluid, whereas no change occurs if the analyte is not present. The degree of change of the at least one property is dependent on the concentration of the analyte in the body fluid in order to allow a quantitative detection of the analyte. As an example, the test chemical may comprise at least one enzyme, such as glucose oxidase and/or glucose dehydrogenase. The at least two electrodes may further comprise at least one counter electrode. As used herein, the term "counter electrode" refers to an electrode adapted for performing at least one electrochemical counter reaction and adapted for balancing a current flow required by the detection reaction at the working electrode. Additionally or alternatively the at least two electrodes may further comprise at least one reference electrode. The reference electrode may have a stable and well-known electrode potential. For potential materials usable for the counter electrode and/or the reference electrode, reference may be made to WO 2007/071562 A1 and the prior art documents disclosed therein, all of which are hereby incorporated by reference. Other embodiments, however, are feasible.

As further used herein, the term "analyte" may refer to an arbitrary element, component or compound which may be present in the body fluid and the presence and/or the concentration of which may be of interest for the user, the patient or medical staff, such as a medical doctor. Particularly, the analyte may be or may comprise an arbitrary chemical substance or chemical compound which may take part in the metabolism of the user or the patient, such as at least one metabolite. As an example, the at least one analyte may be selected from the group consisting of glucose, cholesterol, triglycerides, lactate. Additionally or alternatively, however, other types of analytes may be used and/or any combination of analytes may be determined. The detection of the at least one analyte may be an analyte-specific detection.

The analyte sensor may further comprise at least one substrate. The at least two electrodes and/or at least two sensor contacts generally may be attached to the substrate. The sensor may further comprise at least two electrical traces which interconnect the electrodes and the sensor contacts and which may also be attached to the substrate. As used herein, the term "substrate" may generally refer to an arbitrary element which is suitable to carry one or more other elements disposed thereon or therein. As an example, the substrate may be a flat substrate, such as a substrate having a lateral extension exceeding its thickness by at least a factor of 2, at least a factor of 5, at least a factor of 10, or even at least a factor of 20 or more. The substrate specifically may have an elongated shape, such as a strip-shape and/or a bar-shape. The substrate, as an example, may comprise a shaft, specifically a shaft having an elongate shape. For example, the shaft may have a shape selected from the group consisting of a strip, a needle, a tape.

The analyte sensor may have a length of less than 50 mm, such as a length of 30 mm or less, e.g. a length of 5 mm to 30 mm. The term "length" as further used herein may be viewed in a direction parallel to the insertion direction. It shall be noted, however, that other dimensions are feasible. The analyte sensor may have a shape corresponding to the shape of the insertion cannula. Specifically, the insertable element may have a rectangular shape and the analyte sensor may have a rectangular shape correspondingly.

The term "infusion cannula" may generally refer to an arbitrary cannula being configured to introduce an infusion, i.e. a liquid substance, specifically a liquid substance comprising a medicine, into the body tissue, for example, directly into a vein of the patient. Therefore, the infusion cannula may be attached to a reservoir comprising the liquid substance, specifically via the ex vivo proximal end of the infusion cannula. The infusion cannula may be part of an infusion kit. The term "infusion kit" may refer to an assembly of components which are required for conducting an arbitrary infusion. Thus, besides the infusion cannula, the infusion kit may further comprise at least one fluid coupling for coupling the infusion kit to at least one medication device, preferably to at least one medication pump.

The insertion cannula specifically may fully or partially be made of at least one material selected from the group consisting of: steel, specifically stainless steel; a plastic material, specifically a flexible plastic material. Specifically, the insertion cannula and the wall may not comprise a shape memory alloy. Thus, specifically, the insertion cannula may fully or partially be made of one or more materials other than a shape memory alloy. Thus, as an example, the insertion cannula may be realized as a bent steel cannula, specifically as a pre-bended steel cannula, more specifically as a pre-bended stainless steel cannula. As discussed above, both the first configuration and the second configurations may be pre-bended configurations, specifically bent configurations following an arc of a circle or having an arc form.

As outlined above, the medical device comprises the at least one patch, configured to be mounted onto the skin of a user, wherein the patch comprises a patch base and an integrated insertion mechanism for driving the insertion cannula from a storage position within the patch into an inserted position within the body tissue on a curved insertion path.

As outlined above, during insertion, the insertion cannula may maintain its shape or may be deformed, e.g. relaxed. As an example, the insertion cannula may be forced into the first configuration within the patch and may relax when being transformed into the second configuration. Thus, as an example, the relaxed form of the insertion cannula may be the second shape configuration which, specifically, may be bent. Thus, as an example, the medical device may have a patch or patch base configured for attachment to the skin of the user. Before and, optionally, also after insertion, the insertion cannula may be stored within the patch or patch base, in the storage position or first configuration. During insertion, a tip of the insertion cannula may be pushed out of the medical device, e.g. out of a patch or patch base of the medical device, e.g. through an insertion opening in a bottom surface of the patch or patch base. When fully extended from the patch or patch base, as an example, the insertion cannula may take the second configuration. The insertion cannula may be bent into a direction facing into the body tissue. A center of curvature of the insertion cannula may be located underneath the patch or patch base, e.g. in the body tissue. A proximal end of the insertion cannula may be held by the patch or patch base. After insertion, the insertion cannula may be retracted into the patch or patch base by the integrated insertion mechanism, e.g. by being pulled back into the interior space and/or into the channel of the patch or patch base.

As discussed above, the lumen specifically may have a rectangular cross-section. The insertion cannula specifically may be a slotted insertion cannula, with a slot located at a short side of the rectangular cross-section. Thus, as an example, the insertion cannula may be a bent, slotted stainless steel cannula having a rectangular cross section, with the longer sides of the rectangle being located at circumferential surfaces and with the shorter sides being oriented perpendicular thereto, one of the shorter sides having the slot of the insertion cannula.

As discussed above, the medical device comprises at least one patch, configured to be mounted onto the skin of a user. As used herein, the term "patch" generally refers to a device which is attachable to the skin or a skin site of a user or a patient. Thus, the patch may comprise at least one attachment component which is capable of connecting the body mount to the skin, such as at least one adhesive surface and/or at least one adhesive strip or plaster.

The patch comprises a patch base. As further used herein, the term "base" may refer to an arbitrary support for an object on which further components of the object rest. Thereby, the base may have a supporting surface serving bearing area for the further components. Specifically, the patch base may be a flat element. The patch base may comprise a bottom surface facing the body tissue of the user or the patient. The bottom surface may be the adhesive surface as described above. Further, the patch base may comprise an upper surface. The upper surface may be configured as bearing surface and may be configured to serve as a host for further components of the medical device. Therefore, the patch may also be referred to as a sensor support or as a body mount.

The patch comprises the integrated insertion mechanism configured for driving the insertion cannula from the storage position within the patch into the inserted position within the body tissue on a curved insertion path, and, optionally, also for subsequently driving the insertion cannula back from the inserted position into the storage position.

The term "on a curved path", as used herein, specifically may refer to the fact that a tip of the insertion cannula, during movement from the storage position into the inserted position follows a path which, at least partially, is non-straight. Specifically, the path may at least partially have the shape of a segment of a circle.

The term "insertion mechanism" may generally refer to an assembly of components which are configured to interact with each other with the purpose of inserting an element at least partially into another object. Therefore, the insertion mechanism may be configured such that a movement of the element in a direction of insertion, i.e. toward a surface of the other object is introduced. The insertion mechanism may be an integrated insertion mechanism. Thus, the assembly of the components which are configured to interact with each other with the purpose of inserting the element at least partially into another object may be provided as one unit, as a whole and/or as an "all-in-one" system. Thus, the user may find the medical device comprising a fully assembled insertion mechanism without the need to add other components to the medical device or the need to apply a further device in addition to the medical device for the purpose of inserting the insertion cannula into the body tissue.

The insertion cannula may be at least partially connected to the patch base and/or placed inside the patch base. Specifically, the insertion cannula may be stored in the first configuration inside the patch. The insertion cannula, in the second configuration, may be at least partially located outside of the patch or protrude from the patch. The insertion cannula may be movable from the patch into the body tissue through the passage opening and vice versa. A shape of the passage opening may correspond to a shape of the insertion cannula. Specifically, the shape of the passage opening may correspond to a rectangular shape of the insertion cannula.

The insertion mechanism may comprise at least one drive unit. The term "drive unit" may generally refer to an element or an assembly of elements which are configured to interact with each other in order to create a force leading to a movement, specifically a pre-determined movement, of another element. Specifically, the drive unit may be configured to urge the insertion cannula in a direction of insertion, preferably by pushing or pulling the insertion cannula. The drive unit may be triggered or driven via a rotational mechanism. The term "rotational mechanism" may refer to a rotational movement of one or more components of an assembly of elements with the purpose to move another element. Thereby, the movement of the material itself may exemplarily be a unidirectional movement.

The medical device may further comprise at least one element connected or connectable to the patch base, preferably at least one element interacting with the insertable element, preferably one of an electronics unit or a medication pump, particularly via a force-fit connection.

The integrated insertion mechanism specifically may be or may comprise at least one linear sliding mechanism. The at least one element connected or connectable to the patch base specifically may comprise at least one linear sliding receptacle, and the patch specifically may comprise at least one linear sliding guide rail, or vice versa. The linear sliding receptacle and the linear sliding guide rail, in conjunction, may form a linear sliding connector configured for establishing a releasable mechanical connection between the at least one element connected or connectable to the patch base and the patch.

In case the at least one element connected or connectable to the patch base comprises at least one electronics unit or another type of element such as a medication pump, the element, specifically the electronics unit, may comprise at least one bayonet screw. Specifically, the electronics unit may comprise at least one electronics unit bayonet screw. The patch may comprise at least one patch bayonet contour, wherein the patch bayonet contour and the electronics unit bayonet screw, in conjunction, may form a bayonet connector configured for establishing a releasable mechanical connection between the electronics unit and the patch.

The at least one element connected or connectable to the patch base, as indicated above, specifically may comprise at least one element selected from the group consisting of: an electronics unit configured for interacting with the insertable element; a slider, specifically a U-shaped slider; a bracket, specifically a U-shaped bracket.

The at least one element connected or connectable to the patch base specifically may be configured to be brought from at least one standby position into at least one actuated position. As used therein, the term "standby position" generally refers to a position in which the element connected or connectable to the patch base is ready to be actuated by a user, e.g. directly or after removal of a securing or safety element. Further, as used therein, the term "actuated position" generally may refer to a position in which the element connected or connectable to the patch base is fully connected to the patch base, e.g., by having reached an end position in which the element is secured to the patch base. In this actuated position, the element connected or connectable to the patch base may have triggered an insertion of the insertable element with the insertion cannula into the body tissue. Further, in this actuated position, after having inserted the insertable element into the body tissue, the insertion cannula may already have retracted into the patch or patch base. For bringing the at least one element connected or connectable to the patch base from the standby position into the actuated position, specifically, a pushing motion may be used. Thus, the patch or patch base and the element connected or connectable to the patch base may be configured for allowing for a pushing motion of the element, e.g. by providing an appropriate slide or sliding mechanism.

The medical device specifically may be configured for inserting the insertion cannula into the body tissue, i.e. for bringing the insertion cannula from the storage position or first configuration into the inserted position or second configuration, when the at least one element connected or connectable to the patch base is brought into the actuated position, such as during the motion from the standby position into the actuated position or when the actuated position has been reached. Additionally, the medical device may further be configured for retracting the insertion cannula, e.g., into the patch or patch base, thereby bringing the insertion cannula back from the inserted position or second configuration into the storage position or first configuration once the actuated position has been reached and preferably once the insertable element has been inserted into the body tissue.

The at least one element connected or connectable to the patch base, which may be used as an actuator for actuating an insertion motion, specifically when in the actuated position, may be flush with the housing of the medical device. Thus, the at least one element connected or connectable to the patch base may be flush with the remaining housing of the patch base, thereby, in conjunction with a housing of the patch base, forming a smooth housing, without any protruding parts. Consequently, the at least one element connected or connectable to the patch base may form or may contribute a part to the housing of the medical device. In the standby position, the part may protrude from the housing, ready for being actuated by pushing it back into the housing, and in the actuated position, this part may be flush with the remaining housing.

As outlined above, the medical device may further comprise at least one removable securing element, which may also be referred to as a safety element or as a safety lock. The securing element may be configured for securing the at least one element connected or connectable to the patch base in the standby position. For removing the securing element, the securing element may fully be removed from the medical device or may be brought into an unlocked position. The securing element may also be combined with other functions of the medical device. Thus, as an example, the securing element may comprise at least one desiccant.

In addition or as an alternative to the linear sliding mechanism, as discussed above, a rotational mechanism may be used. The insertion mechanism may be configured to be driven by the rotational mechanism as described above, specifically by a rotational movement of the element connected or connectable to the patch base, particularly via a connecting force exerted when connecting the element to the patch base. Therefore, the insertion mechanism may comprise at least one pin. The term "pin" may specifically refer to a small, elongate element which may specifically be made of a stiff material. The pin may be engageable and/or driven by the at least one element connected or connectable to the patch base. The insertion mechanism may be configured to be driven by the connecting force exerted via the pin when connecting the element to the patch base. Further, the pin may be connected to the patch via one or more links. The term "link" may refer to a small, elongate object which may be fixedly connected to at least two elements. Thus, the link may form a connection of the two elements. Specifically, the links may be configured to be broken off from the patch before insertion. Thus, the drive unit may be triggered through a breakaway torque. Further, optionally, the insertion mechanism may comprise at least one spring. The spring may be configured to be driven by a spring load of the spring. The insertion mechanism, specifically the drive unit, may comprise at least one flexible wire configured for driving and insertion of the insertable element. The flexible wire may be a flexible guide wire. One end of the flexible guide wire facing the insertion cannula may be elastic and the other end of the flexible guide wire may be stiff.

The insertion mechanism may comprise at least one return spring. The term "return spring" may generally refer to an arbitrary elastic object which is used to store mechanical energy. In case an object may be coupled to the return spring, the return spring may be configured to be tensioned when the object is moved. Thereby, the return spring may be configured to move the object back to its original position when the return spring is relaxed. Specifically, the return spring may be configured to be tensioned during insertion of the insertable element into the body tissue. Further, the return spring may be configured to support a withdrawing of the insertion cannula from the body tissue after insertion.

Further, the insertion cannula may be configured such that, after insertion, a tip of the insertion cannula is at least partially embedded in material of the patch. Thereby, the insertable element may be protected from the insertion cannula, specifically from the end of the insertion cannula, which may comprise the slot.

Specifically, the insertion cannula may be a slotted cannula comprising at least one axial slot that extends along the direction of extension of the insertion cannula and the insertable element may comprise at least one protrusion. The term "protrusion" may generally refer to an arbitrary element or part of an object which protrudes from a surface of the object. The protrusion may at least partially protrude through the slot. The protrusion may be configured for preventing, at least to a large extent, a displacement of the insertable element against a direction of insertion of the insertion cannula. The medical device may be configured to hold the protrusion when retracting the insertion cannula from the body tissue, thereby preventing the insertable element from being retracted from the body tissue.

The medical device may further comprise at least one holding down clamp. The term "holding down clamp" may generally refer to an arbitrary element, which is configured to hold or secure an object in a certain position in order to prevent an undesired movement or separation from another element, specifically through an application of an inward pressure. The holding down clamp may be configured to prevent, at least to a large extent, a withdrawing of the insertable element from the body tissue after insertion. The holding down clamp may be configured to press onto the insertable element, thereby holding the insertable element in the second configuration. Specifically, the holding down clamp may be identical to the protrusion as described above, or as will further be described below.

Additionally or alternatively, the insertable element may comprise one or more clamps. As further used herein, the term "clamp" may refer to an object which is configured to hold or to fix an element into a certain position. The clamps may be located within an interior of the insertion cannula, specifically within the lumen of the insertion cannula. Specifically, the clamps may be configured to stick the insertable element within the interior of the insertion cannula during insertion. The clamps may be configured to release the insertable element before withdrawing the insertion cannula. For example, the clamps may comprise arms protruding from the insertable element. The arms may engage with an interior side of the wall of the cannula. The arms may enable the insertable element to move in the direction of the proximal end and prevent the insertable element from moving in an opposite direction.

The medical device, as outlined above, may further comprise at least one electronics unit configured for interacting with the insertable element. As used herein, the term "electronics unit" generally refers to an arbitrary device having at least one electronic component. Specifically, the electronics unit may comprise at least one electronic component for one or more of performing a measurement with the sensor, performing a voltage measurement, performing a current measurement, recording sensor signals, storing measurement signals or measurement data, transmitting sensor signals or measurement data to another device. The electronics unit may specifically be embodied as a transmitter or may comprise a transmitter, for transmitting data. Other embodiments of the electronic components are feasible.

The electronics unit may comprise at least one interconnect device, preferably a printed circuit board, more preferably a flexible printed circuit board. The sensor may be "operably connected" to the electronics unit. The term "operably connected" may specifically refer to a state, wherein two or more objects are connected to each other such that they can interact with each other. Specifically, the sensor may be operably connected to the electronics unit such that sensor signals of the sensor may be transmitted to the electronics unit.

The electronics unit, e.g., in addition or as an alternative to the above-mentioned sliding mechanism, may comprise at least one electronics unit bayonet screw. The patch may comprise at least one patch bayonet contour. The patch bayonet contour, in conjunction with the electronics unit bayonet contour, may form a bayonet contour configured for establishing a releasable mechanical connection between the electronics unit and the patch. As generally used herein, the term "bayonet contour" refers to a component or part of an element which is configured to interact with a counterpart bayonet contour in order to form a bayonet connection or a bayonet connector. Thus, the patch bayonet contour and the electronics unit bayonet contour may be complementary bayonet contours configured for forming a bayonet connection or, in conjunction, a bayonet connector. Therein, one of the patch bayonet contour or the electronics unit bayonet contour may be or may comprise a male bayonet contour, such as a male bayonet plug, and the other one of the patch bayonet contour or the electronics unit bayonet contour may be or may comprise a female bayonet contour, such as a female bayonet plug. As generally used herein, a bayonet connector, also referred to as a bayonet connection, may generally refer to an arbitrary connector or connection between two bayonet contours in a bayonet fashion. Therein, generally, one or both of the bayonet contours involved may comprise at least one protrusion and, in a complementary fashion, the other one of the bayonet contours may comprise at least one bayonet grove or bayonet slot in which the protrusion may be guided, such that two bayonet contours interact in order to form the bayonet connection or bayonet connector.

The electronics unit may further comprise at least two electrical contacts. In a mated state, in which the releasable mechanical connection between the electronics unit and the patch is established by the bayonet connector, an electrical connection between contacts located in the patch bayonet contour and the electrical contacts of the electronics unit may be established. In a mated state, in which the releasable mechanical connection between the electronics unit and the patch is established by the bayonet connector, the electronics unit may be pressed onto the patch or vice versa, by means of the bayonet connector.

As used herein, the term "mechanical connection" generally refers to a connection of two or more components by mechanical holding forces. As an example, the mechanical connection may be or may comprise at least one of a form-fit or a force-fit connection. In the case of the bayonet connector or bayonet connection, specifically, the mechanical connection may be a form-fit connection. As further used herein, the term "releasable", in the context of the mechanical connection, generally refers to the fact that the mechanical connection may be brought from a disconnected state, also referred to as a non-mated state, into a connected state, also referred to as a mated state, and back into the disconnected state. Thus, the mechanical connection may be closed and released at will. Specifically, the mechanical connection may be releasable without using any tools, simply by manual action. As an example, for opening the bayonet connector, forces of no more than 50 N, such as of no more than 20 N, such as of no more than 10 N, may be required, which may be applied by one hand or even the fingers or fingertips of the user.

Further, the integrated insertion mechanism may be or may comprise a linear sliding mechanism. The term "linear sliding mechanism" may refer to an arbitrary mechanism which is based on a linear sliding movement of two or more components relative to each other. Thereby, the term "sliding movement" may refer to a movement along in a continuous connection with another element, specifically with a surface, more specifically with a smooth surface, of the other element. Specifically, the linear sliding mechanism may comprise one or more interacting sliding elements, such as one or more guide rails or the like. Further, the term "linear sliding movement" may generally refer to a movement along a straight line, e.g., within two dimensions. Specifically, the electronics unit may comprise at least one linear sliding receptacle and the patch comprises at least one linear sliding guide rail or vice versa. As further used herein, the terms "linear sliding receptacle" and "linear sliding guide rail" may refer to elements which are complementary to each other and which are configured to interact with each other in order to realize the linear sliding mechanism. For example, the linear sliding guide rail is formed as a protrusion of the patch or of the electronics unit and the linear sliding receptacle may be part of the electronics unit. However, other embodiments may be feasible. Alternatively, the linear sliding guide rail may be part of the electronics unit and the linear sliding receptacle may be part of the patch. The linear sliding guide rail and the linear sliding receptacle are shaped complementary to each other. For example, the linear sliding receptacle and the linear guide rail may have an elongate shape and may extend along a longitudinal axis of the electronics unit and/or of the patch. The linear sliding receptacle and the linear sliding guide rail in conjunction may form a linear sliding connector configured for establishing a releasable mechanical connection between the electronics unit and the patch. The term "linear sliding connector", also referred to as a linear sliding connection, may generally refer to an arbitrary connector or connection between two linear sliding contours. Therein, generally, one or both of the linear sliding contours involved may comprise at least one protrusion and, in a complementary fashion, the other one of the linear sliding contours may comprise at least one linear sliding grove or linear sliding slot in which the protrusion may be guided in order to form the linear sliding connection or linear sliding connector.

The linear sliding mechanism may comprise the return spring as described above or as will further be described below in more detail. For example, the return spring may be located next to the insertion cannula. The return spring may be fixedly connected to the drive arm via at least one connector element such as a cannula sleeve.

Specifically, one end of the return spring may be attached to the cannula sleeve and the cannula sleeve may further be attached, specifically fixedly attached, to the drive arm as described above or as will further be described below in more detail. Further, the insertable element may be fixedly attached to the drive arm, specifically via at least one fixation element. Specifically, the fixed end may be located on one end of the drive arm and the cannula sleeve may be connected to the opposing end of the drive arm. The drive arm may be configured to be movable in a linear direction when the linear sliding mechanism is applied, thereby inserting the insertion cannula and the insertable element into the body tissue. Further, the return spring may be configured to be compressed when inserting the insertion cannula and the insertable element into the body tissue. Moreover, the cannula sleeve may be configured to be moveable in a linear fashion when the return spring relaxes, thereby withdrawing the drive arm.

Further, the insertion cannula may be at least partially received within the return spring when the return spring is in an outstretched configuration. Specifically, the return spring and the insertion cannula may be at least partially received in a receptacle of the patch. Further, the return spring, specifically one of the ends of the return spring, is attached to the cannula sleeve and the insertion cannula is fixedly attached to the cannula sleeve. The cannula sleeve may be configured to be moveable in a linear fashion, thereby compressing the return spring. Further, the cannula sleeve may be configured to be moveable in a linear fashion, thereby inserting the insertion cannula into the body tissue or withdrawing the insertion cannula from the body tissue.

In a further aspect of the invention, an analyte measurement device for detecting at least one analyte in a body fluid is disclosed. The analyte measurement device comprises at least one medical device according to the present invention, e.g., as described above or as will further be described below. The insertable element comprises at least one analyte sensor for detecting the at least one analyte in the body fluid. Further, the analyte measurement device has at least one evaluation device interacting with the analyte sensor.

As further used herein, the term "analyte measurement device" generally refers to an arbitrary device configured for conducting at least one analytical measurement. The analytical measurement device may preferably be an electronic device. The analyte measurement device may be adapted to interact with the medical device, specifically with the insertable element, more specifically with the analyte sensor in order to derive at least one item of information about the analyte of the sample. Specifically, the analyte measurement device may be adapted to detect at least one signal produced by the analyte. Thus, the analyte measurement device may comprise at least one electronic evaluation device in order to derive the at least one item of information about the analyte from the at least one signal. Thus, the analyte measurement device may comprise at least one evaluation unit comprising at least one data processing device, such as a microcontroller.

In a further aspect of the present invention, a medication device for delivering at least one medication to a user is disclosed. The term "medication device" generally refers to an arbitrary device which his configured to deliver a drug and/or a therapeutic agent via a specific route of administration. Such devices are commonly used as part of one or more medical treatments.

The medication device comprises at least one medical device according to the present invention, e.g. as described above or as will further be described below. The insertable element comprises at least one of an infusion cannula or a dosing tube. The medication device further comprises at least one medication pump fluidly coupled to the insertable element. The term "medication pump" generally refers to an arbitrary pump which is configured to move a drug and/or a therapeutic agent by mechanical action. Specifically, the medication pump may be an infusion pump which is configured to infuse an arbitrary medication into a patient's circulatory system. Generally, the infusion pump may be configured to be applied intravenously or subcutaneously. However, other applications are feasible. The term "fluidly coupled" may generally refer to a property of two or more elements such that an arbitrary fluid may be transferable between the two or more elements.

In a further aspect of the present disclosure, a method for transcutaneously inserting an insertable element into a body tissue is disclosed. The method comprises the method steps as listed as follows. The method steps may be performed in the given order. However, other orders of the method steps are feasible. Further, one or more of the method steps may be performed in parallel and/or on a timely overlapping fashion. Further, one or more of the method steps may be performed repeatedly. Further, additional method steps may be present which are not listed.

The method comprises:
a) providing at least one medical device according to the present disclosure, such as described above or as will further be described below, the medical device having at least one electronics unit and at least one patch configured to be mounted onto a skin of the user, the patch having a patch base;
b) placing the patch base onto the skin; and
c) inserting the insertable element into the body tissue.

The electronics unit may fully or partially be provided as a separate component. Specifically, the electronics component may be connected to the patch base before step c) of the method may be conducted. Thereby, the inserting of the insertable element into the body tissue may be triggered and/or conducted by the electronics unit such as by a rotational movement or a translational movement of the electronics unit. Additionally or alternatively, the electronics unit may also fully or partially be integrated into the patch, such as by the electronics unit and the patch being provided as one unit. Thereby, as an example, the inserting of the insertable element into the body tissue may also be triggered and/or conducted by the electronics unit such as by the rotational movement or the translational movement of the electronics unit. Moving the electronics unit such as rotationally or translationally may also be referred to as closing the patch, specifically the patch base.

The medical device may be provided in a sterile packaging before usage. The term "packaging" may refer to an arbitrary object which is configured for fully or partially enclosing or encasing at least one other component, wherein the at least one other component, as an example, may be a component which requires protection, such as mechanical protection and/or protection against moisture and/or microbial contaminations. The term "sterile" may generally refer to a property of an arbitrary object of being, at least to a large extent, free from all forms of life and/or other biological agents such as prions, viruses, fungi, bacteria or spore forms. Thus, the sterile object may be treated by at least one sterilization process that reduces, eliminates and/or deactivates the forms of life and/or the other biological agents. The sterilization process may comprise one or more of the following techniques: heating, chemical treatment, irradiation, high pressure, filtration. However, other techniques are feasible. The sterilization process may be conducted within a specified region or area of the object such as a surface of the object.

The patch base may be fixedly connected to the sterile packaging, particularly via adhesion. The sterile packaging may be adhered to at least one adhesive surface, preferably to at least one plaster before opening the sterile packaging, wherein sterile packaging is opened via at least one predetermined opening and at least partially removed from the medical device along edges of the patch base. Inserting the insertable element into the body tissue may be conducted via one or more of the rotational movement of the electronics unit or the translational movement of the electronics unit with respect to the patch base. In case the electronics unit and the patch base are provided as one unit, as described above, the electronics unit may open a sterile barrier of the patch base and may further connect to the insertable element, specifically to the sensor, in the base plate. The sterile barrier may be part of the sterile packaging.

The proposed medical device, the analyte measurement device, the medication device and the proposed method for transcutaneously inserting an insertable element into a body tissue provide many advantages over known devices and methods.

Specifically, as compared, e.g., to vertical inserters, the integrated insertion mechanism according to the present disclosure, specifically the sliding mechanism, allows for designing a very small medical device. A compact design may be realized which also may consider requirements for new generation products and which also may take a concept of platform design into account. Specifically, the concept of the present invention may allow for designing a "horizontal system", such as a horizontal continuous glucose monitoring system or a horizontal drug administration device. Very small sterile compartments may be realized, e.g., with a sensor and a cannula. Generally, the integrated insertion mechanism, specifically the sliding mechanism, may allow for an application of the insertion cannula with less force on the skin as compared to conventional systems. Further, the insertion cannula may be completely guided during the insertion mechanism, e.g., through a very small insertion hole in the patch base. Further, a shape ratio of the insertable element, e.g., the sensor and/or the infusion cannula, to a cross-section of the insertion cannula may be improved as compared to conventional systems. Further, the patch may be designed in a very compact and small fashion as compared to conventional systems.

Commonly, current medical devices generally comprise a further construction unit. The further construction unit may be or may comprise a separate inserter or a separate insertion element. The inserter may have to be manufactured as an additional construction unit and may comprise several component parts. The inserter may be too large so that the inserter may not be configured to stay on the patient's skin during application of the medical device. Moreover, the inserter generally has to be packaged separately. Further, a disposal of the inserter has to be conducted separately, specifically as a potentially contaminated medical product. Through the large design of the inserter, high costs for sterilization may emerge, specifically if the inserter has to be sterilized as well. Moreover, in some fields of application, the inserter may not be applicable for all points of application. Commonly, the analyte sensor may have a rectangular shape. Consequently, an application of round insertion cannulas may lead to an unfavorable geometric relation with regard to a puncture area.

Usually, common medical devices may initially comprise at least two components. The two components may form a final product after application of the medical device to the body tissue of the user. The analyte sensor may commonly have to be connected to the electronics unit via the user. This may specifically lead to errors during application and thus to severe consequences such as measurement errors. Therefore, in common medical devices, elaborate constructions may generally be required to circumvent error sources. The elaborate constructions may exemplarily comprise seals, electrical contacts or locking forces.

On the contrary, by applying the medical device according to the present disclosure, the user may receive an "all-in-one" medical device without a need for assembling the medical device. The insertion mechanism may be integrated within the medical device. Consequently, no additional inserter or insertion element may be required and further construction components as well as an assembling of the further construction components may be dropped. The medical device may further be robust and low-priced. An application of the medical device to the body tissue of the user may be conducted in a simple and intuitive manner.

The medical device may comprise the insertion cannula, specifically with an, at least to a large extent, essentially rectangular shape. The insertion cannula may be received in the patch of the medical device. Through the rectangular shape of the insertion cannula, the geometric relation between the cross-section of the analyte sensor and the cross-section of the insertion cannula may optimally be used.

In the first configuration, the insertion cannula may be stored inside the patch and may specifically have an at least essentially straight configuration. This may specifically be supported by the rectangular shape of the insertion cannula. Thereby, the insertion cannula may specifically be a flat insertion cannula and the insertion cannula may be supported by the patch, specifically by the patch base.

The insertion mechanism may be configured for driving the insertion cannula. Further, the insertion mechanism may comprise the return spring which is configured to support a withdrawing of the insertion cannula. The drive unit of the insertion mechanism may specifically be triggered or driven via the rotational mechanism. The rotational mechanism may be triggered via the electronics unit. The electronics unit may be connected to the patch, specifically to the patch base, via the bayonet contour. Via a rotational movement of the electronics unit, the patch, specifically the patch base may be closed. Further, the electronics unit may be configured to seal the analyte sensor against the patch. The patch base may comprise the passage opening. Via applying the rotational mechanism, specifically by closing the patch, the insertion cannula may be inserted into the body tissue of the user or the patient. Thereby, the insertion cannula may be put through the passage opening of the patch base. The insertion cannula may be transferred into the second configuration. Specifically, the insertion cannula may have the arch form, specifically with an angle of 45° to the patch base. The patch may comprise a board, specifically a circuit board, with electrical contacts. The board may be configured to realize an electrical connection between the analyte sensor and the electronics unit.

The integrated insertion mechanism, as outlined above, specifically may be or may comprise a sliding mechanism, specifically a linear sliding mechanism which specifically may be actuated by connecting an electronics unit to the patch and/or by moving the electronics unit relative to the patch. Additionally or alternatively, however, the integrated insertion mechanism may also be or may also comprise a rotational insertion mechanism. As an example, a rotational force may be transferred to the insertion cannula by a rotational movement of the electronics unit relative to the patch base, e.g., via a flexible wire. Specifically, the insertion mechanism may comprise a pin. The pin may be configured to exert the connecting force involving the wire and the electronics unit. The flexible wire may be configured to trigger the insertion cannula. Further, the patch, specifically the patch base, may comprise the return spring. The return spring may be configured to be tensioned during insertion of the insertion cannula into the body tissue. To trigger the insertion cannula, the return spring may be configured to support a withdrawing of the insertion cannula from the body tissue after insertion. Specifically, the return spring may be tensioned during applying the rotational mechanism, specifically during closing the patch via the electronics unit.

The insertable element may comprise at least one protrusion. The protrusion may extend through the axial slot of the insertion cannula. Further, the protrusion may be configured to be attached to the patch, specifically to the patch base, and thus to prevent, or at least to reduce, at least partially a movement of the insertable element against the direction of insertion. Further, the protrusion may be configured to hold the insertable element after insertion, specifically in order to prevent the insertable element from being retracted from the body tissue. Further, a connection between the protrusion and the patch base may be disconnected, such that the analyte sensor may stay within the body tissue of the user or the patient.

In case the insertion cannula is a closed cannula, i.e. a cannula without any axial slots or openings, a coupling between the insertable element and the insertion cannula has to be ensured. Thereby, the insertable element may comprise the clamps, which are configured to stick the insertable element within the interior of the insertion cannula during insertion. Other clamps may be configured to release the insertable element before withdrawing the insertion cannula.

The medical device may be provided in a sterile packaging before usage. Thereby, the patch may be fixedly connected to the sterile packaging. The sterile packaging may be adhered to at least one adhesive surface of the patch, specifically of the patch base. After sterilizing the package, the package may be adhered to at least one adhesive surface, preferably to at least one plaster. The sterile packaging may comprise the at least one predetermined opening and the sterile packaging may be configured to be at least partially removed from the medical device along the edges of the patch base. One part of the sterile packaging may remain between the patch base and the adhesive surface, specifically the plaster. Consequently, the sterile packaging may be fully integrated into the medical device. Specifically, the medical device may only require a small volume during sterilization. Optionally, the sterile packaging may be configured to be openable by closing the patch as described above.

A number of handling steps during transcutaneously inserting the insertable element into the body tissue may be reduced. A size of the sterile packaging, specifically of the sterile packaging comprising the entire medical device, may be reduced to the size of a matchbox.

In the medication device, the dosing tube may be received in the insertion cannula. Thereby, the insertion cannula may specifically be a slotted cannula and/or a semi-circular shaped cannula. Further, the medication device may comprise the medication device fluidly coupled to the insertable element.

After inserting of the insertable element, specifically the sensor, the insertion cannula may be withdrawn into the patch such as via a reverse pulling mechanism, specifically into a receptacle such as a guidance receptacle. Further, the insertion cannula may be withdrawn from the insertable element, specifically the sensor, into a free volume within the patch via a direction change with a reverse pulling mechanism. The construction volume may even be further reduced in case the insertion cannula is integrated into the return spring of the integrated insertion mechanism. When applying the linear sliding mechanism as described above, or as will further be described below, the sterile packaging may be opened while inserting the insertable element into the body tissue. Thereby, the electronics unit may be mounted onto the patch. Consequently, a number of method steps may be reduced. Specifically, the method for transcutaneously inserting an insertable element into the body tissue may be reduced to three method steps. Further, the sterile packaging for the medical device may be reduced. Moreover, the medical device may comprise an insertion device having the insertion cannula which may be removed after inserting the insertable element into the body tissue. Thereby, a size of the patch may be reduced.

Summarizing the findings of the present disclosure, the following embodiments are advantageous:

Embodiment 1

A medical device for transcutaneously inserting an insertable element into a body tissue, wherein the medical device comprises:
  at least one insertable element, wherein the insertable element comprises at least one in vivo distal end for subcutaneous insertion and at least one ex vivo proximal end;
  at least one insertion cannula for subcutaneously inserting the insertable element, the insertion cannula having a lumen which fully or partially is enclosed by a wall of the insertion cannula, wherein the insertable element is received in the lumen, wherein the insertion cannula is a pre-bended insertion cannula,
wherein the medical device further comprises at least one patch, configured to be mounted onto the skin of a user, wherein the patch comprises a patch base, wherein the patch comprises an integrated insertion mechanism for driving the insertion cannula from a storage position within the patch into an inserted position within the body tissue on a curved insertion path.

Embodiment 2

The medical device according to the preceding embodiment, wherein the insertion cannula is at least partially made of a material selected from the group consisting of: steel, specifically stainless steel; a plastic material, specifically a flexible plastic material.

Embodiment 3

The medical device according to any one of the preceding embodiments, wherein the insertion cannula is pre-bended in such a way that the insertion cannula at least partially has the shape of a segment of a circle.

Embodiment 4

The medical device according to the preceding embodiment, wherein the insertion path, at least partially, is shaped as a segment of a circle.

Embodiment 5

The medical device according to any one of the preceding embodiments, wherein the lumen has a rectangular cross-section.

Embodiment 6

The medical device according to the preceding embodiment, wherein the insertion cannula is a slotted insertion cannula, with a slot located at a short side of the rectangular cross-section.

Embodiment 7

The medical device according to any one of the preceding embodiments, wherein the insertion cannula is selected from the group consisting of: a closed cannula with the wall circumferentially enclosing the lumen; a slotted cannula, with the insertion cannula having a slot extending in an axial direction.

Embodiment 8

The medical device according to any one of the preceding embodiments, wherein the insertion cannula at least partially has an essentially rectangular cross-section.

Embodiment 9

The medical device according to any one of the preceding embodiments, wherein the insertion cannula at least partially has an asymmetric shape.

Embodiment 10

The medical device according to any one of the preceding embodiments, wherein the insertion cannula is at least partially made of at least one biocompatible material.

Embodiment 11

The medical device according to any one of the preceding embodiments, wherein the medical device is configured such that the insertion cannula is withdrawn into the medical device after insertion of the insertable element.

Embodiment 12

The medical device according to the preceding embodiment, wherein the insertable element is configured to stay at least partially within the body tissue after the insertion cannula is withdrawn into the medical device.

Embodiment 13

The medical device according to the preceding embodiment, wherein the insertion cannula is a slotted cannula comprising at least one axial slot that extends along the major axis of the insertion cannula, wherein the insertable element comprises at least one protrusion, wherein the protrusion at least partially protrudes through the slot.

Embodiment 14

The medical device according to the preceding embodiment, wherein the protrusion is configured for preventing, at least to a large extent, a displacement of the insertable element against a direction of insertion of the insertion cannula.

Embodiment 15

The medical device according to any one of the two preceding embodiments, wherein the medical device is configured to hold the protrusion when retracting the insertion cannula from the body tissue, thereby preventing the insertable element from being retracted from the body tissue.

Embodiment 16

The medical device according to any one of the preceding embodiments, wherein the medical device further comprises at least one holding down clamp, wherein the holding down clamp is configured to prevent, at least to a large extent, a withdrawing of the insertable element from the body tissue after insertion.

Embodiment 17

The medical device according to any one of the preceding embodiments, wherein the insertable element comprises one or more clamps, wherein the clamps are configured to stick the insertable element within an interior of the insertion cannula during insertion, wherein the clamps are configured to release the insertable element before withdrawing the insertion cannula.

Embodiment 18

The medical device according to the preceding embodiment, wherein the clamps comprise arms protruding from the insertable element, the arms engaging with an interior side of the wall of the cannula, the arms enabling the insertable element to move in the direction of the proximal end of preventing the insertable element from moving in an opposite direction.

Embodiment 19

The medical device according to any one of the preceding embodiments, wherein the insertable element is selected from the group consisting of: a sensor, specifically a biosensor, preferably an analyte sensor for detecting at least one analyte in a body fluid; a sensor configured for remaining under the skin after removing the insertion cannula; an infusion cannula; a dosing tube.

Embodiment 20

The medical device according to the preceding embodiment, wherein the infusion cannula is part of an infusion kit, the infusion kit further comprising at least one fluid coupling for coupling the infusion kit to at least one medication device, preferably to at least one medication pump.

Embodiment 21

The medical device according to any one of the preceding embodiments, wherein the insertable element is, at least to a large extent, made of an elastic material.

Embodiment 22

The medical device according to any one of the preceding embodiments, wherein the insertable element is configured to be removed from the body tissue subsequent to an expiration of a useful lifetime of the medical device.

Embodiment 23

The medical device according to any one of the preceding embodiments, wherein the insertion cannula is at least partially connected to the patch base and/or placed inside the patch base.

Embodiment 24

The medical device according to any one of the preceding embodiments, wherein the integrated insertion mechanism comprises at least one drive unit, wherein the drive unit is configured to urge the insertion cannula in a direction of insertion, preferably by pushing or pulling the insertion cannula.

Embodiment 25

The medical device according to the preceding embodiment, wherein the drive unit is triggered or driven via a rotational mechanism.

Embodiment 26

The medical device according to any one of the preceding embodiments, wherein the integrated insertion mechanism is a linear sliding mechanism.

Embodiment 27

The medical device according to any one of the preceding embodiments, wherein the medical device further comprises at least one element connected or connectable to the patch base, preferably at least one element interacting with the insertable element, preferably one of an electronics unit or a medication pump, particularly via a force-fit connection, wherein the insertion mechanism is configured to be driven by a connecting force exerted when connecting the element to the patch base or when moving the element relative to the patch base.

Embodiment 28

The medical device according to the preceding embodiment, wherein the at least one element connected or connectable to the patch base comprises at least one linear sliding receptacle and the patch comprises at least one linear sliding guide rail or vice versa, wherein the linear sliding receptacle and the linear sliding guide rail in conjunction form a linear sliding connector configured for moving the element relative to the patch base or for establishing a releasable mechanical connection between the at least one element connectable to the patch base and the patch.

Embodiment 29

The medical device according to any one of the two preceding embodiments, wherein the at least one element connected or connectable to the patch base comprises at least one element selected from the group consisting of: an electronics unit configured for interacting with the insertable element; a slider, specifically a U-shaped slider; a bracket, specifically a U-shaped bracket.

Embodiment 30

The medical device according to any one of the three preceding embodiments, wherein the at least one element connected or connectable to the patch base is configured to be brought from a standby position into an actuated position, specifically by a pushing motion, wherein the medical device is configured to insert the insertion cannula into the body tissue when the at least one element connectable to the patch base is brought into the actuated position.

Embodiment 31

The medical device according to the preceding embodiment, wherein the medical device is further configured for retracting the insertion cannula once the actuated position has been reached.

Embodiment 32

The medical device according to any one of the two preceding embodiments, wherein the medical device further comprises at least one removable securing element, wherein the securing element is configured for securing the at least one element connected or connectable to the patch base in the standby position.

Embodiment 33

The medical device according to the preceding embodiment, wherein the securing element comprises at least one desiccant.

Embodiment 34

The medical device according to any one of the four preceding embodiments, wherein the at least one element connected or connectable to the patch base, when in the actuated position, is flush with a housing of the medical device.

Embodiment 35

The medical device according to any one of the preceding embodiments, wherein the integrated insertion mechanism, specifically the drive unit, comprises at least one flexible wire configured for driving and insertion of the insertable element.

Embodiment 36

The medical device according to the preceding embodiment, wherein the flexible wire is a flexible guide wire, wherein one end of the flexible guide wire facing the insertion cannula is elastic and wherein the other end of the flexible guide wire is stiff.

Embodiment 37

The medical device according to any one of the preceding embodiments, wherein the integrated insertion mechanism comprises at least one return spring, wherein the return spring is configured to support a withdrawing of the insertion cannula from the body tissue after insertion.

Embodiment 38

The medical device according to the preceding embodiment, wherein the return spring is configured to be tensioned during insertion of the insertable element into the body tissue.

Embodiment 39

The medical device according to any one of the preceding embodiments, wherein the patch comprises at least one passage opening, wherein the insertion cannula is movable from the patch into the body tissue through the passage opening and vice versa.

Embodiment 40

The medical device according to the preceding embodiment, wherein a shape of the passage opening corresponds to a shape of the insertion cannula.

Embodiment 41

The medical device according to any one of the preceding embodiments, wherein the insertion cannula is configured such that, after insertion, a tip of the insertion cannula is at least partially embedded in material of the patch.

Embodiment 42

The medical device according to any one of the preceding embodiments, wherein the medical device further comprises at least one electronics unit configured for interacting with the insertable element.

Embodiment 43

The medical device according to the preceding embodiment, wherein the electronics unit comprises at least one electronics unit bayonet screw, wherein the medical device further comprises at least one patch, wherein the patch comprises at least one patch bayonet contour, wherein the patch bayonet contour and the electronics unit bayonet screw, in conjunction, form a bayonet connector configured for establishing a releasable mechanical connection between the electronics unit and the patch.

Embodiment 44

The medical device according to the preceding embodiment, wherein the electronics unit further comprises at least two electrical contacts, wherein, in a mated state in which the releasable mechanical connection between the electronics unit and the patch is established by the bayonet connector, an electrical connection between contacts located in the patch bayonet contour and the electrical contacts of the electronics unit is established.

Embodiment 45

The medical device according to any one of the two preceding embodiments, wherein in a mated state in which the releasable mechanical connection between the electronics unit and the patch is established by the bayonet connector, the electronics unit is pressed onto the patch, or vice versa, by means of the bayonet connector.

Embodiment 46

The medical device according to any one of the four preceding embodiments, wherein the integrated insertion mechanism is a linear sliding mechanism, wherein the electronics unit comprises at least one linear sliding receptacle and the patch comprises at least one linear sliding guide rail, or vice versa, wherein the linear sliding receptacle and the linear sliding guide rail, in conjunction, form a linear sliding connector configured for establishing a releasable mechanical connection between the electronics unit and the patch.

Embodiment 47

The medical device according to the preceding embodiment, wherein the linear sliding guide rail is formed as a protrusion of the patch or of the electronics unit.

Embodiment 48

The medical device according to any one of the two preceding embodiments, wherein the linear sliding guide rail and the linear sliding receptacle are shaped complementary to each other.

Embodiment 49

The medical device according to any one of the three preceding embodiments, wherein the linear sliding receptacle and the linear sliding guide rail may have an elongate shape and may extend along a longitudinal axis of the electronics unit.

Embodiment 50

The medical device according to any one of the four preceding embodiments, wherein the insertable element may be fixedly attached to a drive arm, specifically via at least one fixation element.

Embodiment 51

The medical device according to the preceding embodiment, wherein the drive arm is configured to be movable in a linear direction when the linear sliding mechanism is applied, thereby inserting the insertion cannula and the insertable element into the body tissue.

Embodiment 52

The medical device according to any one of the six preceding embodiments, wherein the linear sliding mechanism comprises at least one return spring, which is configured to be compressed when inserting the insertion cannula and the insertable element into the body tissue.

Embodiment 53

The medical device according to the preceding embodiment, wherein the return spring is located next to the insertion cannula.

Embodiment 54

The medical device according to any one of the two preceding embodiments, wherein the insertion cannula is at least partially received within the return spring when the return spring is in an outstretched configuration.

Embodiment 55

The medical device according to the preceding embodiment, wherein one end of the return spring is attached to a cannula sleeve, wherein the insertion cannula is fixedly attached to the cannula sleeve.

Embodiment 56

The medical device according to the preceding embodiment, wherein the cannula sleeve is configured to be moveable in a linear fashion, thereby inserting the insertion cannula into the body tissue or withdrawing the inserting cannula from the body tissue.

Embodiment 57

An analyte measurement device for detecting at least one analyte in a body fluid, the analyte measurement device comprising at least one medical device according to any one of the preceding embodiments, wherein the insertable element comprises at least one analyte sensor for detecting the at least one analyte in the body fluid, the analyte measurement device further having at least one evaluation device interacting with the analyte sensor.

Embodiment 58

A medication device for delivering at least one medication to a user, the medication device comprising at least one medical device according to any one of the preceding embodiments referring to a medical device, wherein the insertable element comprises at least one of an infusion cannula or a dosing tube, wherein the medication device further comprises at least one medication pump fluidly coupled to the insertable element.

Embodiment 59

A method for transcutaneously inserting an insertable element into a body tissue, wherein the method comprises:
  providing at least one medical device according to any one of the preceding embodiments referring to a medical device, the medical device having at least one electronics unit and at least one patch configured to be mounted onto the skin of a user, the patch having a patch base;
  placing the patch base onto the skin; and
  inserting the insertable element into the body tissue.

Embodiment 60

The method according to the preceding embodiment, wherein the medical device is provided in a sterile packaging before usage.

Embodiment 61

The method according to the preceding embodiment, wherein the patch base is fixedly connected to the sterile packaging, particularly via adhesion.

Embodiment 62

The method according to the preceding embodiment, wherein the sterile packaging is adhered to at least one adhesive surface, preferably to at least one plaster before opening the sterile packaging, wherein sterile packaging is opened via at least one predetermined opening and at least partially removed from the medical device along edges of the patch base.

Embodiment 63

The method according to any one of the preceding method embodiments, wherein inserting the insertable element into the body tissue is conducted via one or more of a rotational movement of the electronics unit or a translational movement of the electronics unit with respect to the patch base.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following description. Rather, the embodiments are chosen and described so that others skilled in the art may appreciate and understand the principles and practices of this disclosure.

Figure 1:
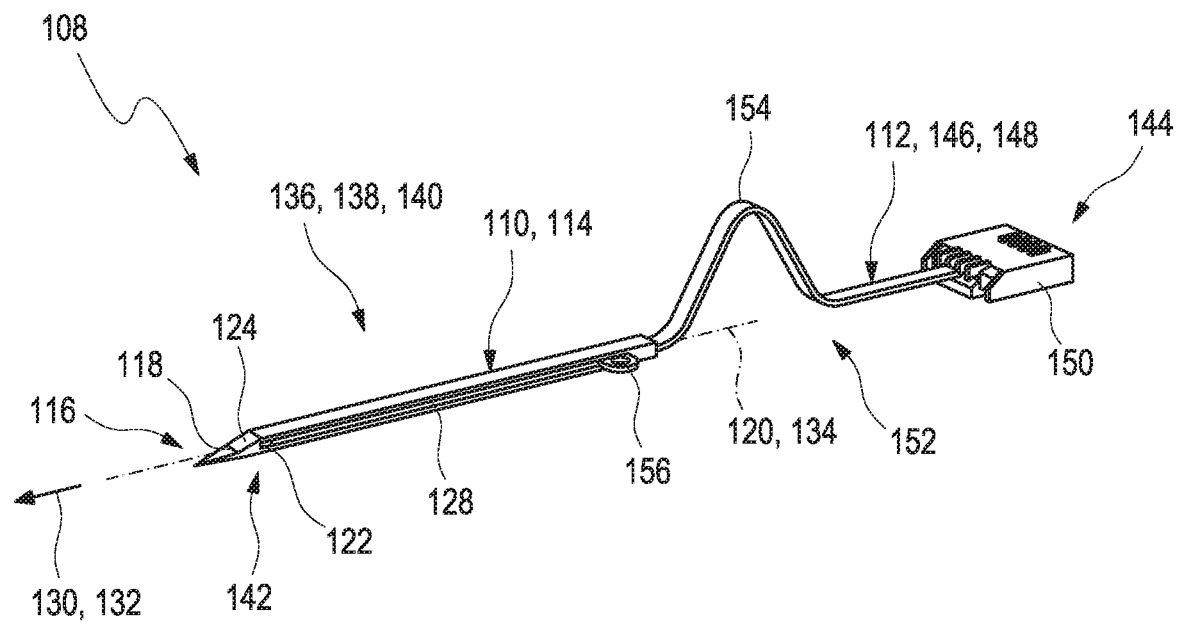
FIGS. 1A, 1B and 1C show an exemplary embodiment of a medical device in different perspective views.
Figure 1:
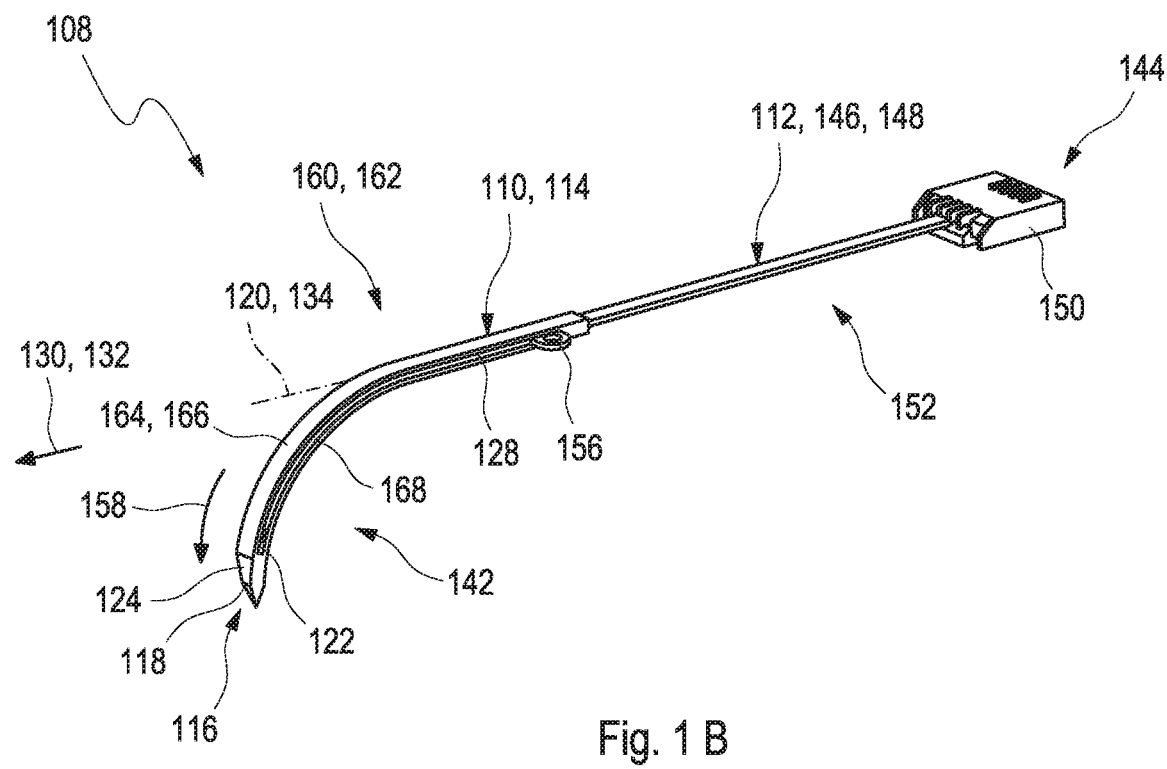
Figure 1:
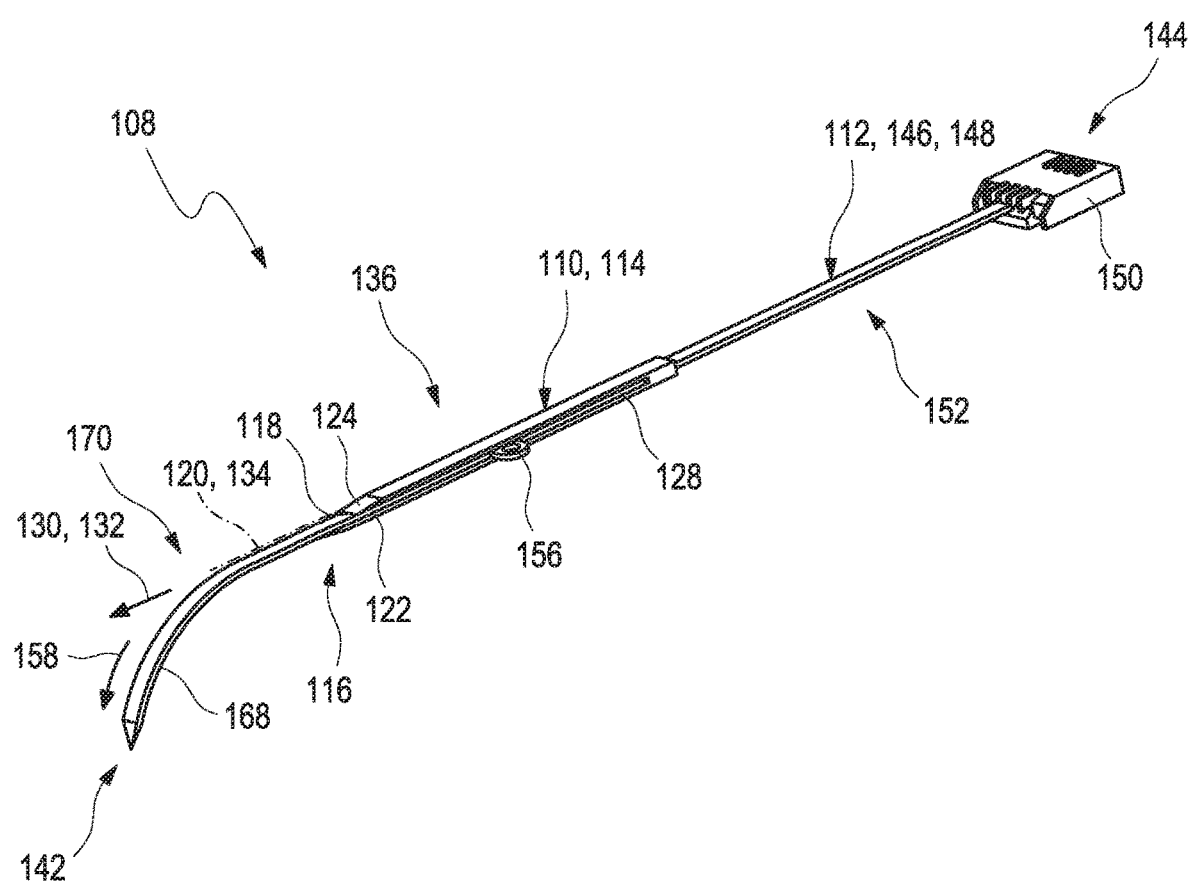

FIGS. 1A to 1C show an exemplary embodiment of a part of a medical device 108 in different perspective views. The medical device 108 further comprises at least one patch, which will be explained in an exemplary fashion in further details in the embodiments below. The medical device 108 comprises at least one pre-bended insertion cannula 110 and at least one insertable element 112. The pre-bended insertion cannula 110, in FIG. 1A, is shown in a flat shape, which is taken, e.g., due to external forces exerted onto the insertion cannula 110, as will be outlined in further detail below.

The insertion cannula 110 may specifically have an elongate shape. Further, the insertion cannula 110 may at least partially have an essentially rectangular shape, specifically a rectangular cross-section. Specifically, the insertion cannula 110 may be a slotted cannula 114. One end 116 of the insertion cannula 110 may comprise one slot 118 configured for facilitating an insertion of the insertion cannula 110 into a body tissue of a user or a patient. Specifically, the slot 118 may form an angle of to 10° to 80°, more preferably of 20° to 60°, to a longitudinal axis 120 of the insertion cannula 110, as depicted in FIG. 1A. Further, the slotted cannula 114 may have a slot 128 extending in an axial direction 130, specifically extending along the longitudinal axis 120 of the insertion cannula 110. The axial direction 130 may correspond to a direction of extension 132 of the insertion cannula 110. As will further be described below and as specifically depicted in FIGS. 1B and 1C, the insertion cannula 110 is transformable. Thus, the longitudinal axis 120 may be a major axis 134 and the insertion cannula 110 may be configured to be transformable along the major axis 134.

The insertion cannula 110 has a lumen 122 which is partially enclosed by a wall 124 of the insertion cannula 110. The wall 124 of the insertion cannula 110 specifically may comprise or may fully be made of stainless steel. The insertion cannula 110 is stored in a first configuration 136, as depicted in FIG. 1A. The first configuration 136 may correspond to an essentially straight shape 138 and/or to an essentially flat shape 140 of the insertion cannula 110. As will be outlined in further detail below, a rounded or curved shape is also possible.

The insertable element 112 comprises at least one in vivo distal end 142 and at least one ex vivo proximal end 144. The in vivo distal end 142 is configured for subcutaneous insertion. The insertable element 112 is at least partially received in the lumen 122 of the insertion cannula 110. Specifically, the in vivo distal end 142 may be received in the lumen 122 of the insertion cannula 110. The insertable element 112 may have an essentially elongate shape and may specifically have a cross-section which is adapted to the cross-section of the insertion cannula 110. Thus, the insertable element 112 may specifically have a rectangular cross-section. For example, the insertable element 112 may be a sensor 146, specifically an analyte sensor 148. The sensor 146 may be configured to be electrically connectable to an electronics unit (not shown). Thus, the sensor 146 may comprise a contact portion 150. The contact portion 150 may specifically be located at the ex vivo proximal end 144.

While the insertion cannula 110 is stored in the first configuration 136, as depicted in FIG. 1A, the shape of the insertable element 112 may correspond to the first configuration 136 of the insertion cannula 110. This first configuration may be taken when the insertion cannula 110 is in a storage position of a patch, as will be outlined in further detail below. Thus, the insertable element 112, specifically at least the in vivo distal end 142 of the insertable element 112, may be straight and extend along the major axis 134 of the insertion cannula 110 as well. Further, the insertable element 112 may comprise a middle part 152. The middle part 152 may refer to a part of the insertable element 112 located between the in vivo distal end 142 of the insertable element 112 and the ex vivo proximal end 144 of the insertable element 112. While the insertion cannula 110 is stored in the first configuration 136, the middle part 152 of the insertable element 112 may have a curved shape 154.

Further, the insertable element 112 may comprise at least one protrusion 156. The protrusion 156 may at least partially protrude through the slot 128. The protrusion 156 may be configured for preventing, at least to a large extent, a displacement of the insertable element 112 against a direction of insertion 158 of the insertion cannula 112. Specifically, the protrusion 156 may be configured to be movably fixed onto a surface (not shown), wherein the insertable element 112 is movable parallel to the surface.

As depicted in FIG. 1B, the insertion cannula 110 is configured to be transferred into a second configuration 160 for insertion. This second configuration may be taken by the cannula 110 in an inserted position within the body tissue, as will be outlined in further detail below. The second configuration 160 may correspond to a pre-programmed configuration 162. Thus, the insertion cannula 110 is a pre-bended insertion cannula 110, and the second configuration may be the natural bended configuration, whereas the first configuration may be a straight or less bended configuration into which the insertion cannula 110 has to be forced. Specifically, when the insertion cannula 110 is transformed to the second configuration 160, the insertion cannula 110 may comprise at least one curvature 164. More specifically, when in the second configuration 160, the insertion cannula 110 may have an arch form 166. Thereby, the insertion cannula 110, specifically the end 116 of the insertion cannula 110, may have an angle of 0° to 90°, specifically 30° to 50°, to the major axis 134.

The insertable element 112 may be made of a flexible material. Therefore, when the insertion cannula 110 is transformed into the second configuration 160, the insertable element 112 may be configured to adapt to the second configuration 160 of the insertion cannula 110. Thus, the insertable element 112, specifically the in vivo distal end 142 of the insertion cannula 110, may have an arch form 168 corresponding to the arch form 166 of the insertion cannula 110. Further, the middle part 152 of the insertable element 112 may be configured to elongate when the insertion cannula 110 is transformed into the second configuration 160. Specifically, both the first configuration 136 and the second configuration 160 may be bended configurations, with a bending radius in the first configuration 136 preferably being larger than a bending radius in the second configuration 160. As an example, the insertion cannula 110 may be a flexible pre-bended cannula, e.g. made of stainless steel, with a rectangular cross-section. In absence of external forces, the insertion cannula 110 may assume the second configuration 160, as depicted in FIG. 1B. By external forces, such as when forced into a housing of the medical device 108, the insertion cannula 110 may assume the first configuration 136, e.g. a more flat configuration, which is preferable for storing the insertion cannula 110 inside a housing, e.g., inside a patch, as will be outlined in further detail below. Still other embodiments, e.g., with the same radius of curvature in the storage position and in the inserted position are feasible.

As depicted in FIG. 1C, the insertion cannula 110 may be configured to be transformable from the second configuration 162 as depicted in FIG. 1B, back to the first configuration 136. Further, the insertable element 112 may be configured to retain a second configuration 170. Thus, the insertable element 112, specifically the in vivo distal end 142, may keep the arch form 168. Further, the middle part 152 may stay straight.

Figure 2:
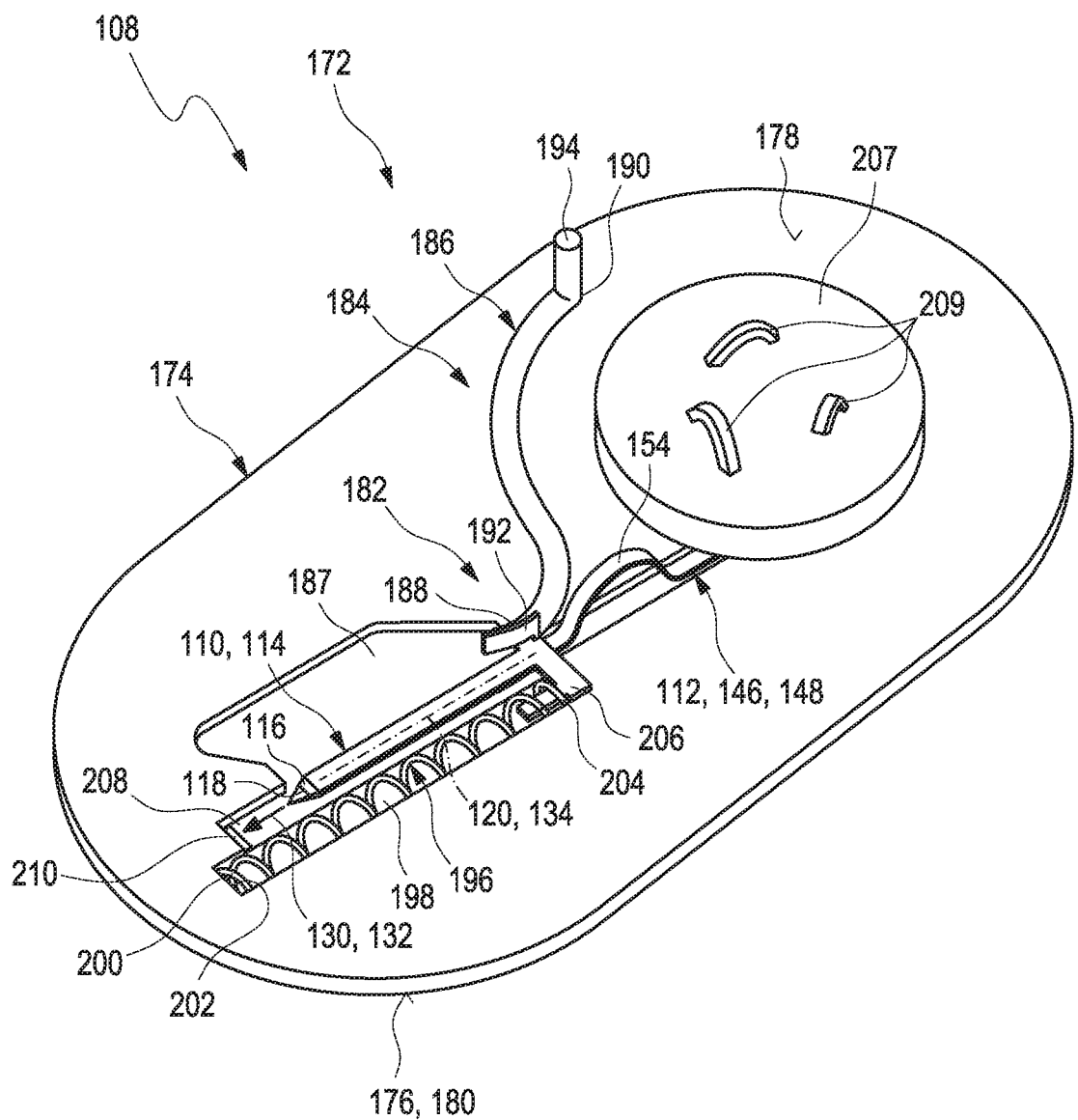
FIGS. 2A and 2B show exemplary embodiments of a medical device in different perspective views.
Figure 2:
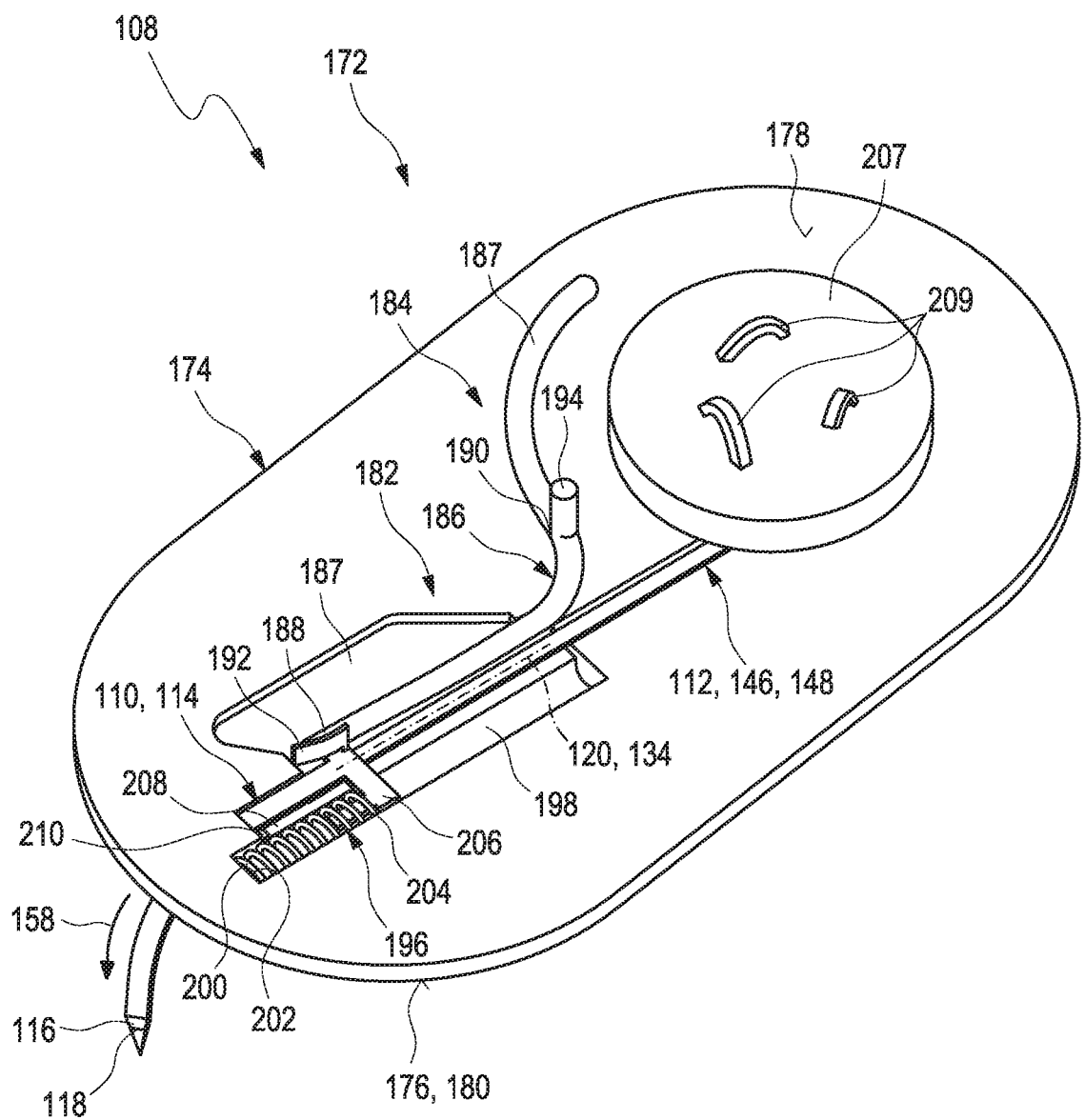

FIGS. 2A to 2B show exemplary embodiments of a medical device 108 in different perspective views. The medical device 108 comprises the insertion cannula 110 and the insertable element 112. The insertion cannula 110 and the insertable element 112 correspond, at least in large part, to the insertion cannula 110 and the insertable element 112 as illustrated in FIGS. 1A to 1C. Thus, reference may be made to the description of FIGS. 1A to 1C above.

As illustrated in FIG. 2A, the medical device 108 further comprises at least one patch 172 configured to be mounted onto the skin of a user (not shown). The patch 172 comprises a patch base 174. The patch base 174 may comprise a bottom side 176 and a front side 178. The insertion cannula 110 and the insertable element 112 may be located on the front side 178 of the patch 172. The bottom side 176 may specifically be or may comprise a flat surface 180. Thus, the patch 172 may be configured to be attachable to the skin of the user via the bottom side 176. For example, the bottom side 176 may comprise an adhesive surface, specifically a plaster (not shown).

The patch 172 comprises an integrated insertion mechanism 182 configured for driving the insertion cannula 110 from the first configuration 136, which is taken when the insertion cannula 110 is in a storage position within the patch 172 as shown in FIG. 2A, into the second configuration 160, which is taken when the insertion cannula 110 is in an inserted position as shown in FIG. 2B, extending into a body tissue. The integrated insertion mechanism 182, when driving the insertion cannula 110 from the storage position into the inserted position, moves the insertion cannula 110 on an insertion path, which is a curved insertion path. As an example, a tip of the insertion cannula 110 may move along a curved insertion path. The integrated insertion mechanism 182 may be located on the front side 178 of the patch 172.

The integrated insertion mechanism 182 may comprise at least one drive unit 184. The drive unit 184 may be configured to urge the insertion cannula 110 in the direction of insertion 158. The drive unit 184 may comprise at least one flexible wire 186 configured for driving an insertion of the insertable element 112. The flexible wire 186 may be received in a receptacle 187 of the patch 172. The flexible wire 186 may comprise a first end 188 and a second end 190. The first end 188 may be configured to be attachable to the insertion cannula 110. Therefore, the flexible wire 186, specifically the first end 188, may comprise a bearing area 192 for the insertion cannula 110. Further, the integrated insertion mechanism 182 may comprise at least one pin 194. The pin 194 may be attached to the second end 190 of the flexible wire 186. The pin 194 may be engageable and/or driven by at least one element (not shown) connected or connectable to the patch base 174. Thereby, the integrated insertion mechanism 182 may be configured to be driven by a connecting force exerted via the pin 194 when connecting the element to the patch base 174. Specifically, the drive unit 184 may be triggered or driven via a rotational mechanism. Therefore, the flexible wire 186 may have a curved shape.

The integrated insertion mechanism 182 may further comprise at least one return spring 196. The return spring 196 may be configured to support a withdrawing of the insertion cannula 110 from the body tissue after insertion. The return spring 196 may be located in a receptacle 198 of the patch base 174. The return spring 196 may comprise a first end 200. The first end 200 may be attachable to a side wall 202 of the receptacle 198. Further, the return spring 196 may comprise a second end 204. The second end 204 may be connectable to the insertion cannula 110, specifically via a protrusion 206 of the insertion cannula 110.

The insertion cannula 110 may be received in a further receptacle 208. The further receptacle 208 may be located parallel to the receptacle 198 of the return spring 196. The insertion cannula 110 may be configured to be movable within the further receptacle 208. The insertion cannula 110 may be stored in the first configuration 136 inside the patch 172, as described in FIG. 1A.

The medical device 108, specifically the patch 172, may comprise a circuit board 207 comprising electrical contacts 209. The electrical contacts 209 may be configured to be electrically connectable to at least one element interacting with the insertable element 112.

As illustrated in FIG. 2B, the insertion cannula 110, when being transformed into the second configuration 160, may at least partially be located outside of the patch 172. Specifically, the insertion cannula 110 may protrude from the patch 172. Therefore, the patch 172 may comprise at least one passage opening 210. The insertion cannula 110 may be movable from the patch 172 into the body tissue (not shown) through the passage opening 210 and vice versa. For further details on the second configuration 160 of the insertion cannula 110, reference may be made to FIG. 1B.

The insertion cannula 110 may be configured to be movable along the major axis 134 and within the further receptacle 208 via the integrated insertion mechanism 182. Further, the insertion cannula 110 may be configured to be transformable into the second configuration 160 when the insertion cannula 110 passes the passage opening 210. The further receptacle 208 may further be configured to receive the insertable element 112, specifically when the insertable element 112 is in the flat shape 140.

Figure 3:
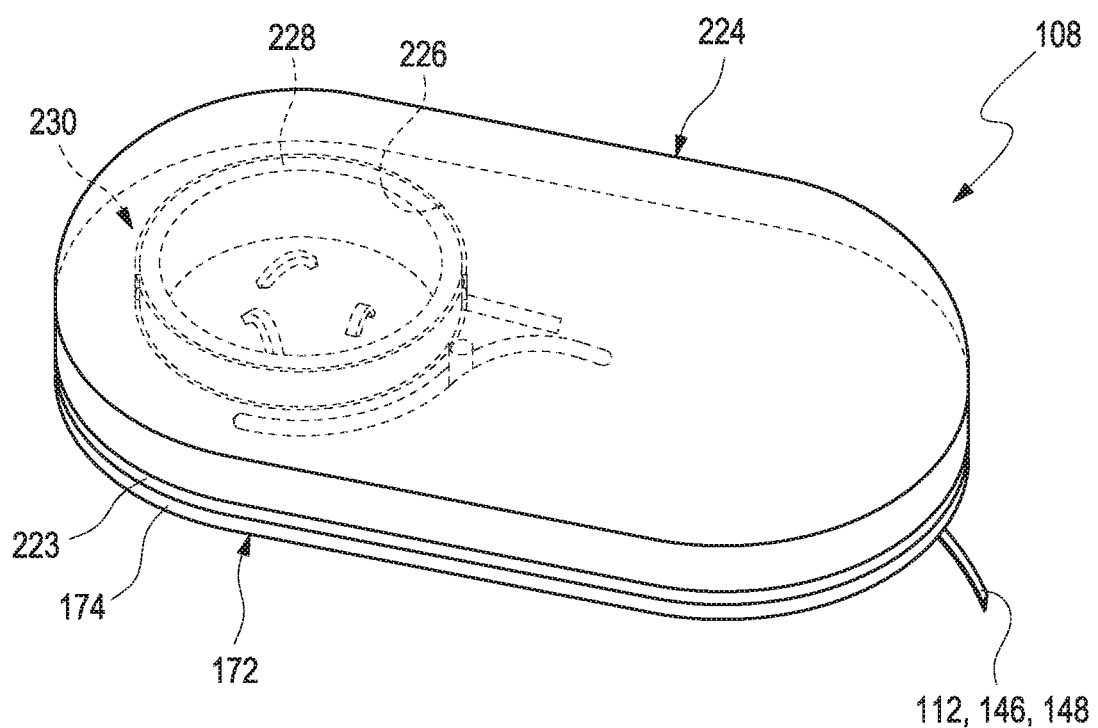
FIG. 3 shows an exemplary embodiment of a medical device in a perspective view.
Figure 4:
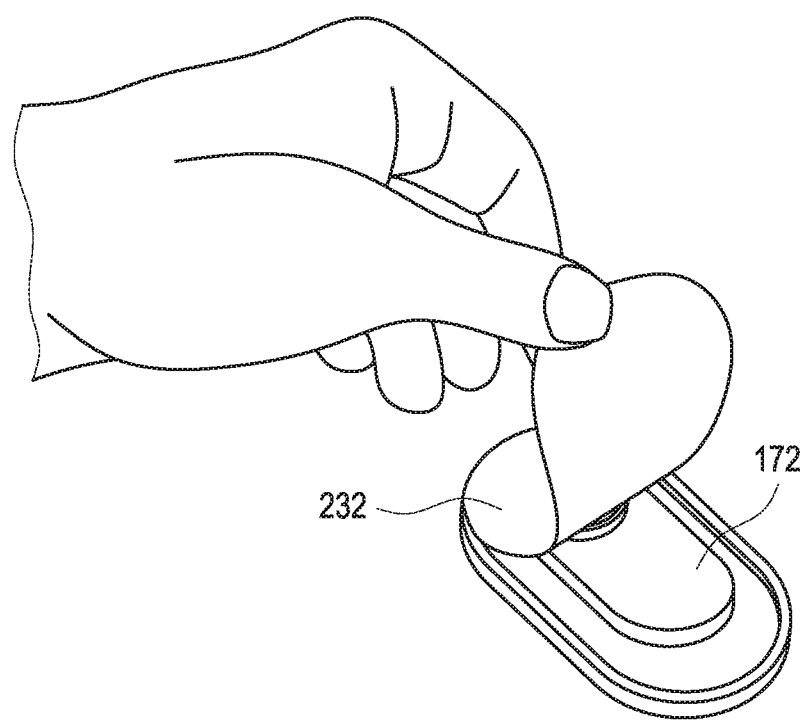
FIGS. 4A, 4B, 4C and 4D show an exemplary method for transcutaneously inserting an insertable element into a body tissue.

FIG. 3 shows a further exemplary embodiment of a medical device 108 in a perspective view. The medical device 108 comprises the insertion cannula 110, the insertable element 112 and the patch 172 (not shown). The insertion cannula 110, the insertable element 112 and the patch 172 may correspond, at least in large part, to the insertion cannula 110, the insertable element 112 and the patch 172, as illustrated in FIGS. 1A to 2B. Thus, reference may be made to FIGS. 1A to 2B above.

The patch 172 comprises the patch base 174 and at least one patch cover element 223. The patch cover element 223 may be configured to cover the insertion mechanism 182, at least partially. The medical device 108 may further comprise at least one electronics unit 224 configured for interacting with the insertable element 112. The electronics unit 224 may comprise at least one electronics unit bayonet screw 226. The patch 172 may comprise at least one patch bayonet contour 228. The patch bayonet contour 228 and the electronics unit bayonet screw 226, in conjunction, may form a bayonet connector 230 configured for establishing a releasable mechanical connection between the electronics unit 224 and the patch 172. In FIG. 3, the medical device 108 is shown in a mated state in which the releasable mechanical connection between the electronics unit 224 and the patch 172 is established by the bayonet connector 230. Thereby, the electronics unit 224 may be pressed onto the patch 172 or vice versa, by means of the bayonet connector 230.

FIGS. 4A to 4D show an exemplary method for transcutaneously inserting an insertable element 112 into a body tissue. The medical device 108 as illustrated within FIGS. 4A to 4D may correspond, at least in large part, to the medical devices 108 as illustrated in FIGS. 1A to 3. Thus, reference may be made to the description of FIGS. 1A to 3 above.

In a first step, as illustrated in FIG. 4A, the patch 172 is provided in a sterile packaging 232. The sterile packaging may be opened and the electronics unit 224 may be attached to the patch 172, as illustrated in FIG. 4B. Specifically, the electronics unit 224 may be attached to the patch 172 by placing the electronics unit bayonet screw 226 into the patch bayonet contour 228 forming a bayonet connector 230, as illustrated in FIG. 3.

In a further step, as illustrated in FIG. 4C, the patch 172 with the electronics unit 224 attached to the patch 172 may be placed onto the skin 234 of the user 236. Specifically, the patch 172 may be attached to the skin 234 via the bottom side 176 of the patch 172. The bottom side 176 may provide an adhesive surface 238.

Further, as illustrated in FIG. 4D, the insertable element 112 (not shown in FIG. 4D) may be inserted into the body tissue 240. The user 236 may trigger the rotational mechanism as described within FIGS. 2A to 2B via a rotational movement of the electronics unit 224.

Figure 5A:
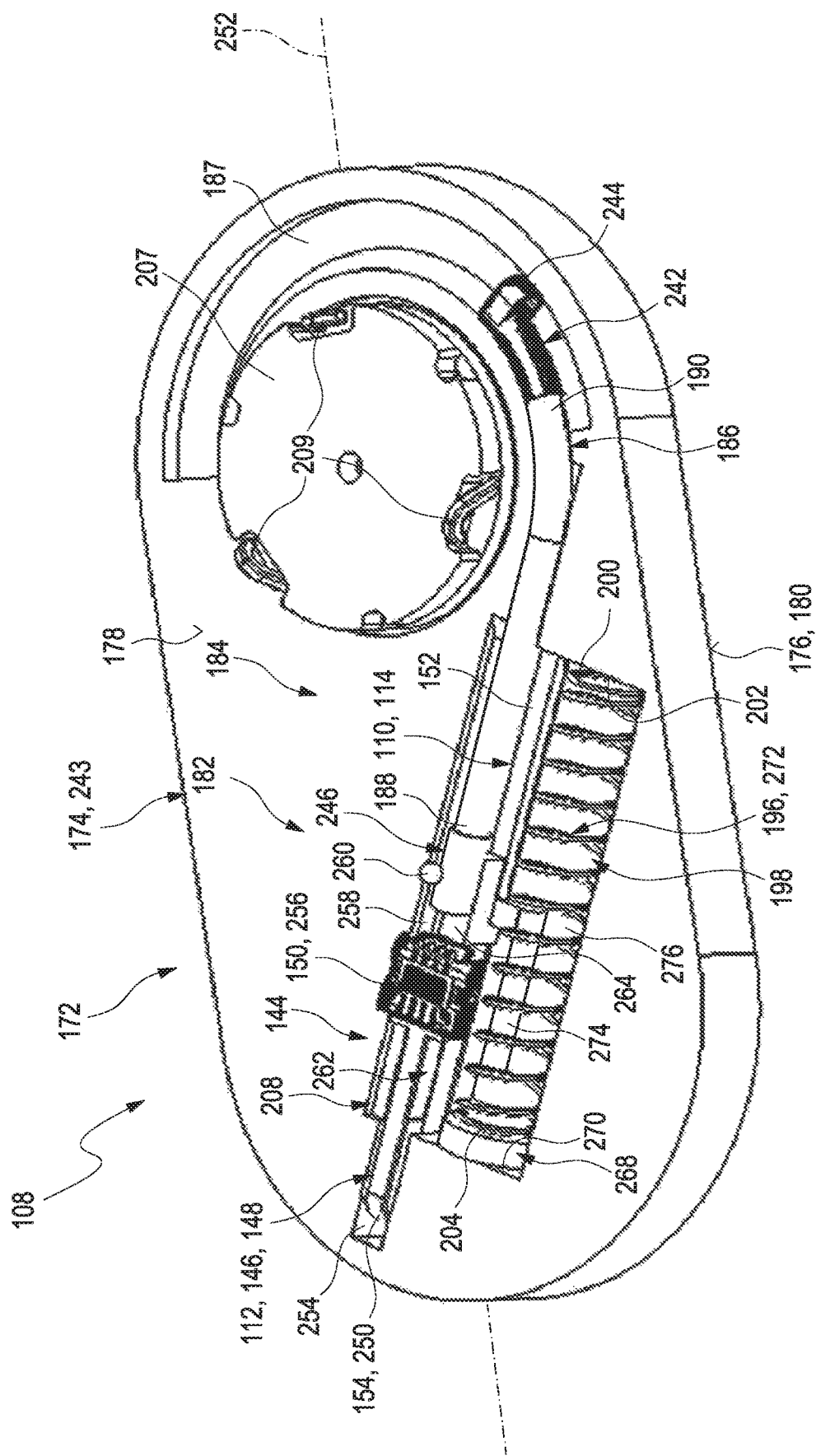
FIGS. 5A, 5B, 5C, 5D, 5E, 5F and 5G show a further exemplary embodiment of a medical device in perspective views (FIGS. 5A, 5C, 5E), in cross-sectional views (FIGS. 5B, 5D, 5F) and in an enlarged sectional view (FIG. 5G)

FIGS. 5A to 5G show a further exemplary embodiment of a medical device 108 in perspective views (FIGS. 5A, 5C, 5E), in cross-sectional views (FIGS. 5B, 5D, 5F) and in an enlarged sectional view (FIG. 5G). The medical device 108 corresponds partially to the medical device 108 as illustrated in FIGS. 2A to 2B. Thus, reference may be made to the description of FIGS. 2A to 2B above. Specifically, the medical device 108 as illustrated in FIGS. 5A to 5G may provide an arrangement wherein the insertable element 112 is situated further away from the insertion cannula 110 in comparison to the arrangement of the medical device 108 as illustrated in FIGS. 2A to 2B.

The medical device 108 comprises the insertion cannula 110 and the insertable element 112. Further, the medical device 108 comprises the patch 172 configured to be mounted onto the skin of the user (not shown). The patch 172 comprises the patch base 174 and, optionally, a patch base cover element 243. Moreover, the patch 172 comprises the integrated insertion mechanism 182. The medical device 108, specifically the patch 172, may further comprise the circuit board 207 comprising the electrical contacts 209.

The integrated insertion mechanism 182 may comprise the drive unit 184. The drive unit 184 may comprise the flexible wire 186. The second end 190 of the flexible wire 186 may be received in a sleeve 242. At least parts of the flexible wire 186 and the sleeve 242 may be received in the receptacle 187 of the patch 172. The receptacle 187 may comprise a curved shape. The sleeve 242 may comprise a protrusion 244, which can also be denoted as protrusion flexible wire. The protrusion 244 may be configured such that a movement of the flexible wire 186 may be triggered by at least one element (not shown) connectable to the patch 172. Specifically, the movement of the flexible wire 186 may be triggered by a force exerted via the sleeve 242. The drive unit 184 may be triggered via a rotational mechanism.

Figure 5B:
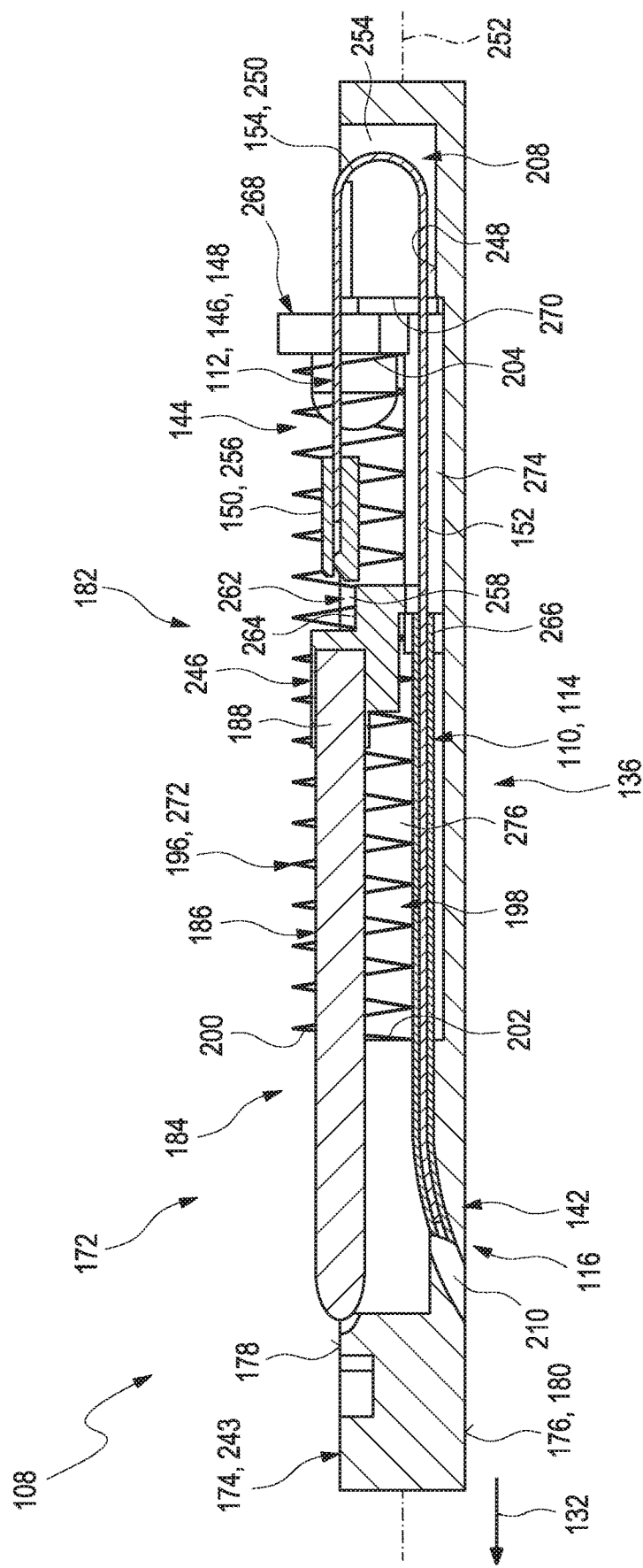

In FIGS. 5A and 5B, the insertion cannula 110 is in a storage position within the patch 172 and may be transformed into the first configuration 136. The insertion cannula 110 and the insertable element 112 may be at least partially received in the further receptacle 208. Thereby, the insertion cannula 110 may lie flat onto a surface 248 of the further receptacle 208. The insertable element 112 may at least partially be received within the insertion cannula 110. Specifically, the in vivo distal end 142 of the insertable element 112 may be received within the insertion cannula 110. Further, the insertable element 112 may be received in the further receptacle 208 in a two-layered fashion. The in vivo distal end 142 may be received in the insertion cannula 110 which may lie flat onto the surface 248 of the further receptacle 208, wherein the ex vivo proximal end 144 may be situated opposite to the in vivo distal end 142 and may extend parallel to the in vivo distal end 142 in a certain distance to the in vivo distal end 142. Thus, the middle part 152 of the insertable element 112 may be in the curved shape 154. A bend 250 of the insertable element 112 may extend in a direction perpendicular to a longitudinal axis 252 of the patch 172. Specifically, the bend 150 may be located in an end section 254 of the further receptacle 208.

Further, the contact portion 150, specifically at least one zero insertion force ("ZIF") connector 256, may be attached to the insertable element 112 for providing an electrical connection to the insertable element 112. The ZIF connector 256 may be located in a middle section 258 of the further receptacle 208. Specifically, the ZIF connector 256 may be fixedly attached to the patch 172, specifically to the patch base cover element 243.

The first end 188 of the flexible wire 186 may be received in a further sleeve 246. The further 246 sleeve may comprise at least one first further sleeve protrusion 260. The first further sleeve protrusion 260 may lie on a patch base cover element receptacle 262 of the patch base cover element 243. The patch base cover element receptacle 262 may extend parallel to the direction of extension 132 of the insertion cannula 110 and may have a straight, elongate shape. Thus, the further sleeve 246 may be configured to be moveable along the direction of the extension 132 of the insertion cannula 110, the first further sleeve protrusion 260 thereby moving within the patch base cover element receptacle 262. Further, the further sleeve 246 may have a second further sleeve protrusion 264. The second further sleeve protrusion 264 may be attached to one end 266 of the insertion cannula 110. Thus, the insertion cannula 110 may be configured to be triggered by moving the flexible wire 186. In case the insertion cannula 110 is transformed into the first configuration 136 as illustrated in FIGS. 5A and 5B, the further sleeve 246 may be located in the middle section 258 of the further receptacle 208.

Further, the integrated insertion mechanism 182 may comprise the return spring 196. The return spring 196 may be configured to support a withdrawing of the insertion cannula 110 from the body tissue (not shown) after insertion. The return spring 196 may be located in the receptacle 198. The first end 200 of the return spring 196 may be attached to the side wall 202 of the receptacle 198. The second end 204 of the return spring may be fixedly attached to a cannula sleeve 268. When the insertion cannula 110 is transformed into the first configuration 136, as illustrated in FIGS. 5A and 5B, the cannula sleeve 268 may be attached to a further side wall 270 of the receptacle 198 opposing the side wall 202 of the receptacle 198. Thereby, the return spring 196 may be in an outstretched configuration 272. Moreover, the cannula sleeve 268 may comprise an arm 174. The arm 174 may extend along the direction of extension 132 of the insertion cannula 110 and may form a fixed connection between the cannula sleeve 268 and the insertion cannula 110. The further receptacle 208 may be located parallel to the receptacle 198 of the return spring 196.

Figure 5C:
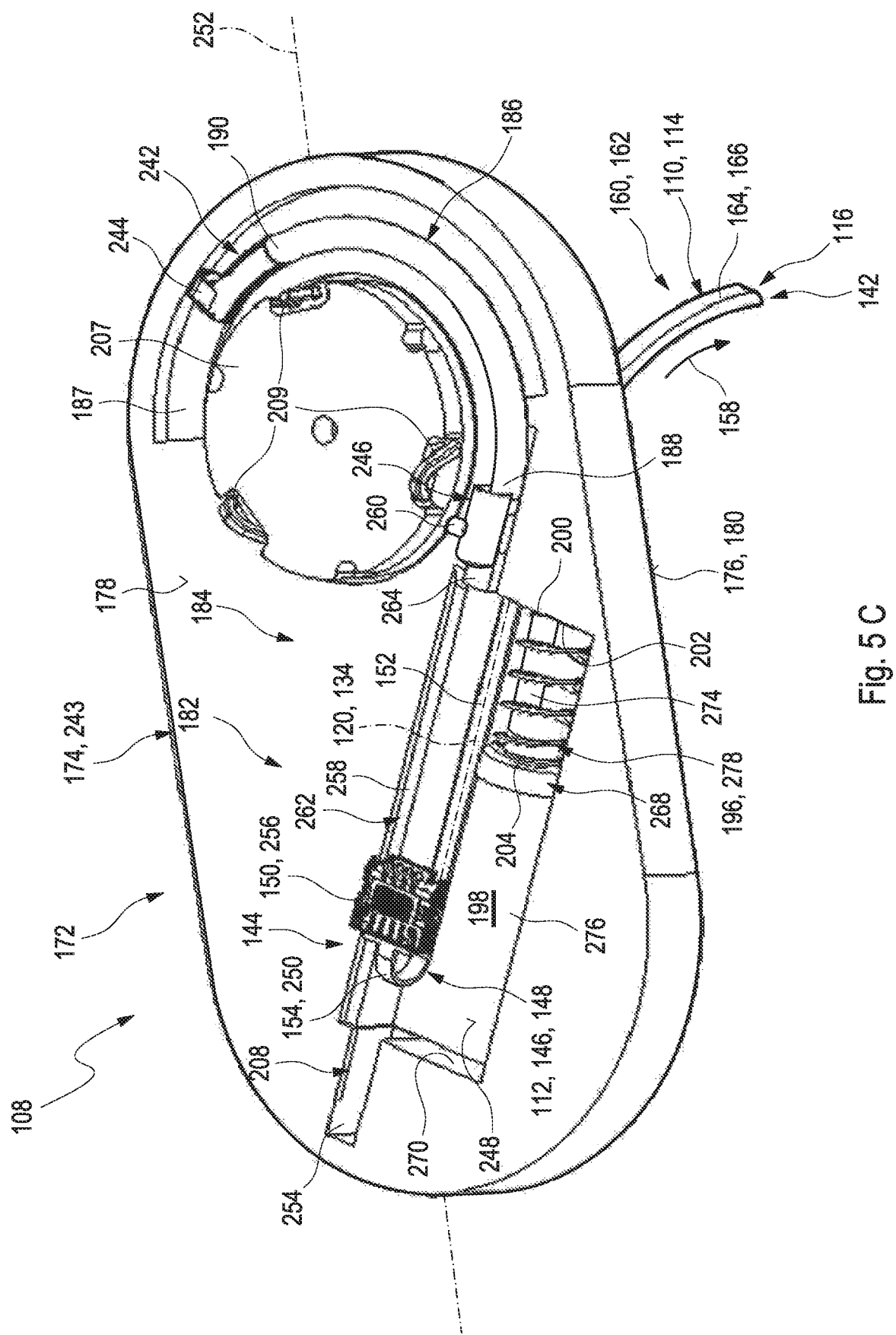
Figure 5D:
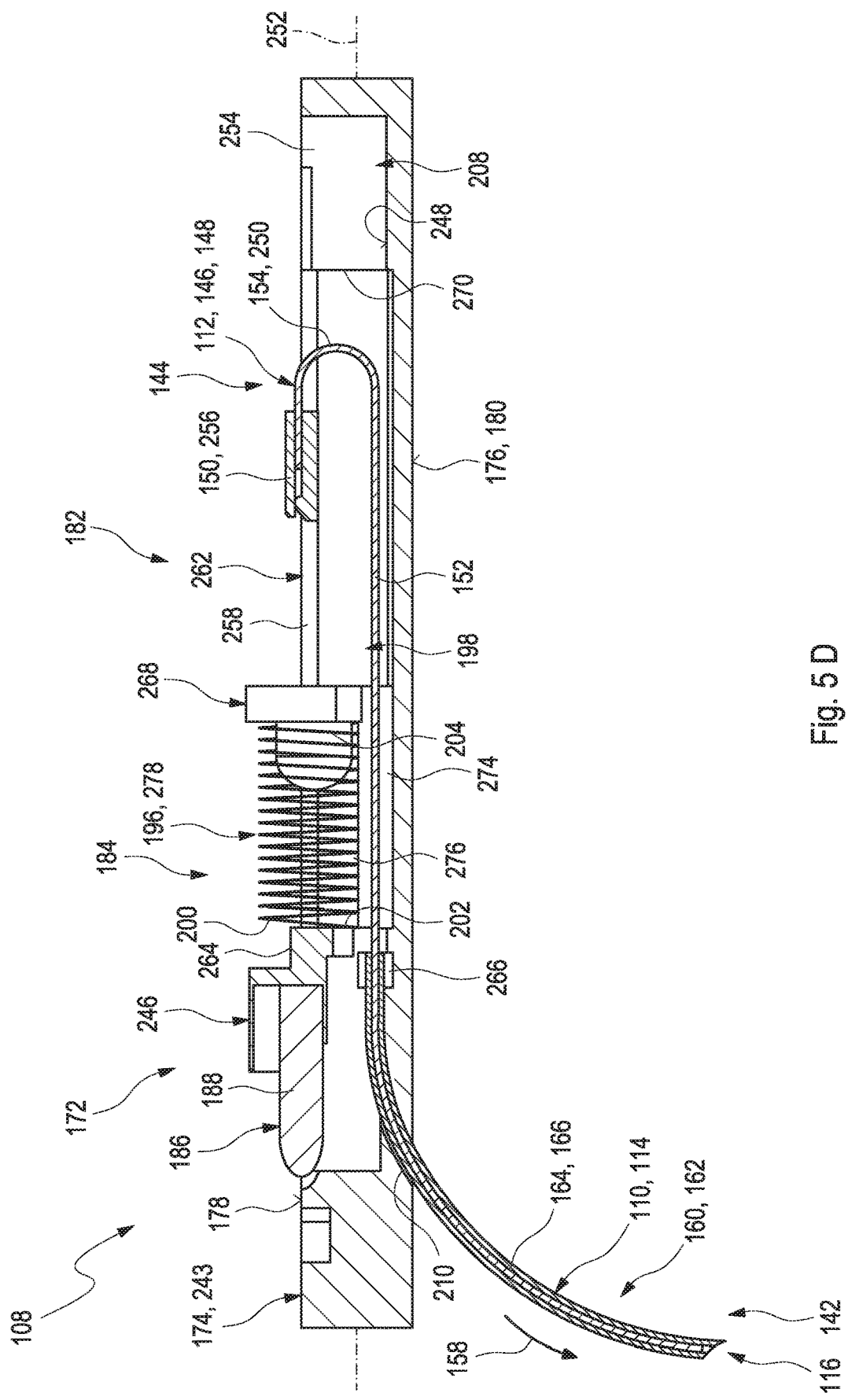
Figure 5:
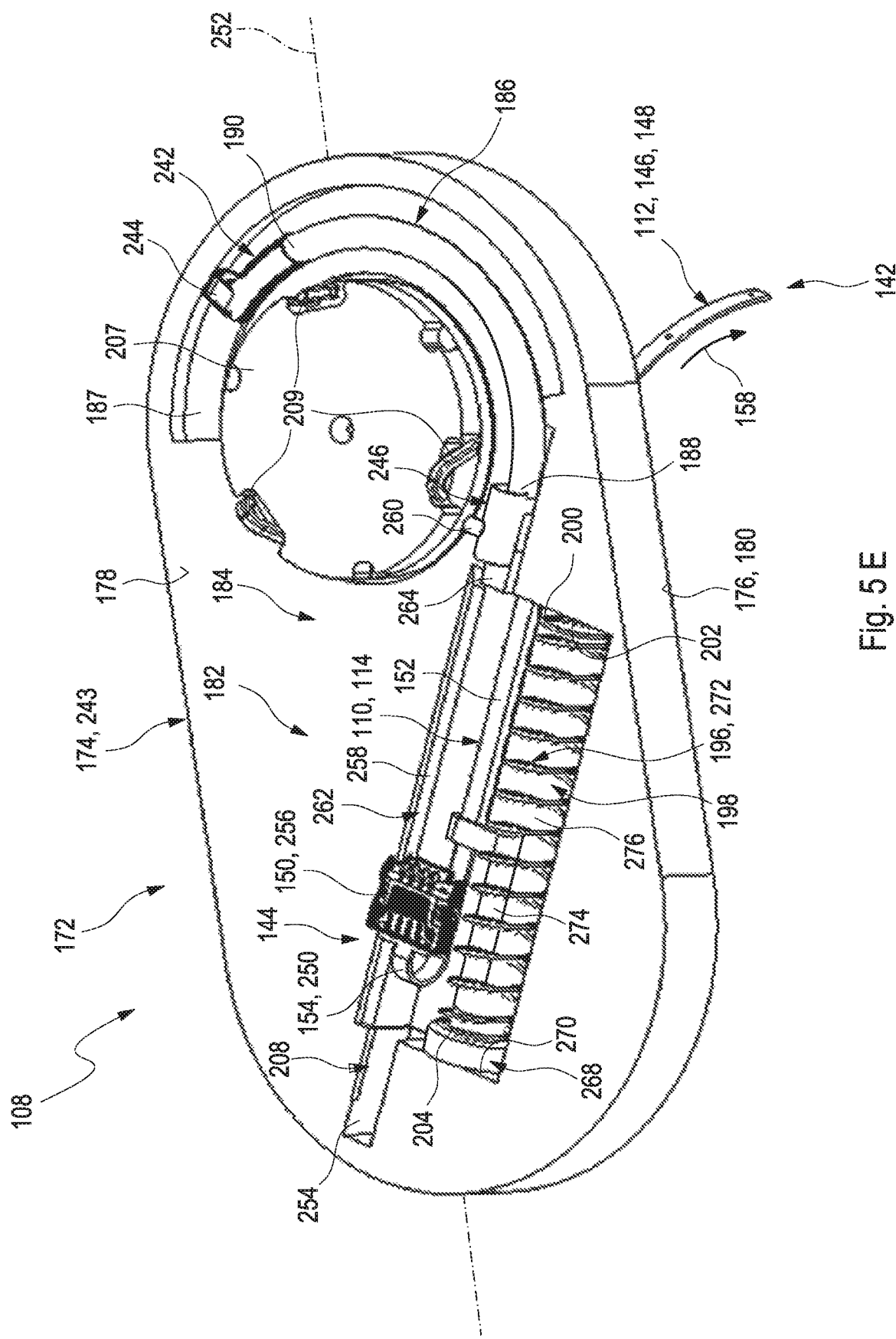

In FIGS. 5C, 5D, 5E and 5F, the insertion cannula is shown in an inserted position, taking the second configuration 160. As illustrated in FIGS. 5C and 5D, the insertion cannula 110, when being transformed into the second configuration 160, may at least partially be located outside of the patch 172. Thereby, the flexible wire 186 may be fully, or at least to a large extent, received in the receptacle 187. In this manner, the cannula sleeve 268 may also be received in the receptacle 187. Further, the cannula sleeve 268 may be located in a middle section 276 of the receptacle 198 and the return spring 196 may be in a tensioned configuration 278.

As the insertable element 112 may be at least partially located outside of the patch 172, accordingly, the ex vivo proximal end 144 of the insertable element 112 may be located in the middle section 258 of the further receptacle 208. Thus, the bend 250 of the insertable element 112 may be located in the middle section 258 accordingly.

Figure 5F:
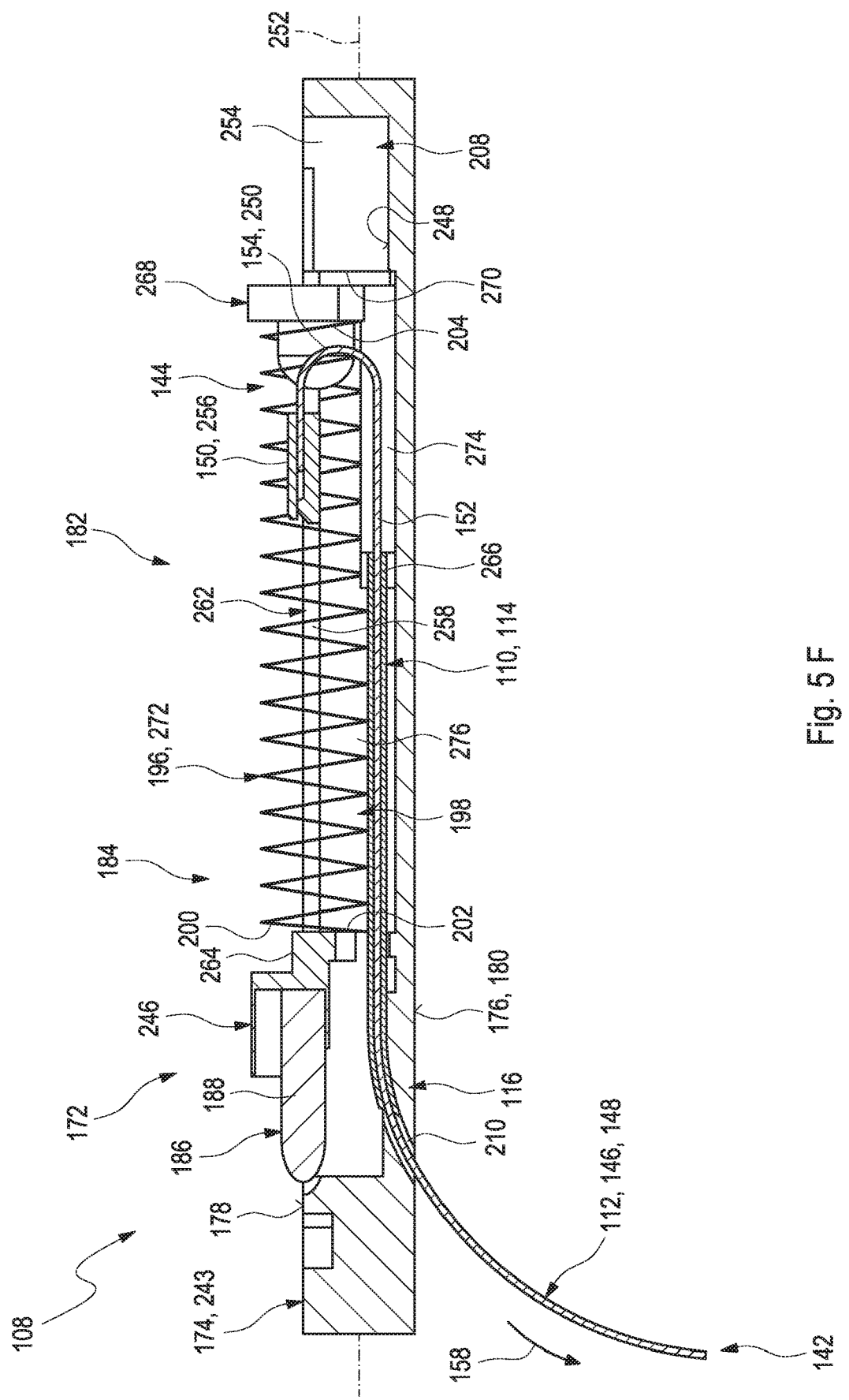
Figure 5:
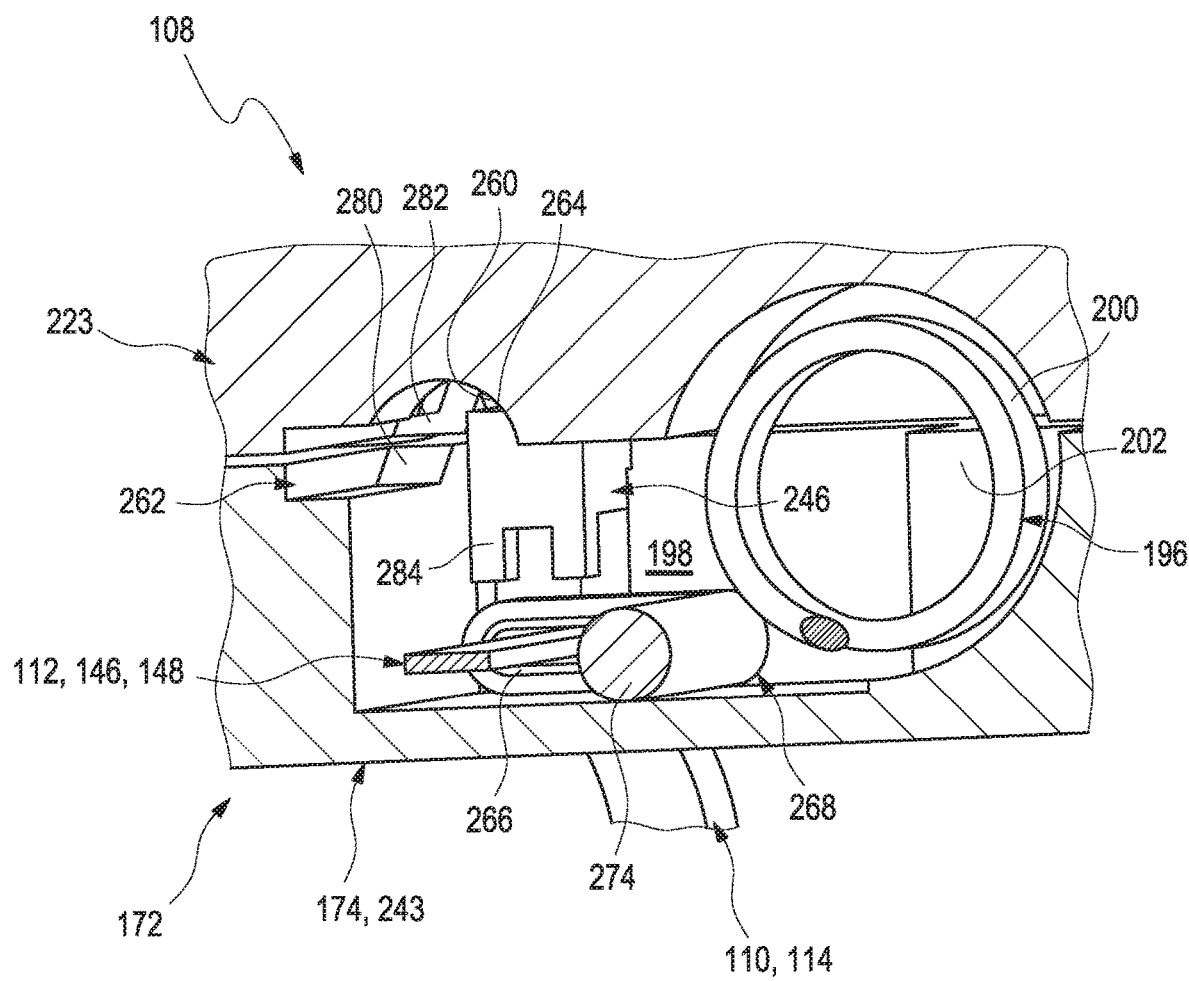

As illustrated in FIGS. 5E and 5F, the insertable element 112 may be configured to stay outside of the patch 172 when insertion cannula 110 is withdrawn into the patch 172. The return spring 196 may be in the outstretched configuration 272 and the cannula sleeve 268 may be attached to the further side wall 270 of the receptacle 198.

In FIG. 5G, an enlarged sectional view of the medical device 108 is shown. Specifically, parts of the receptacle 198 and of the further receptacle 208 are illustrated. The further sleeve 246, specifically the first further sleeve protrusion 260, may be configured to be lifted from the patch base cover element receptacle 262 before the insertion cannula 110 is withdrawn into the patch 172. Therefore, the patch base cover element receptacle 262 may have a ramp 280. Specifically, the first further sleeve protrusion 260 may be configured to be lifted beyond a hook 282 of the patch cover element 223. The second further sleeve protrusion may comprise a second further sleeve protrusion receptacle 284. The second further sleeve protrusion receptacle 284 may be configured to enclose the insertable element 112 at least partially to attach to the insertion cannula 110, specifically to the end 266 of the insertion cannula 110. Thus, the ramp 280 may be configured to disconnect the second further sleeve protrusion receptacle 284 from the insertion cannula 110 such that, afterwards, the insertion cannula 110 may be withdrawn into the patch 172 such as illustrated in FIGS. 5E and 5F.

Figure 6:
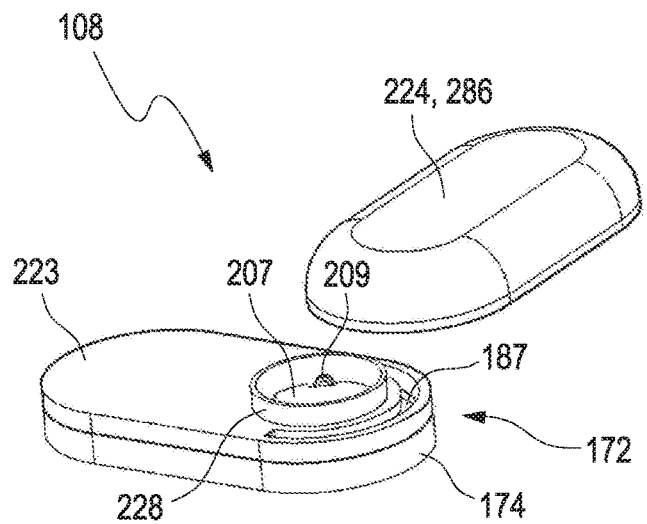
FIGS. 6A, 6B and 6C show a further exemplary method for transcutaneously inserting an insertable element into a body tissue.
Figure 6:
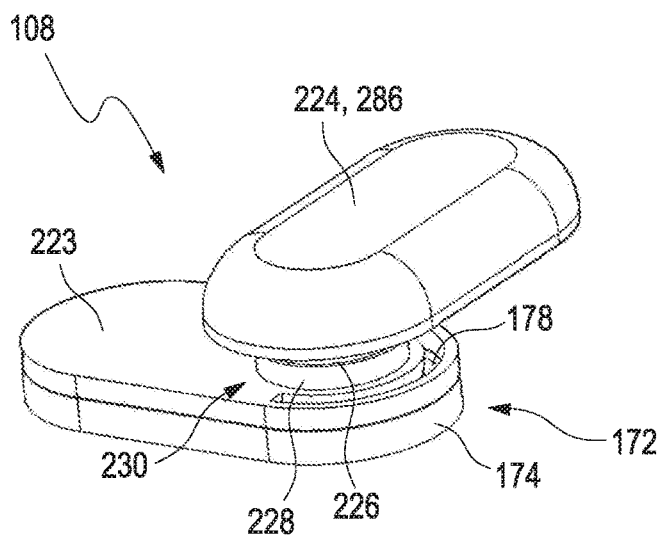
Figure 6:
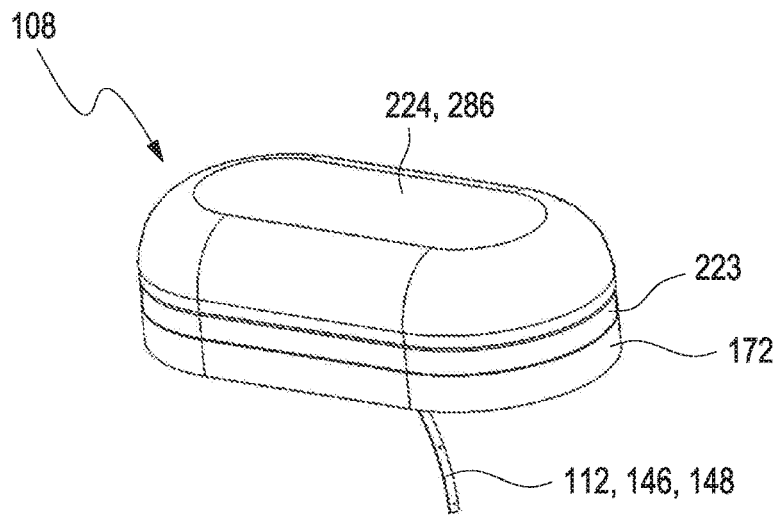

FIGS. 6A to 6C show a further exemplary method for transcutaneously inserting an insertable element 112 into a body tissue. The method as illustrated within FIGS. 6A to 6C corresponds, at least in large part, to the method as illustrated within FIGS. 4A to 4D. Further, the medical device 108 as illustrated within FIGS. 6A to 6C corresponds, at least in large part, to the medical device as illustrated in FIGS. 5A to 5G. Thus, reference can be made to the descriptions of FIGS. 4A to 4D and of FIGS. 5A to 5G above.

Firstly, as illustrated in FIG. 6A, the patch 172 and the electronics unit 224 may be provided. The electronics unit 224 may specifically be provided as a separate component 286. Further, as illustrated in FIG. 6B, the electronics unit 223 may be attached to the patch 172, specifically to the patch cover element 223, by placing the electronics unit bayonet screw 226 into the patch bayonet contour 228, forming the bayonet connector 230. In a further step, as depicted in FIG. 6C, the insertable element 112 may be inserted into the body tissue (not shown). Therefore, the rotational movement of the electronics unit 224 may trigger the rotational mechanism.

Figure 7:
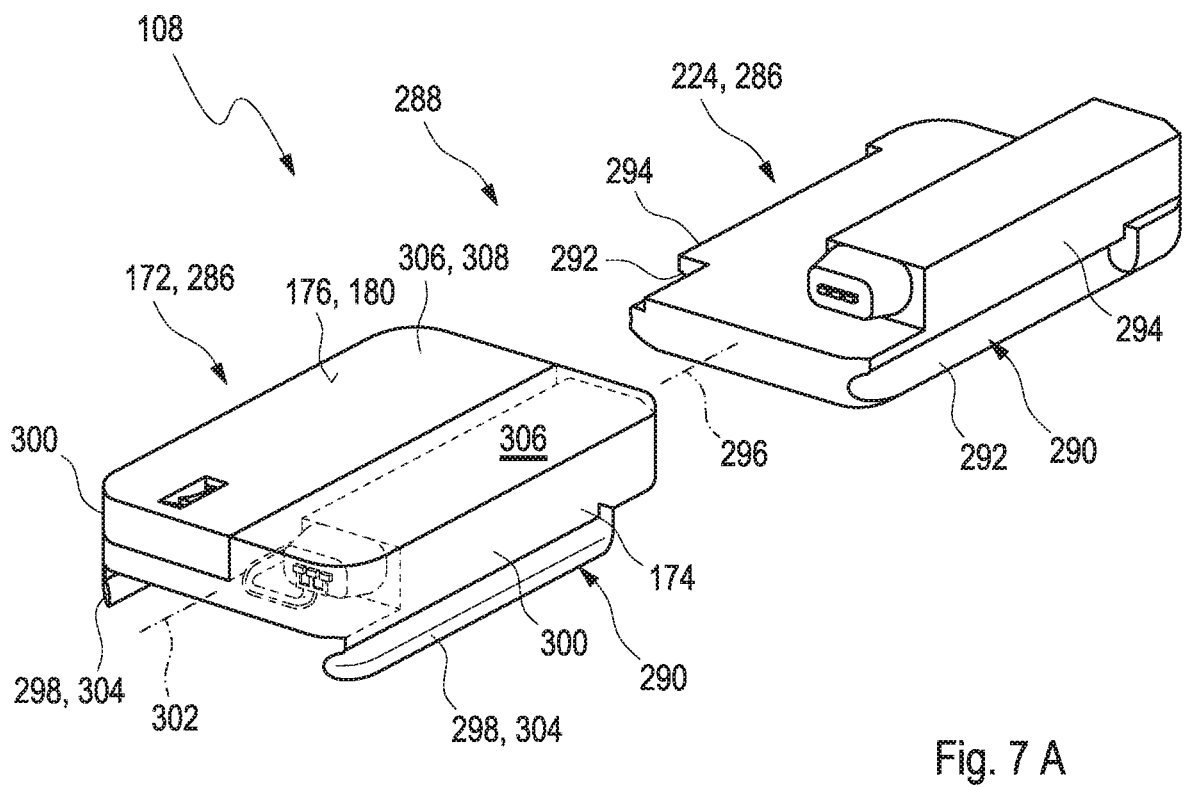
FIGS. 7A and 7B show a further exemplary embodiment of a medical device in different perspective views.
Figure 7:
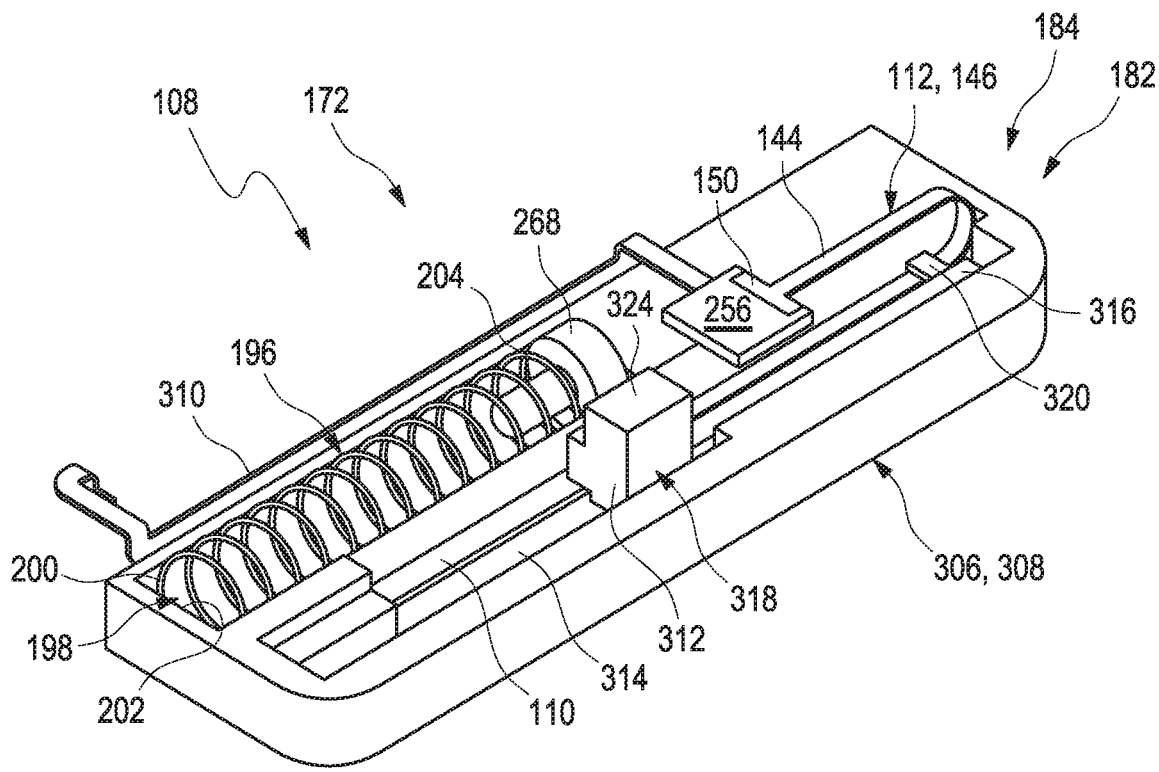

FIGS. 7A and 7B show a further exemplary embodiment of a medical device 108 in different perspective views. The medical device 108 as depicted in FIGS. 7A and 7B corresponds, at least in large part, to the medical device 108 as illustrated in FIGS. 1A to 6C. Thus, reference may be made to the descriptions of FIGS. 1A to 6C above.

The medical device 108 as depicted in FIG. 7A is shown in an initial state 288, wherein the electronics unit 224 and the patch 172 are provided as separate components 286. The patch 172 may comprise the patch base 174. The patch base 174 may comprise the bottom side 176, which may specifically be, or may comprise, the flat surface 180. Thus, the patch 172 may be configured to be attachable to the skin, of the user via the bottom side 176. For example, the bottom side 176 may comprise an adhesive surface, specifically a plaster (not shown).

The medical device 108, specifically the integrated insertion mechanism 182, may comprise a linear sliding mechanism 290. Specifically, the electronics unit 224 may comprise two linear sliding receptacles 292. The linear sliding receptacles 292 may be located on longitudinal sides 294 of the electronics unit 224, respectively. Further, the linear sliding receptacles 292 may have an elongate shape and may extend along a longitudinal axis 296 of the electronics unit 224. Specifically, the linear sliding receptacles 292 may have a straight shape. Complementary to the linear sliding receptacles 292, the patch 172 may comprise at least two linear sliding guide rails 298. The linear sliding guide rails 298 may be located on longitudinal sides 300 of the patch 172. The linear sliding guide rails 298 may extend along a longitudinal axis 302 of the patch 172. Further, the linear sliding guide rails 298 may have a straight shape. Specifically, the linear sliding guide rails 298 may be formed as a protrusion 304 of the patch 172.

Specifically, the linear sliding guide rails 298 of the patch 172 and the linear sliding receptacle 292 may be shaped complementary to each other. The linear sliding receptacle 292 may be configured to receive the linear sliding guide rails 298. Thus, the linear sliding guide rails 298 may have a shape and a size which correspond to the linear sliding receptacles 292. For example, the linear sliding guide rails 298 may have a round shape and the linear sliding receptacle 292 may have a round shape, too. Consequently, the electronics unit 224 may be mountable onto the patch 172 via the linear sliding receptacle 292, as will further be described below in more detail.

Specifically, the patch 172 may be made of two parts 306. One of the two parts 306 may be formed as a functional module 308 housing the integrated insertion mechanism 182, the insertable element 112 and the insertion cannula 110. The functional module 308 may be fixedly attached to the other one of the parts 306.

Within this exemplary embodiment, the insertable element 112 may specifically be the sensor 146 having the contact portion 150 which may specifically be located at the ex vivo proximal end 144 of the sensor 146. The ZIF connector 256 may be attached to the insertable element 112 for providing an electrical connection between the electronics unit 224 and the insertable element 112. Therefore, the ZIF connector 256 may be operably connected to electrical contacts 310. Further, the integrated insertion mechanism 182 may comprise the return spring 196. The return spring 196 may be configured to support a withdrawing of the insertion cannula 110 from the body tissue after insertion, as will further be described below in more detail. Specifically, the return spring 196 may be located in the receptacle 198 of the patch 172. The return spring 176 may comprise the first end 200, which may be attachable to the side walls 202 of the receptacle 198. Further, the return spring 196 may comprise the second end 204. The second end 204 may be fixedly attached to the cannula sleeve 268. A drive arm 312 which may be part of the drive unit 184 may be configured to be moved linearly on the patch 172, specifically on the functional module 308. Therefore, the patch 172, specifically the functional module 308, may have a drive arm receptacle 314 which is configured such that the drive arm 312 is linearly movable on the patch 172. One end 316 of the drive arm 312, opposing an end 318 of the drive arm 312, which is fixedly attached to the cannula sleeve 268, may comprise a fixation element 320. The insertable element 112 may be fixedly attached to the drive arm 312 via the fixation element 320.

Figure 8:
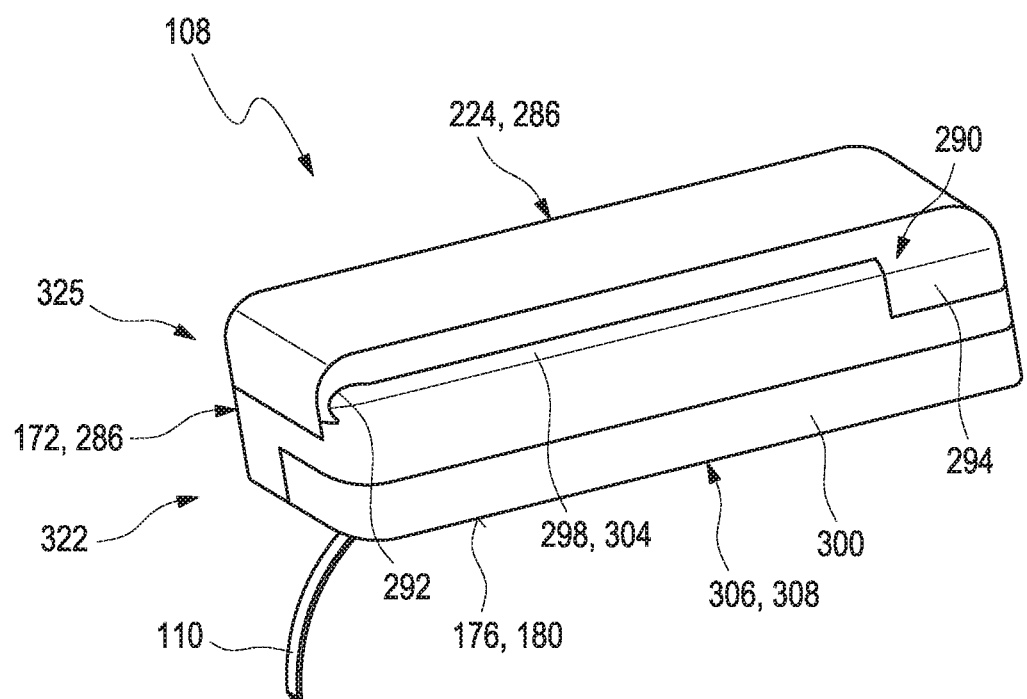
FIGS. 8A and 8B show a further exemplary embodiment of a medical device in different perspective views.
Figure 8:
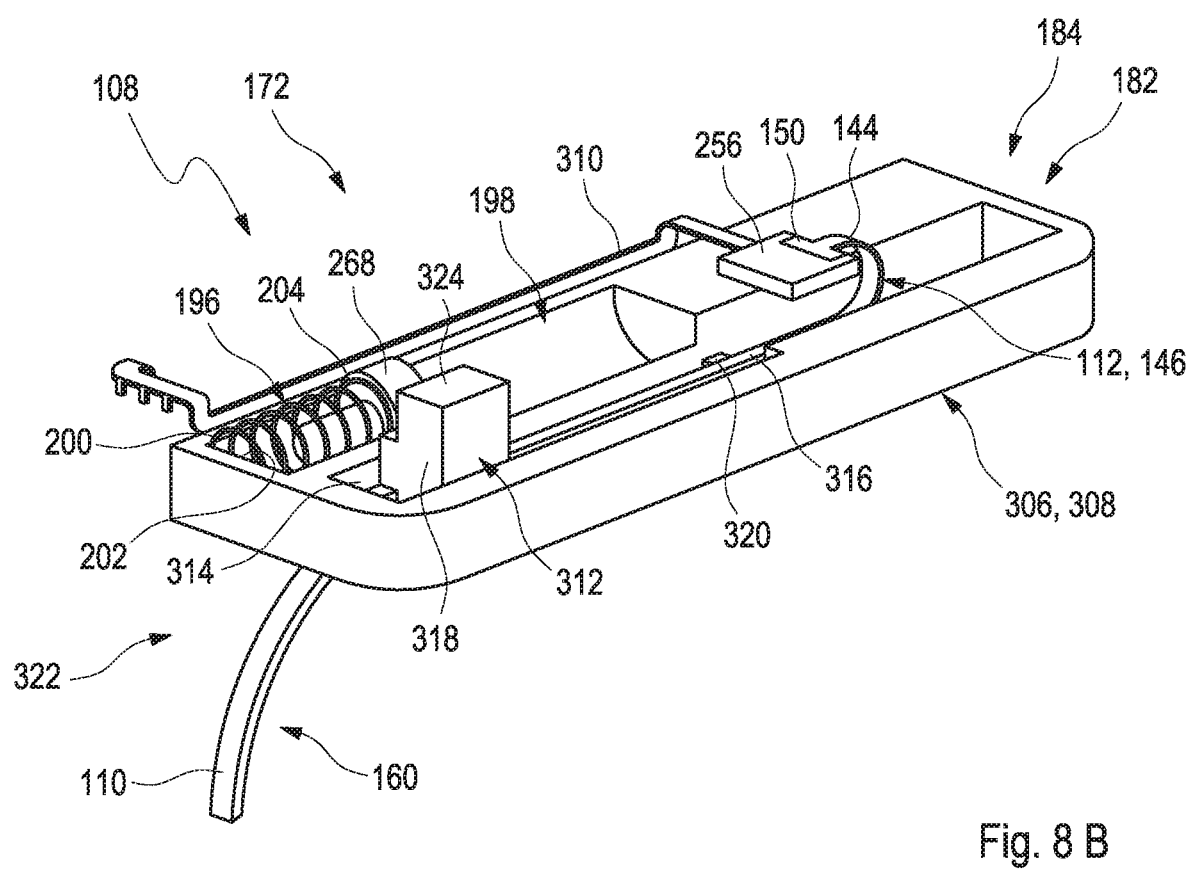

FIGS. 8A and 8B show a further exemplary embodiment of a medical device 108 in different perspective views. The medical device 108 as shown in FIGS. 8A and 8B corresponds, at least in large part, to the medical device 108 as illustrated in FIGS. 7A and 7B. Thus, reference may be made to the description of FIGS. 7A and 7B above.

The medical device 108 as shown in FIG. 8A is shown in a second state 322. In the second state 322, the electronics unit 224 and the patch 174 are in an assembled state 324. The linear sliding receptacles 292 and the linear sliding guide rails 298, in conjunction, form a linear sliding connector 325 configured for establishing a releasable mechanical connection between the electronics unit 224 and the patch 172. The linear sliding guide rail 298 of the patch 172 is received in the linear sliding receptacle 292 of the electronics unit 224 (not shown).

In FIG. 8B, the functional module 308 is shown. When the electronics unit 224 is mounted onto the patch 172 via the linear sliding mechanism 290, the insertion cannula 110 may be transformed into the second configuration 160 and may, at least partially, be located outside of the patch 172 in the inserted position. By applying the linear sliding mechanism 172, the drive arm 312 may be configured to be moved along the drive arm receptacle 314 of the patch 172. Specifically, the electronics unit 124 may move a drive arm protrusion 324, which may exemplarily be located at the end 318 of the drive arm 312. The insertable element 112 may be configured to be moved along with the insertion cannula 110 as the insertable element 112 is fixedly attached to the drive arm 312 via the fixation element 320. Further, the return spring 196 may be configured to be compressed when the linear sliding mechanism 290 is applied.

Figure 9:
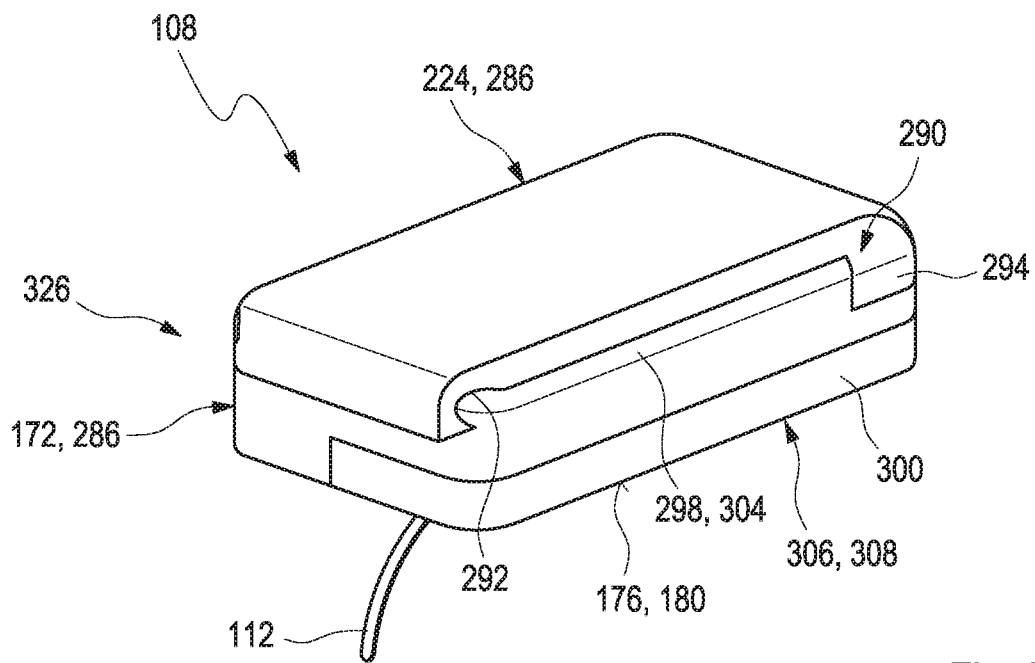
FIGS. 9A and 9B show a further exemplary embodiment of a medical device in different perspective views.
Figure 9:
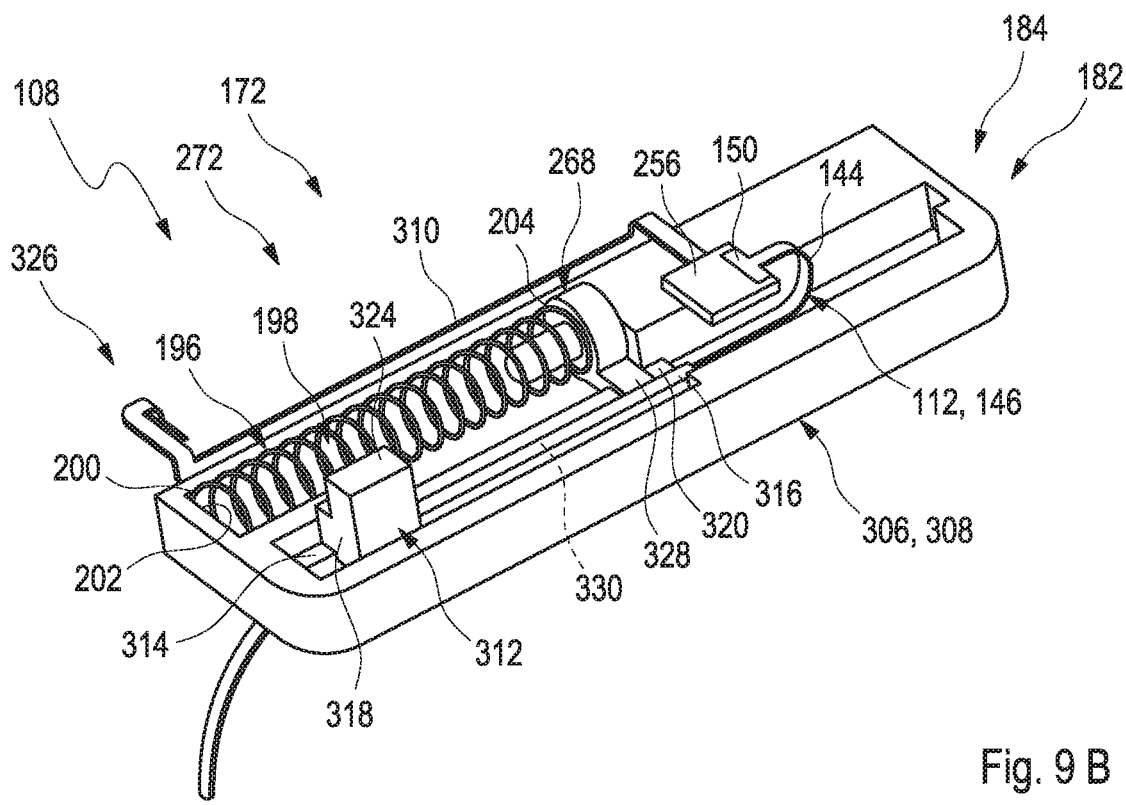

FIGS. 9A and 9B show a further exemplary embodiment of the medical device 108 in different perspective views. The medical device 108 as illustrated in FIGS. 9A and 9B corresponds, at least in large part, to the medical device 108 as illustrated in FIGS. 7A to 8B. Thus, reference may be made to the description of FIGS. 7A to 8B above.

In FIGS. 9A and 9B, the medical device 108 is shown in a third state 326 wherein the insertion cannula 110 may be withdrawn into the patch 172. The insertable element 112 may be configured to stay outside of the patch 172. The return spring 196 may be in the outstretched configuration 172 as illustrated in FIG. 9B and the cannula sleeve 268 may be configured to move from the end 318 of the drive arm 312 to the end 316 of the drive arm 312. The cannula sleeve 268 may have a cannula sleeve protrusion 328 which may be movably received in a cannula sleeve protrusion receptacle 330 of the drive arm 312. The cannula sleeve protrusion receptacle 330 may extend along the drive arm 312.

Figure 10:
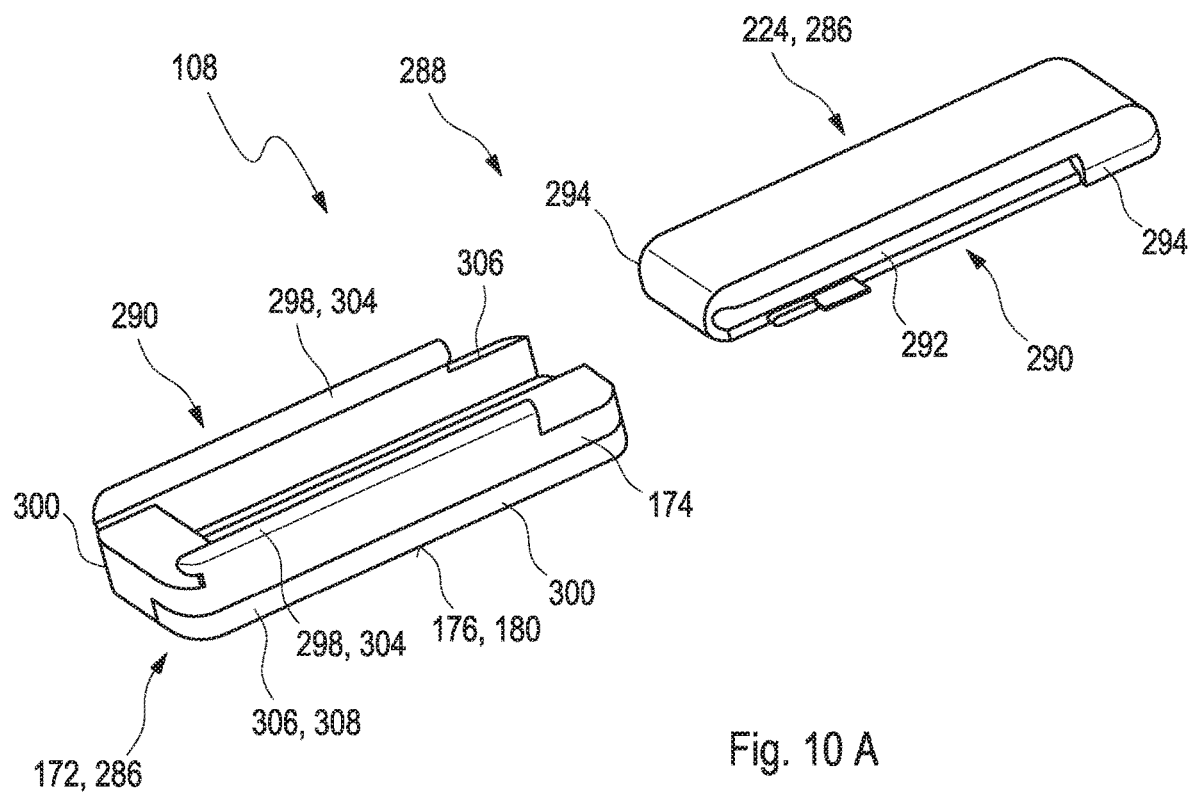
FIGS. 10A and 10B show a further exemplary embodiment of a medical device in different perspective views.
Figure 10:
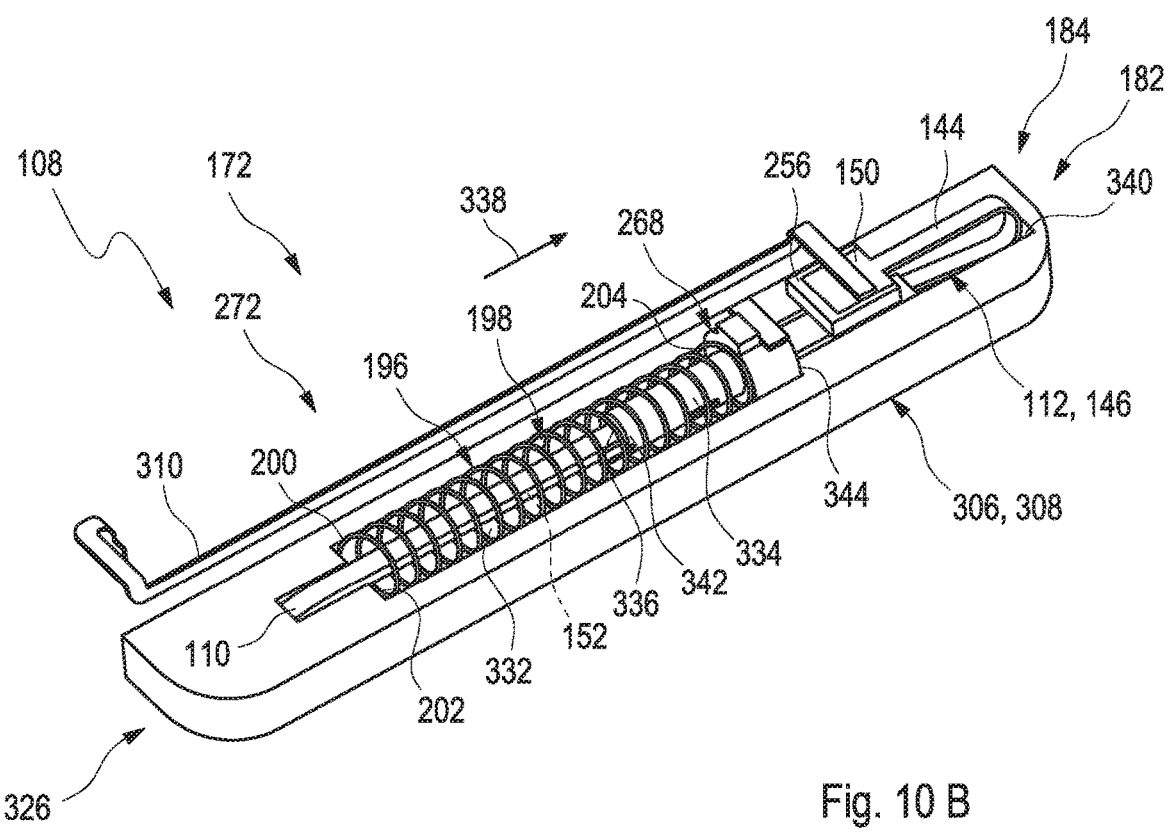

FIGS. 10A to 10B show a further exemplary embodiment of a medical device 108 in different perspective views. The medical device 108 as illustrated in FIGS. 10A and 10B corresponds, at least in large part, to the medical device 108 as illustrated in FIGS. 7A to 9B. Thus, reference may be made to the description of FIGS. 7A to 9B above.

In FIG. 10A, the electronics unit 124 and the patch 172 are shown in an initial state 288. The electronics unit 124 and the patch 172 may be in a disassembled state 289. The medical device 108, specifically the integrated insertion mechanism 182, may have the linear sliding mechanism 290. The electronics unit 124 may have the linear sliding receptacles 292 and the patch 172 may have the linear sliding guide rails 298.

Further, the patch 172 may comprise the two parts 306. One of the two parts 306 may correspond to the functional module 308 which is illustrated in FIG. 10B. The functional module 308 may have the insertable element 112 which is at least partially received in the insertion cannula 110. The integrated insertion mechanism 182 may have the return spring 196. The return spring 196 may be received in the receptacle 198. Further, the insertion cannula 110 may also be received in the receptacle 198. Specifically, the insertion cannula 110 may be received within an interior 332 of the return spring 196. The first end 200 of the return spring 196 may be attachable to the sidewall 202 of the receptacle 198. Further, the return spring 196 may comprise the second end 204. The second end 204 may be attached to the cannula sleeve 268. The cannula sleeve 268 may have a cannula sleeve extension 334 which extends from the cannula sleeve 268 into the return spring 196. The cannula sleeve extension 334 may have a cannula sleeve extension opening 336 which fully penetrates the cannula sleeve 268, specifically the cannula sleeve extension 334, along a direction of extension 338. The middle part 152 of the insertable element 112 may be inserted or received in the cannula sleeve extension opening 336. Thus, the in vivo distal end 142 (not shown) may be received in the insertion cannula 110, and the ex vivo proximal end 144 may be received in a receptacle 340 of the patch 172 adjacent to the receptacle 198.

Figure 11:
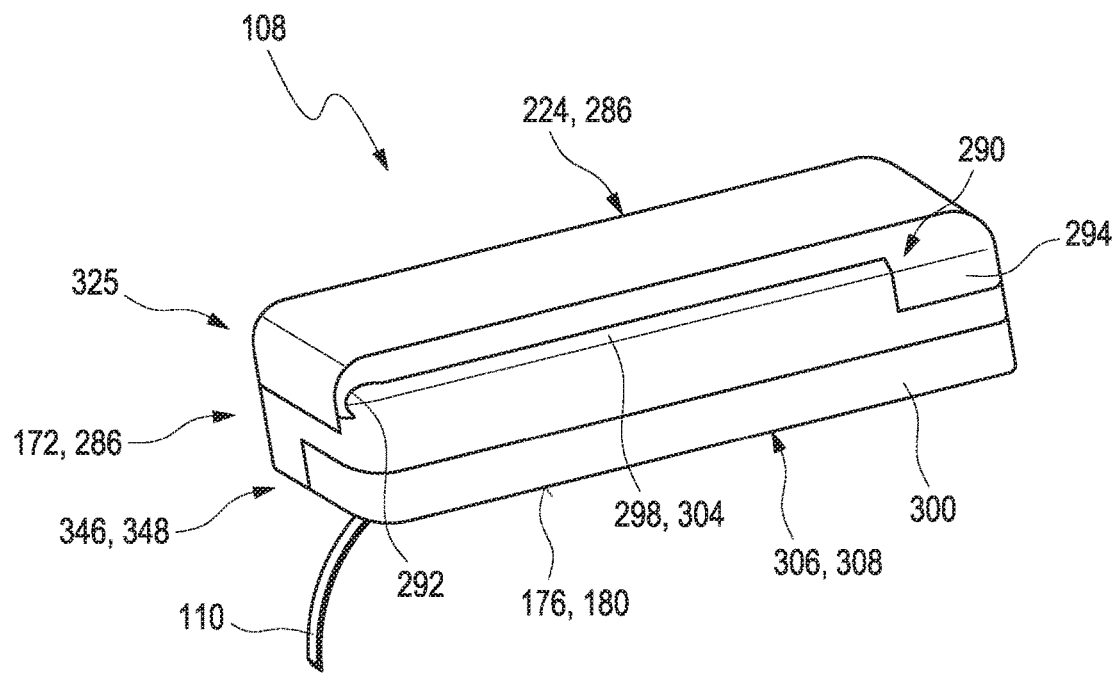
FIGS. 11A and 11B show a further exemplary embodiment of a medical device in different perspective views.
Figure 11:
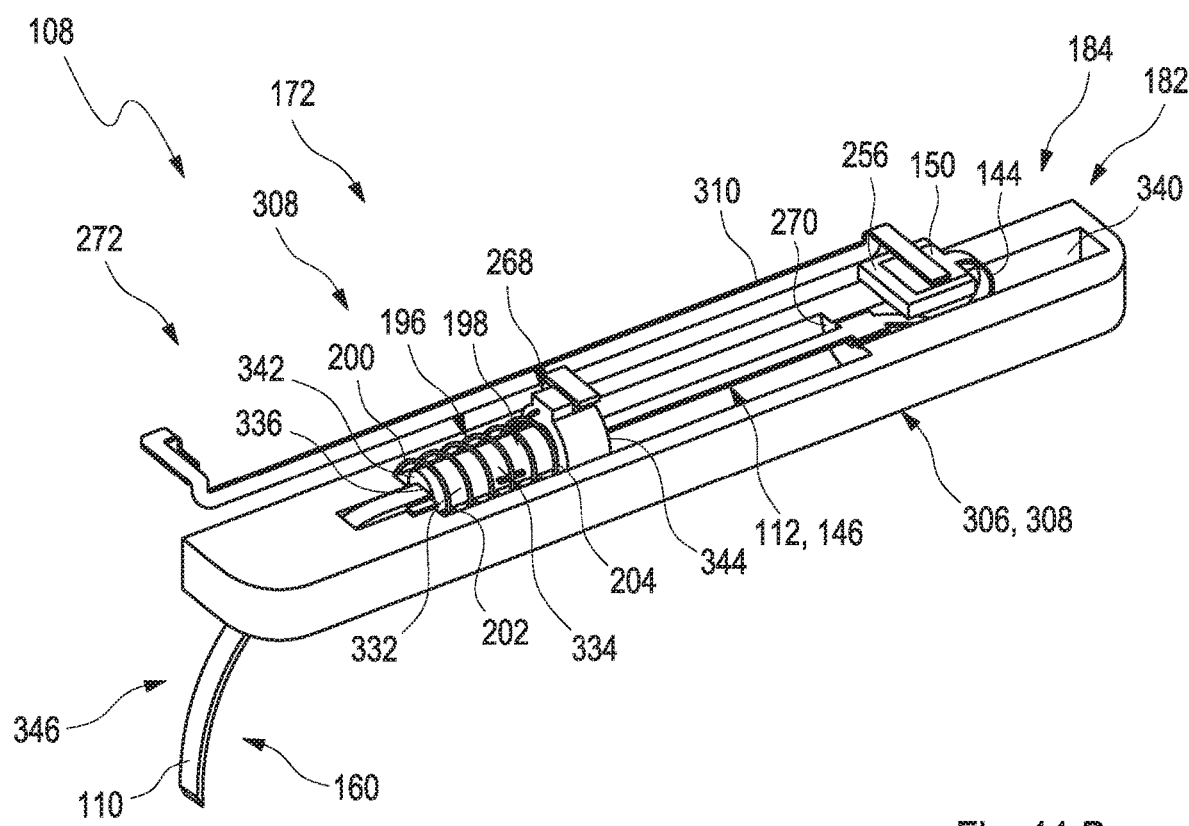

In FIGS. 11A and 11B, a further exemplary embodiment of the medical device 108 is shown. The medical device 108 corresponds, at least in large part, to the medical device 108 as shown in FIGS. 10A to 10B. Thus, reference can be made to the description of FIGS. 10A and 10B above.

The medical device 108 as shown in FIG. 11A is shown in a second state 346. In the second state 346, the electronics unit 224 and the patch 174 are in an assembled state 348. The linear sliding guide rail 298 of the patch 172 is received in the linear sliding receptacle 292 of the electronics unit 224.

In FIG. 11B, the functional module 308 is shown. When the electronics unit 224 is mounted onto the patch 172 via the linear sliding mechanism 290, the insertion cannula 110 is transferred from the storage position inside the patch 172 into the inserted position, thereby being transferred into the second configuration 160 and may, at least partially, be located outside of the patch 172. When being transferred from the storage position inside the patch 172 into the inserted position, the insertion cannula 110, e.g., a tip of the insertion cannula 110, as in the other embodiments, moves along a curved insertion path. By applying the linear sliding mechanism 290, the cannula sleeve 268 may be configured to be moved along the receptacle 198 of the patch 172. Further, the return spring 196 may be configured to be compressed when the linear sliding mechanism 290 is applied.

Figure 12:
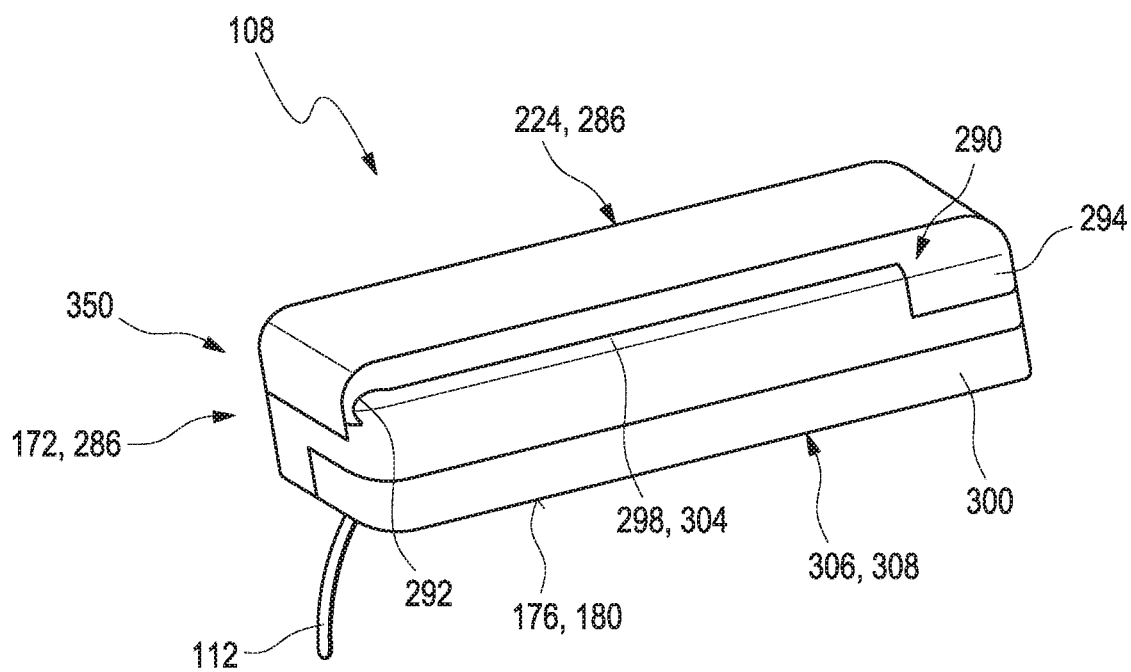
FIGS. 12A and 12B show a further exemplary embodiment of a medical device in different perspective views.
Figure 12:
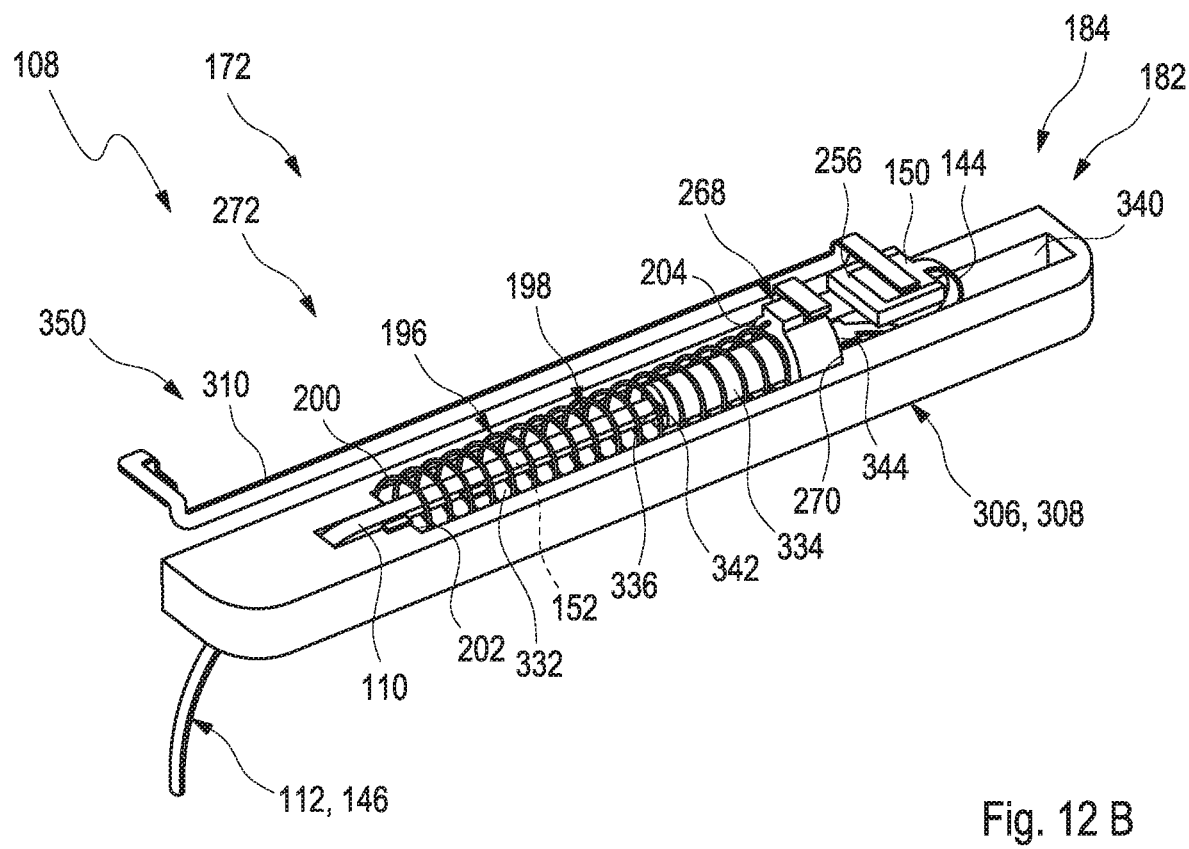

In FIGS. 12A and 12B, a further exemplary embodiment of the medical device 108 is shown. The medical device 108 corresponds, at least in large part, to the medical device 108 as shown in FIGS. 10A to 11B. Thus, reference can be made to the description of FIGS. 10A and 11B above.

In FIGS. 12A and 12B, medical device 108 is shown in a third state 350. Thereby, the insertion cannula 110 may be withdrawn into the patch 172. The insertable element 112 may be configured to stay outside of the patch 172. The return spring 196 may be in the outstretched configuration 172 as illustrated in FIG. 12B and the cannula sleeve 268 may be configured to move from the sidewall 202 of the receptacle 198 to the further sidewall 270 of the receptacle 198.

Figure 13:
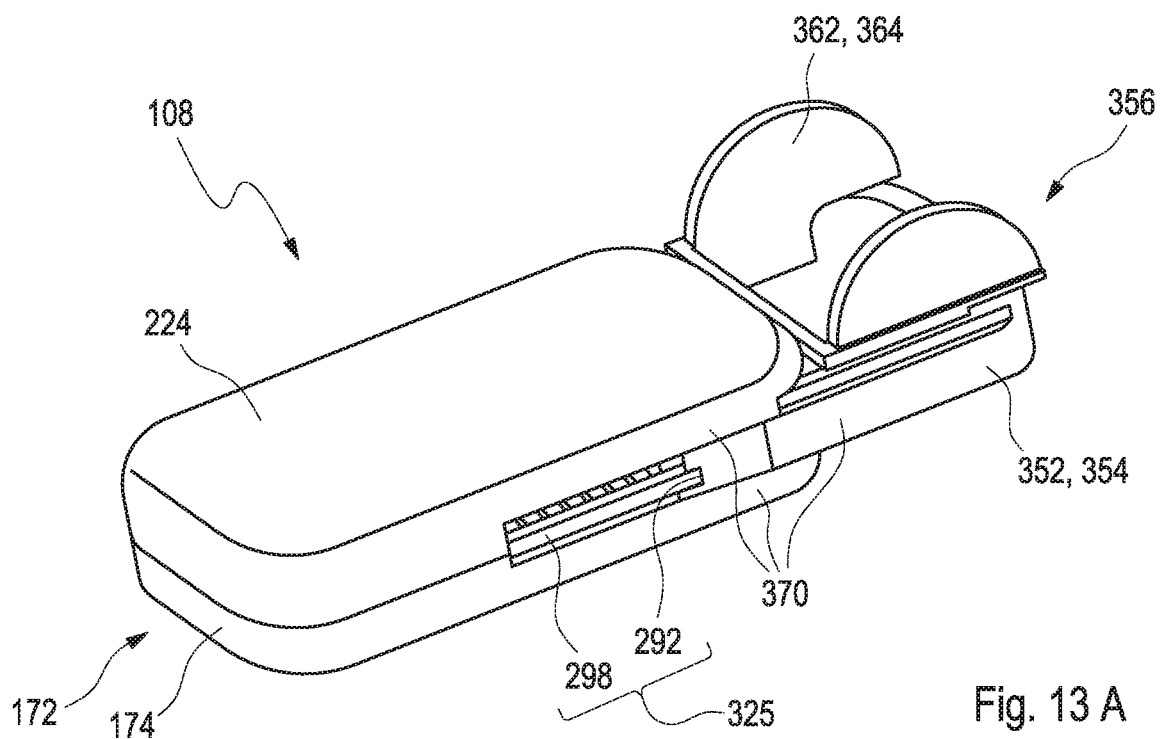
FIGS. 13A, 13B, 13C, 13D and 13E show a further exemplary embodiment of a medical device in different perspective views.
Figure 13:
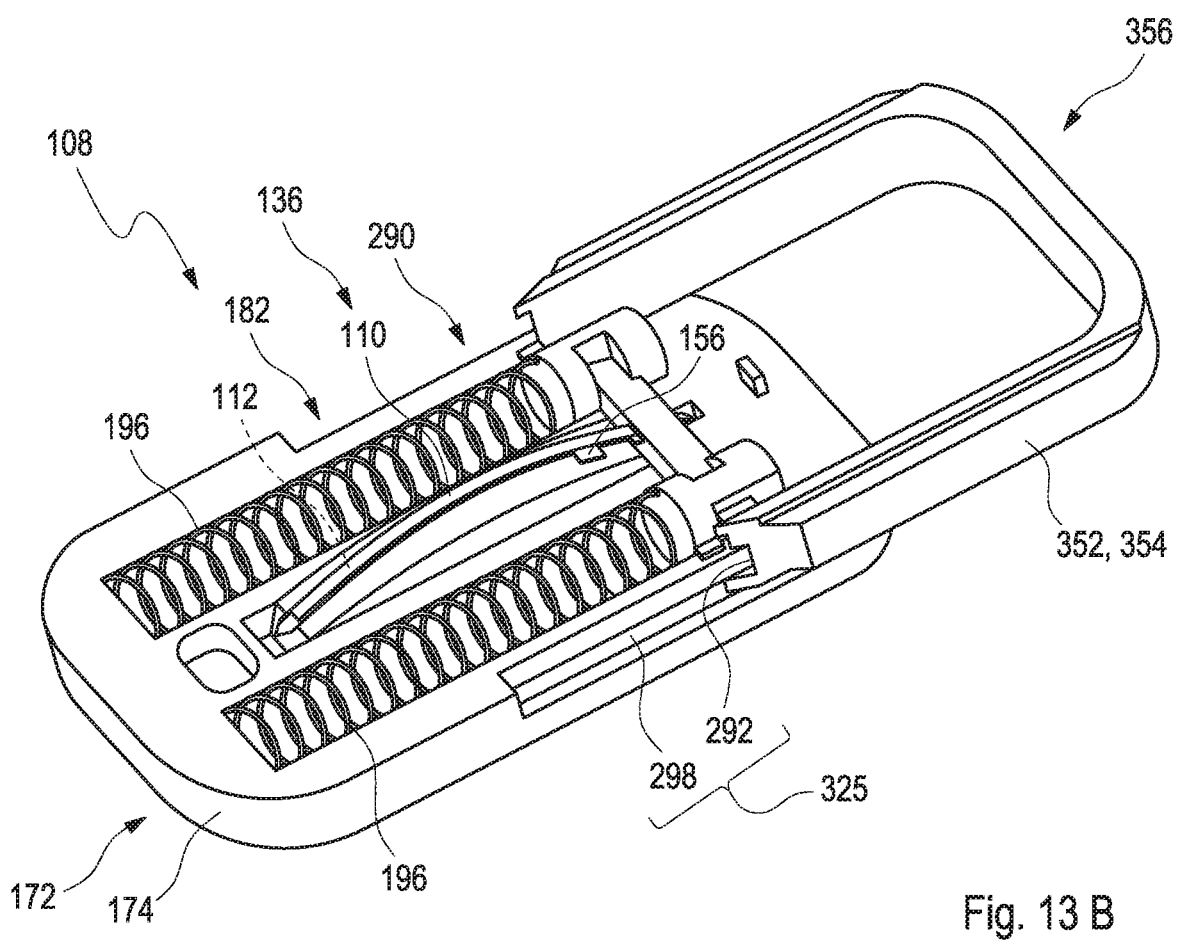
Figure 13:
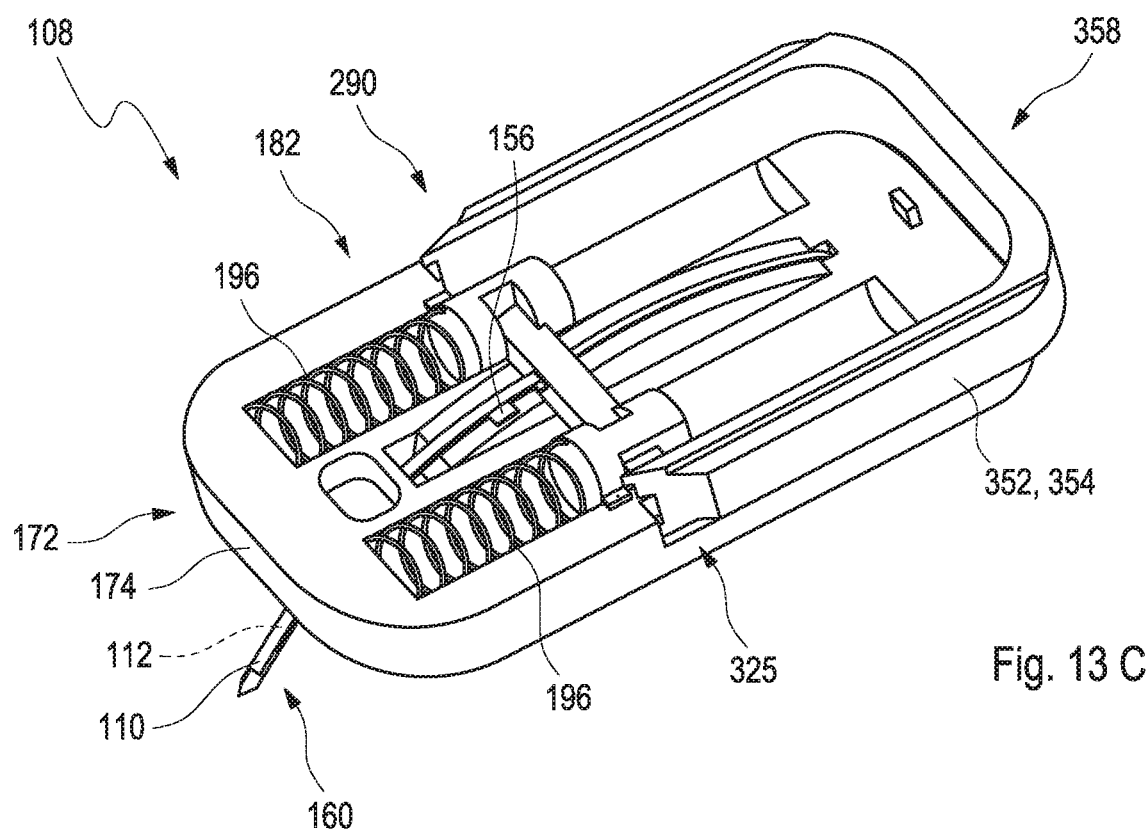
Figure 13:
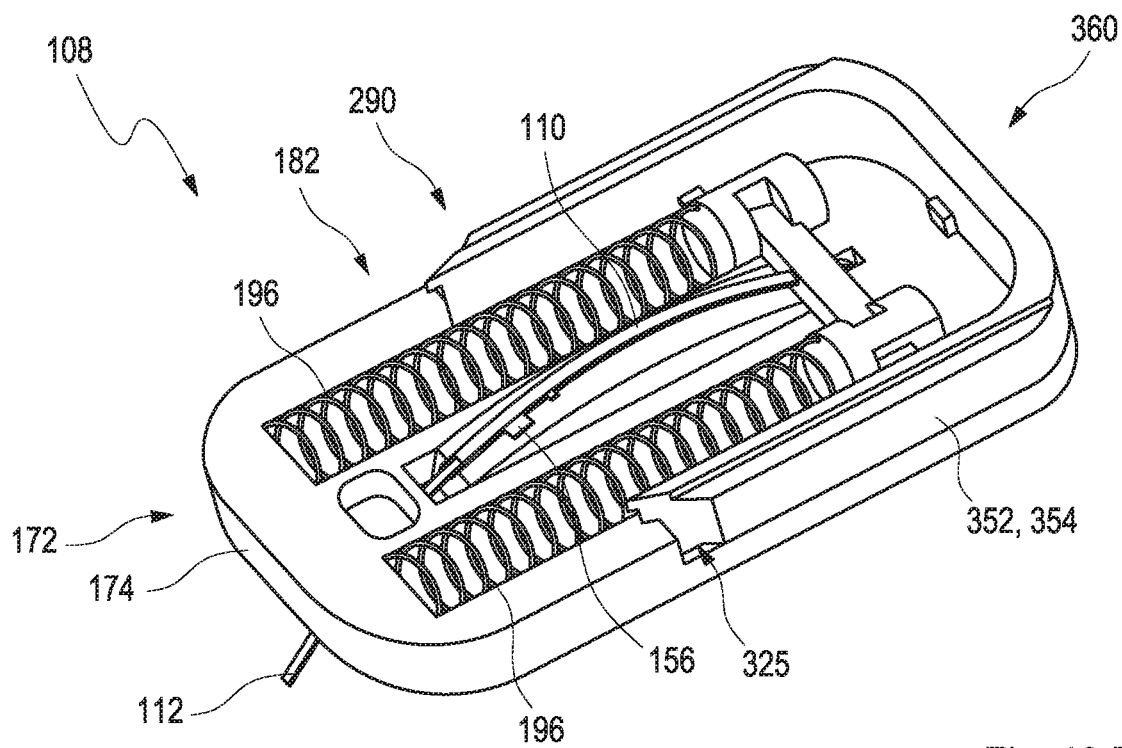
Figure 13:
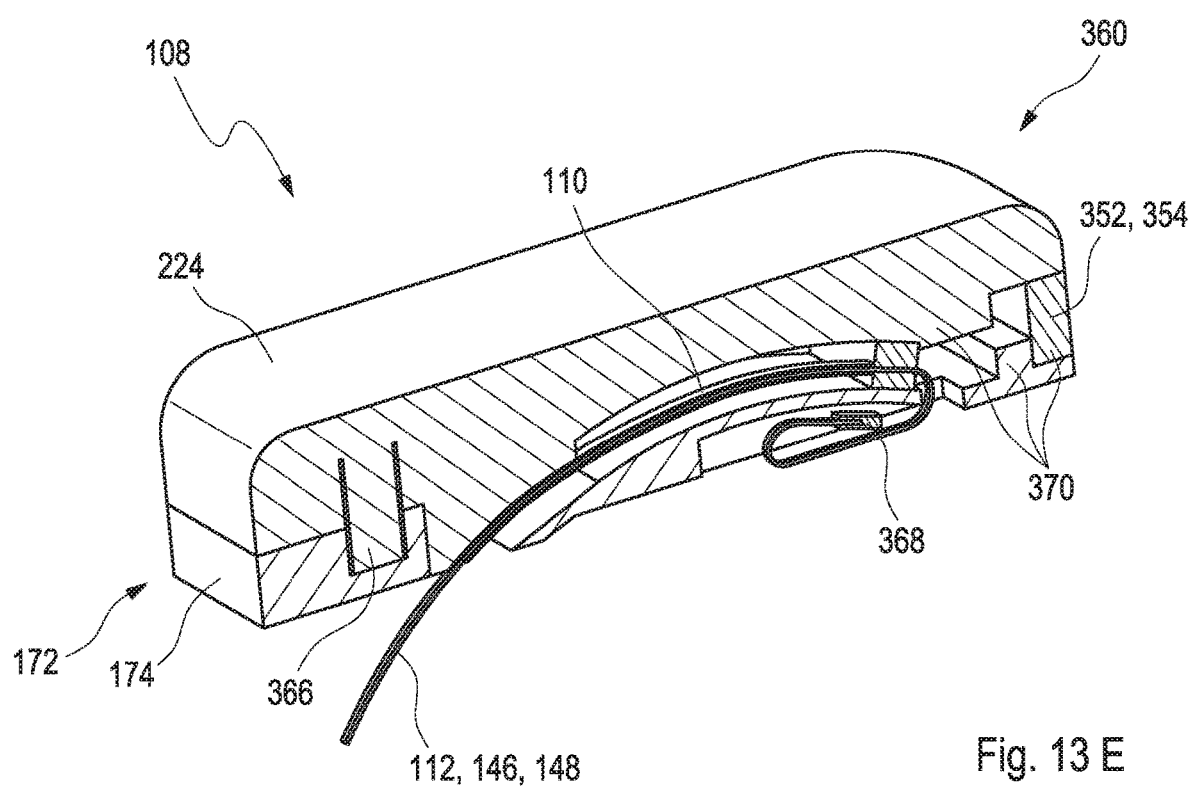
Figure 14:
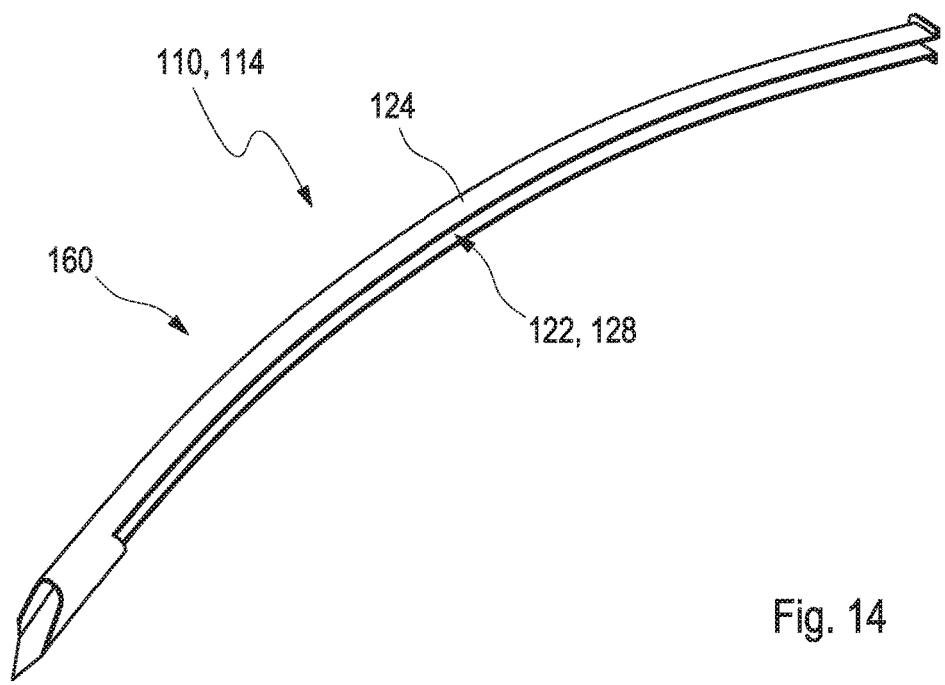
FIG. 14 shows a further exemplary embodiment of an insertion cannula.

In FIGS. 13A to 13E, a further embodiment of a medical device 108 is shown, which, in large part, is similar to the embodiments shown in FIGS. 7A to 12B. FIG. 13A shows a perspective view of the medical device in a closed state; FIG. 13B shows a perspective view with an electronics unit removed, in a standby position; FIG. 13C shows the setup of FIG. 13B in a semi-actuated position; and FIG. 13D shows the setup of FIG. 13B in an actuated position. FIG. 13E shows a cross-sectional view in a fully actuated position. FIG. 14 shows a further exemplary embodiment of an insertion cannula to be used in the setup of FIGS. 13A to 13E. FIGS. 13A to 13E and 14 will be explained in conjunction below.

The medical device 108, as shown in FIG. 13A, as in the exemplary embodiments of FIGS. 7A and 12B, again, comprises a patch 172 with a patch base 174 for attachment to the skin of the user. Further, the medical device 108 may comprise an electronics unit 224, as depicted in FIG. 13A, or, additionally or alternatively, another functional unit, such as a pump unit, depending on the functionality of the medical device 108. The electronics unit 224 and/or the functional unit may be connected to the patch base 174, by using guide rails and/or other types of connection mechanisms.

Further, as in the preceding exemplary embodiments, the medical device 108, again, comprises an insertion cannula 110, with an insertable element 112 disposed therein. An exemplary embodiment of the insertion cannula 110 is shown in FIG. 14. The insertion cannula 110, as an example, may be a slotted insertion cannula 114, having a rectangular cross section and having a slot 128 disposed at a smaller side of the insertion cannula 110. The insertion cannula 110 comprises a wall 124 which, as an example, may be made of flexible stainless steel. In absence of external forces, e.g., in the inserted position shown in FIGS. 13D and 13E, the insertion cannula 110, which is a pre-bended insertion cannula 110, may assume a second configuration 160, as depicted in FIG. 14, in which the insertion cannula 110 is bent. When retracted into the patch 172, i.e. into the storage position, the insertion cannula 110, as shown, e.g., in FIG. 13B, may assume a first configuration 136, in which the insertion cannula 110 may bended to a lesser extent or is stored even in an essentially flat configuration, into which the insertion cannula 110 may be forced by the patch 172. Alternatively, in the storage position, the insertion cannula 110 may also have the same radius of curvature as in the extended position, such that the insertion cannula, in the first and second configurations 136, 160, may also have the same configuration of bending.

The medical device 108, again, comprises an integrated insertion mechanism 182, which, in this exemplary embodiment, is designed as a linear sliding mechanism 290. The linear sliding mechanism 290, as in the preceding embodiments of FIGS. 7A to 12B, may fully or partially be actuated by at least one element connected or connectable to the patch base 174. Thus, the integrated insertion mechanism 182 may be configured for being driven by a connecting force exerted when connecting the at least one element to the patch base. In principle, the electronics unit 224 and/or another type of functional unit connected or connectable to the patch base 174 may be used for actuating the integrated insertion mechanism 182. In this embodiment shown in FIGS. 13A to 13E, however, a separate slider 352 is used as an element connected or connectable to the patch base 174, for driving the insertion mechanism 182. This additional slider 352, as an example, may have the shape of a "U" and/or may form a bracket 354. The slider 352 may be configured for sliding along an outer side of the patch base 174 by using a linear sliding guide rail 298 of the patch base 174 and a linear sliding receptacle 292 of the slider 352 which, in conjunction, may form a sliding connector 325, which may be releasable. The slider, by the linear sliding connector 325, may be brought from a standby position 356, as shown in FIGS. 13A and 13B, over one or more semi-actuated positions 358, as shown e.g. in FIG. 13C, into an actuated position 360, as shown in FIG. 13D. In the standby position, as shown in FIG. 13B, the insertion cannula 110 may be in the storage position, assuming the first configuration 136, with the insertable element 112 disposed therein. In the semi-actuated position 358, shown in FIG. 13C, the insertion cannula 110 may be transferred into the body tissue, thereby continuously being transferred from the storage position into the inserted position and being transformed from the first configuration 136 into the second configuration 160. Again, when being transferred from the storage position into the inserted position, the insertion cannula 110, e.g., a tip of the insertion cannula 110, moves along a curved insertion path. The insertion cannula 110 may be pushed into the body tissue by the driving force exerted by the slider 352. Simultaneously, one or, as in this exemplary embodiment, two return springs 196 may be compressed, as shown in FIG. 13C. Once fully extended into the body tissue, as shown by the transition between FIGS. 13C and 13D, the insertion cannula 110 is mechanically decoupled from the slider 352 and is retracted into the patch base 174 by the return springs 196. The insertable element 112 remains inside the body tissue, held e.g. by a protrusion 156, as discussed above in the context of FIGS. 1A to 1C.

In the standby position, the slider 352, as an example, may be secured by at least one removable securing element 362, as shown e.g. in FIG. 13A. The removable securing element 362, as an example, may simply be forced into the U-shape, thereby preventing the slider 352 from being pushed into the actuated position 360. The securing element 362 may provide multiple functions. Thus, besides the securing effect, the securing element 362 may also be used for desiccation purposes and, thus, may fully or partially be made of a desiccant 364.

As shown in the cross-sectional view of FIG. 13E, the electronics unit 224 may be connected to the patch 172 and/or to the patch base 174 by an electronics unit plug 366. Depending on the type of connection between the electronics unit 224 and the patch base 174, other types of electrical connectors may also be used. Further, depending on the type of insertable element 112, the insertable element 112 may also be connected to one or more of the patch 172, the patch base 174, the electronics unit 224 and/or another type of functional element connected to the patch base 174, such as a pump unit. In the exemplary embodiment shown in FIG. 13E, as an example, the insertable element 112 may fully or partially be embodied as a sensor 146, specifically as an analyte sensor 148, which may be connected to the patch base 174 via at least one sensor plug 368, as discussed previously, e.g., in the context of FIG. 7B. Other connections are feasible, e.g., in the case of the insertable element 112 being an infusion cannula, a fluid connection.

As shown in the embodiment of FIGS. 13A to 13E, as well as in the preceding embodiments, at least one element connected or connectable to the patch base 174 may be used for driving the insertion cannula 110. The element connected or connectable to the patch base 174 may, as outlined above, be or may comprise a bracket or an electronics unit or another type of element. As shown therein, the term "connectable to the patch base" generally may imply the option that the element is brought from a first position into a second position, relative to the patch base 174. Thus, as shown in FIG. 13A and in FIG. 13B, the slider 352, in the standby position 356, protrudes from the patch 172 and from an overall housing 370 of the medical device 108. This state, which may also be referred to as a disconnected state, is transferred into the state shown in FIG. 13D and in FIG. 13E, in which the slider 352 is in the actuated position 360, thereby being connected to the patch base 174. In this state, the slider 352 is flush with a housing 370 of the medical device 108 and does not protrude from the housing 370 any longer and forms part of this housing 370.

Figure 15:
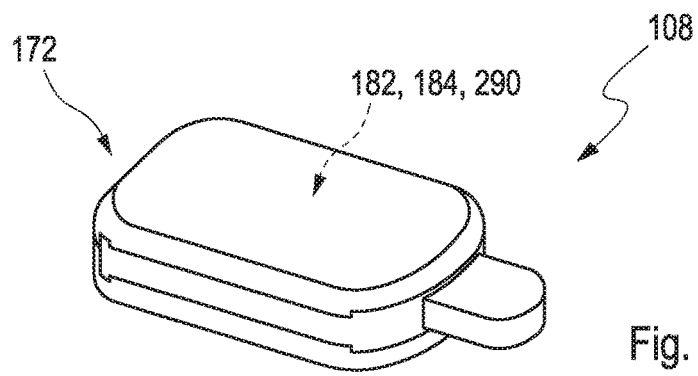
FIGS. 15A, 15B, 15C, and 15D show a further exemplary embodiment of a medical device.
Figure 15:
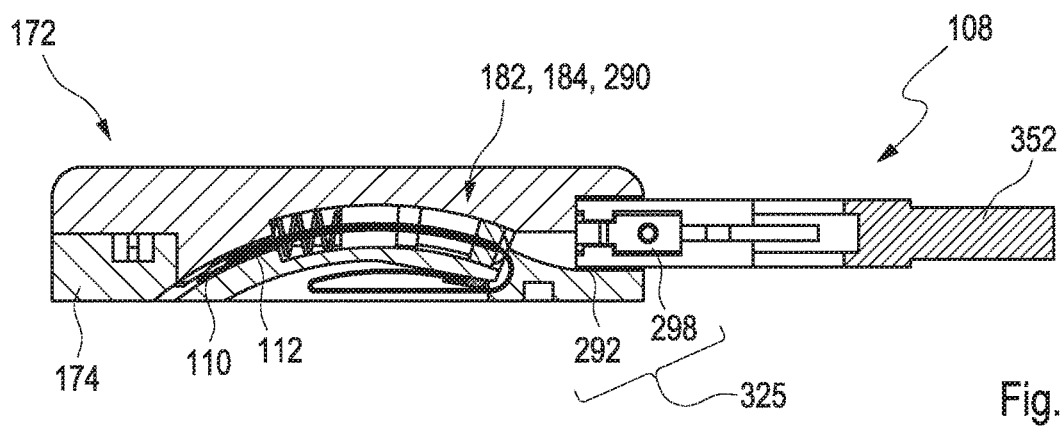
Figure 15:
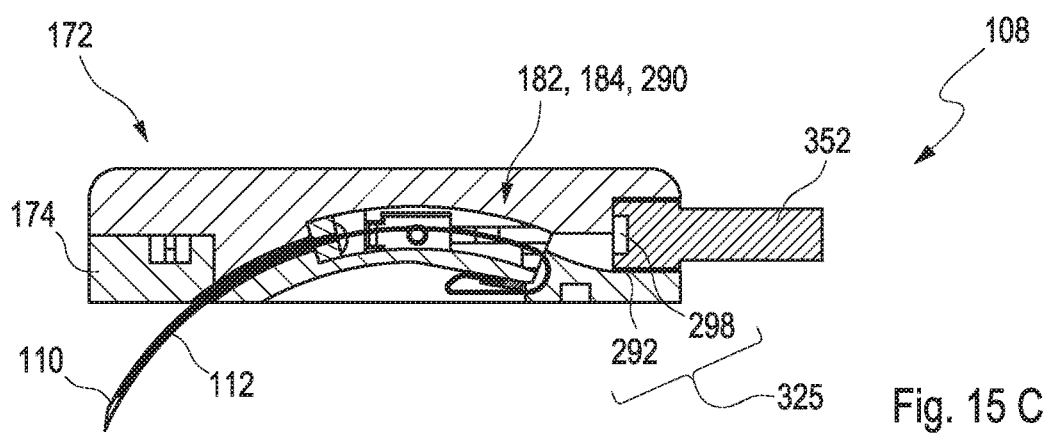
Figure 15:
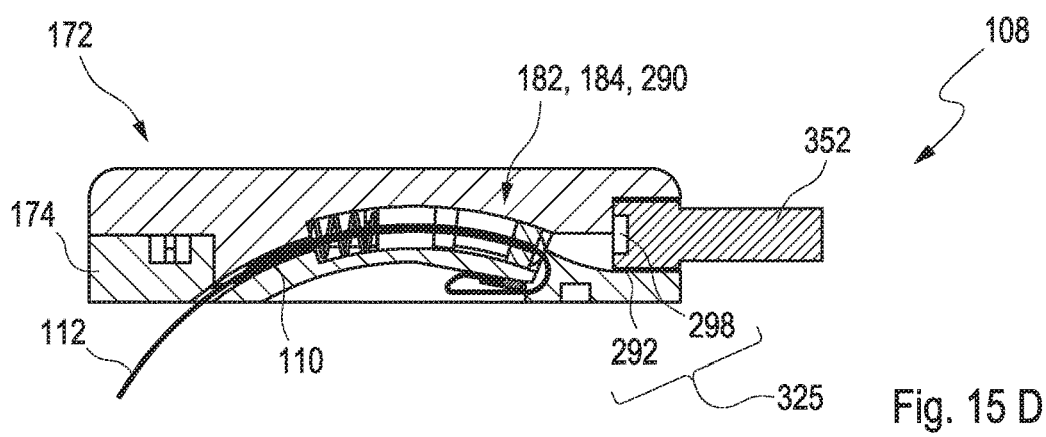

In FIGS. 15A to 15D, a further embodiment of a medical device 108 is shown, which is largely similar to the embodiment shown above in FIGS. 13A to 13E. Thus, for the most part, reference may be made to the description of these Figures above. FIG. 15A shows a perspective view of the medical device 108; FIG. 15B shows the medical device 108 in a standby position, with the insertion cannula 110 in a storage position within the patch 172; FIG. 15C shows the setup in a semi-actuated position, with the insertion cannula 110 being in a fully extended position; and FIG. 15D shows the setup with the insertion cannula 110 being retracted into the patch 172 when the integrated insertion mechanism 182 is further moved towards the fully actuated position (not shown).

The embodiment in FIGS. 15A to 15D differs from the embodiment above in FIGS. 13A to 13E by minor details. For example, as can be seen when comparing FIGS. 15B and 15C, this embodiment shows that the insertion cannula 110, in the storage position and first configuration, and in the inserted position and a second configuration, may also basically have the same radius of curvature. Again, as in the other embodiments, the insertion cannula 110, e.g., a tip of the insertion cannula 110, moves on a curved insertion path during insertion.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS 108 medical device
110 insertion cannula
112 insertable element
114 slotted cannula
116 end
118 slot
120 longitudinal axis
122 lumen
124 wall
128 slot
130 axial direction
132 direction of extension
134 major axis 136 first configuration
138 essentially straight shape
140 essentially flat shape
142 in vivo distal end
144 ex vivo proximal end
146 sensor
148 analyte sensor
150 contact portion
152 middle part
154 curved shape
156 protrusion
158 direction of insertion
160 second configuration
162 pre-programmed configuration
164 curvature
166 arch form
168 arch form
170 previous configuration
172 patch
174 patch base
176 bottom side
178 front side
180 flat surface
182 integrated insertion mechanism
184 drive unit
186 flexible wire
187 receptacle
188 first end
190 second end
192 bearing area
194 pin
196 return spring
198 receptacle
200 first end
202 sidewall
204 second end
206 protrusion
207 circuit board
208 further receptacle
209 electrical contact
210 passage opening
223 patch cover element
224 electronics unit
226 electronics unit bayonet screw
228 patch bayonet contour
230 bayonet connector
232 sterile packaging
234 skin
236 user
238 adhesive surface
240 body tissue
242 sleeve
243 patch base cover element
244 protrusion
246 further sleeve
248 surface
250 bend
252 longitudinal axis
254 end section
256 ZIF connector
258 middle section
260 first further sleeve protrusion
262 patch base cover element receptacle
264 second further sleeve protrusion
266 end
268 cannula sleeve
270 further side wall
272 outstretched configuration
274 arm
276 middle section
278 tensioned configuration
280 ramp
282 hook
284 second further sleeve protrusion receptacle
286 separate component
288 initial state
289 disassembled state
290 linear sliding mechanism
292 linear sliding receptacle
294 longitudinal side
296 longitudinal axis
298 linear sliding guide rail
300 longitudinal side
302 longitudinal axis
304 protrusion
306 part
308 functional module
310 electrical contact
312 drive arm
314 drive arm receptacle
316 end
318 end
320 fixation element
322 second state
324 drive arm protrusion
326 third state
328 cannula sleeve protrusion
330 cannula sleeve protrusion receptacle
332 interior
334 cannula sleeve extension
336 cannula sleeve extension opening
338 direction of extension
340 receptacle
342 ex vivo proximal end
344 second end
346 second state
348 assembled state
350 third state
352 slider
354 bracket
356 standby position
358 semi-actuated position
360 actuated position
362 securing element
364 desiccant
366 electronics unit plug
368 sensor plug
370 housing

What is claimed is:

1. A medical device for transcutaneously inserting an insertable element into a body tissue, wherein the medical device comprises:
an insertable element, wherein the insertable element includes an in vivo distal end for subcutaneous insertion and at least one ex vivo proximal end;
an insertion cannula for subcutaneously inserting the insertable element, the insertion cannula having a lumen which fully or partially is enclosed by a wall of the insertion cannula, wherein the insertable element is received in the lumen, wherein the insertion cannula is a pre-bended insertion cannula;
wherein the medical device further comprises at least one patch configured to be mounted onto the skin of a user, wherein the patch comprises a patch base and an integrated insertion mechanism for driving the insertion cannula from a storage position within the patch into an inserted position within the body tissue; and wherein the insertion cannula has a tip and the tip of the insertion cannula follows an insertion path, during movement of the insertion cannula from the storage position to the inserted position, that is at least partially non-straight.

2. The medical device according to claim 1, wherein the insertion cannula is at least partially made of a material selected from the group consisting of: steel, stainless steel, and a plastic material.

3. The medical device according to claim 1, wherein the insertion cannula is pre-bended in such that the insertion cannula at least partially has the shape of a segment of a circle.

4. The medical device according to claim 3, wherein the insertion path is at least partially shaped as a segment of a circle.

5. The medical device according to claim 1, wherein the medical device is configured such that the insertion cannula is withdrawn into the medical device after insertion of the insertable element.

6. The medical device according to claim 1, wherein the integrated insertion mechanism comprises a drive unit configured to urge the insertion cannula in a direction of insertion.

7. The medical device according to claim 1, wherein the integrated insertion mechanism is a linear sliding mechanism.

8. The medical device according to claim 1, wherein the medical device further comprises at least one element connected or connectable to the patch base, wherein the integrated insertion mechanism is configured to be driven by a connecting force exerted when connecting the element to the patch base or when moving the element relative to the patch base.

9. The medical device according to claim 8, wherein the at least one element connected or connectable to the patch base comprises a linear sliding receptacle and the patch comprises a linear sliding guide rail or vice versa, wherein the linear sliding receptacle and the linear sliding guide rail in conjunction form a linear sliding connector configured for moving the element relative to the patch base or for establishing a releasable mechanical connection between the at least one element connectable to the patch base and the patch.

10. The medical device according to claim 8, wherein the at least one element connected or connectable to the patch base comprises an element selected from the group consisting of: an electronics unit configured for interacting with the insertable element; a slider; and a bracket.

11. The medical device according to claim 8, wherein the at least one element connected or connectable to the patch base is configured to be brought from a standby position into an actuated position, wherein the medical device is configured to insert the insertion cannula into the body tissue when the at least one element connected or connectable to the patch base is brought into the actuated position.

12. The medical device according to claim 11, wherein the medical device is further configured for retracting the insertion cannula once the actuated position has been reached.

13. The medical device according to claim 11, wherein the medical device further comprises at least one removable securing element, wherein the securing element is configured for securing the at least one element connected or connectable to the patch base in the standby position.

14. The medical device according to claim 11, wherein the at least one element connected or connectable to the patch base, when in the actuated position, is flush with a housing of the medical device.

15. An analyte measurement device for detecting at least one analyte in a body fluid, the analyte measurement device comprising at least one medical device according to claim 1, wherein the insertable element comprises an analyte sensor for detecting the at least one analyte in the body fluid, the analyte measurement device further having an evaluation device interacting with the analyte sensor.

16. A medication device for delivering at least one medication to a user, the medication device comprising at least one medical device according to claim 1, wherein the insertable element comprises at least one of an infusion cannula or a dosing tube, wherein the medication device further comprises a medication pump fluidly coupled to the insertable element.

17. A method for transcutaneously inserting an insertable element into a body tissue, wherein the method comprises:
 a) providing at least one medical device according to claim 1, the medical device further including an electronics unit;
 b) placing the patch base onto the skin; and
 c) inserting the insertable element into the body tissue.

18. The medical device according to claim 1, wherein the insertion cannula has a first configuration when in the storage position and a second configuration when in the inserted position and wherein the insertion cannula is bent to a lesser extent in the first configuration than in the second configuration.

19. The medical device according to claim 18 wherein the insertion cannula is in the first configuration when retracted into the patch and assumes the second configuration when extended outside the patch.

* * * * *